(12) United States Patent
DiCosimo et al.

(10) Patent No.: US 7,867,748 B2
(45) Date of Patent: Jan. 11, 2011

(54) IMMOBILIZED MICROBIAL NITRILASE FOR PRODUCTION OF GLYCOLIC ACID

(75) Inventors: Robert DiCosimo, Chadds Ford, PA (US); Arie Ben-Bassat, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/698,775

(22) Filed: Feb. 2, 2010

(65) Prior Publication Data

US 2010/0136656 A1 Jun. 3, 2010

Related U.S. Application Data

(62) Division of application No. 11/930,744, filed on Oct. 31, 2007.

(51) Int. Cl.
*C12P 21/06* (2006.01)
*C12N 9/00* (2006.01)
*C12N 9/78* (2006.01)
*C07H 21/04* (2006.01)

(52) U.S. Cl. .............. 435/227; 435/69.1; 435/183; 536/23.2

(58) Field of Classification Search .............. None
See application file for complete search history.

(56) References Cited

U.S. PATENT DOCUMENTS

| | | | |
|---|---|---|---|
| 2,175,805 A | 10/1939 | Jacobson | |
| 2,890,238 A | 6/1959 | Sexton | |
| 3,940,316 A | 2/1976 | Commeyras et al. | |
| 4,288,552 A | 9/1981 | Gestrelius | |
| 5,187,301 A | 2/1993 | Cullen et al. | |
| 5,223,416 A | 6/1993 | Endo et al. | |
| 5,234,826 A | 8/1993 | Yamagami et al. | |
| 5,296,373 A | 3/1994 | Endo et al. | |
| 5,326,702 A | 7/1994 | Endo et al. | |
| 5,508,181 A | 4/1996 | Hasimoto | |
| 5,605,793 A | 2/1997 | Stemmer | |
| 5,756,306 A | 5/1998 | Yamaguchi et al. | |
| 5,811,238 A | 9/1998 | Stemmer et al. | |
| 5,814,508 A | 9/1998 | DiCosimo et al. | |
| 5,830,721 A | 11/1998 | Stemmer et al. | |
| 5,837,458 A | 11/1998 | Minshull et al. | |
| 5,846,762 A | 12/1998 | Woodward | |
| 5,998,180 A | 12/1999 | Armitage et al. | |
| 6,037,155 A | 3/2000 | Kobayashi et al. | |
| 6,291,708 B1 | 9/2001 | Cockrem | |
| 6,383,786 B1 | 5/2002 | Chauhan et al. | |
| 6,416,980 B1 | 7/2002 | Chauhan et al. | |
| 6,551,804 B2 | 4/2003 | DiCosimo et al. | |
| 6,870,038 B2 | 3/2005 | Chauhan et al. | |
| 7,148,051 B2 | 12/2006 | Payne et al. | |
| 7,198,927 B2 | 4/2007 | DiCosimo et al. | |
| 7,473,545 B2 | 1/2009 | DiCosimo et al. | |
| 7,638,617 B2 | 12/2009 | DiCosimo et al. | |
| 2004/0138409 A1 | 7/2004 | Hayashi et al. | |
| 2004/0210087 A1 | 10/2004 | Meng et al. | |
| 2006/0160196 A1 | 7/2006 | Foo | |
| 2006/0247467 A1 | 11/2006 | DiCosimo | |

FOREIGN PATENT DOCUMENTS

| | | |
|---|---|---|
| EP | 0486289 A | 5/1992 |
| EP | 0610048 B1 | 8/1994 |
| EP | 0610049 B1 | 8/1994 |
| EP | 1233057 | 8/2002 |
| JP | 06/1056086 | 3/1986 |
| JP | 09/028390 | 4/1997 |
| WO | WO 01/04278 | 1/2001 |
| WO | WO 01/75077 | 10/2001 |
| WO | WO 02/068658 A1 | 9/2002 |
| WO | WO 2006/069110 A2 | 6/2006 |
| WO | WO 2006/069114 | 6/2006 |
| WO | WO 2006/106005 | 12/2006 |
| WO | WO 2007/036235 | 4/2007 |

OTHER PUBLICATIONS

DeGuiulio et al., World J. Microbiol. Biotechnol., 2005, 21, 739-746.
Metz et al., "Identification of Formaldehyde-induced Modifications in Proteins," J. Biol. Chem., 2004, 279(8), 6235-6243.
Asano et al., "Aliphatic Nitrile Hydratase from Arthrobacter sp. J-1 Purification and Characterization," Agricultural Biological Chemistry, 1982, 46(5), 1165-1174.
Mowry, David., "The Preparation of Nitriles," Chemical Reviews, 1948, 42, 189-283.

(Continued)

*Primary Examiner*—Christian L Fronda

(57) ABSTRACT

The present invention is directed to a process for improving the specific activity of a dehydrated enzyme catalyst having nitrilase activity for hydrolysis of glycolonitrile to glycolic acid upon rehydration. In particular, a process is provided comprising pretreating an enzyme catalyst having nitrilase activity with glutaraldehyde, immobilizing the gutaraldehyde-preteated enzyme catalyst and chemically cross-linking the enzyme catalyst prior to dehydration. Upon rehydration, the enzyme catalyst exhibits improved specific nitrilase activity as compared to enzyme catalysts having nitrilase activity that are dehydrated and rehydrated without the processing described herein.

8 Claims, 7 Drawing Sheets

OTHER PUBLICATIONS

Athel Cornish-Bowden, "Nomenclature for incompletely specified bases in nucleic acid sequences: recommendations 1984," Nucleic Acids Research, 1984, 13, 3021-3030.

"Nomenclature and Symbolism for Amino Acids and Peptides," Biochemical Journal, 1984, 219(2), 345-373.

Feng et al., "High-Level Expression and Mutagenesis of Recombinant Human Phophatidylcholine Transfer Protein Using A Synthetic . . . " Biochemistry, 2000, 39(50), 15399-15409.

Outchkourov et al., "Optimization of the Expression of Equistatin in *Pichia pastoris*," Protein Expr Purif, 2002, 24(1), 18-24.

Cowan et al., "Biochemistry and biotechnology of mesophilic and thermophilic nitrile metabolizing enzymes," Extremorphiles, 1998, 2, 207-216.

Pace et al., "The nitrilase superfamily: classification, structure and function," Genome Biol., 2001, 2(1), reviews 0001.1-0001.9.

Chauhan et al., "Purification, cloning, sequencing and over-expression in *Escherichia coli* of a regioselective aliphatic . . . ," Appl. Microbiol. Biotechnol., 2003, 61, 118-122.

Deshpande, Mukund V., "Ethanol Production from Cellulose by Couple Saccharification/Fermentation using Saccharomyces . . . ," Appl. Biochem. Biotechol., 1992, 36(3), 227-234.

Bickerstaff, G. F., Immobilization of Enzymes and Cells, Methods in Biotechnology, 1997, Ch.4, Ch.5, Ch.17, Ch. 32, pp. 27-40, 41-51, 133-141, 289-298 (respectively).

U.S. Appl. No. 11/931,069, Robert DiCosimo, Anna Panova, Henry K. Chenault and Samuel D. Arthur, Sequestration of Formaldehyde . . . , Filed Dec. 31, 2007.

U.S. Appl. No. 11/930,550, Robert DiCosimo, Ben-Bassat; Arie, "Improvement in Immobilized Microbial Nitrilase For Production of Glycolic Acid," Filed Oct. 31, 2007.

International Search Report and Written Opinion of related PCT/US2008/081952 mailed Feb. 3, 2009.

Panova et al., Advanced Synthesis & Catalysis, vol. 349, pp. 1462-1474, 2007.

Ben-Bassat et al., Advanced Synthesis & Catalysis, vol. 350, pp. 1761-1769, 2008.

Desantis, et al., "Creation of a productive, highly enantioselective nitrilase through gene site saturation mutagenesis", J. Am. Chem. Soc., vol. 125, pp. 11476-11477 (2003).

Fromant, M., et al., "Direct random mutagenesis of gene-sized DNA fragments using polymerase chain reaction", Analytical Biochem., vol. 224, pp. 347-353 (1995).

Guthrie, J.P., et al., "Effect of the ACYL substituent on the equilibrium constant for hydration of esters", Canadian J. Chem., vol. 58, pp. 1281-1294 (1980).

Inci, I., "Distribution of glycolic acid between water and different organic solutions", Chem. Biochem. Eng. Q., vol. 16, pp. 81-85 (2002).

Inci, I., et al., "Extraction of glycolic acid from aqueous solutions by trioctyl methylammonium chloride and organic . . . ", J. Chem. Eng. Data, vol. 50, pp. 536-540 (2005).

Lin-Goerke, "PCR-based random mutagenesis using manganese and reduced DNTP concentration", Biotechniques, vol. 23, pp. 409-412 (1997).

Melnikov, A., et al., "Random mutagenesis by recombinational capture of PCR products in *Bacillus subtilis* and . . . ", Nucleic Acids Res., vol. 27, pp. 1056-1062 (1999).

O'Reilly, C., et al., "The nitrilase family of CN hydrolyzing enzymes-a comparative study", J. Appl. Microbiol., vol. 95, pp. 1161-1174 (2003).

Tamada, J.A., et al., "Extraction of carboxylic acids with amine extractants. 1. Equilibria and law of mass action . . . ", Ind. Eng. Chem. Res., vol. 29, pp. 1319-1326 (1990).

Tamada, J.A., et al., "Extraction of carboxylic acids with amine extractants. 2. Chemical interactions and . . . ", Ind. Eng. Chem. Res., vol. 29, pp. 1327-1333 (1990).

Tourneix, D.A., et al., "Regulation of nitrile-hydratase synthesis in a Brevibacterium species", Antonie Van Leeuwenhoek, vol. 52, pp. 173-182 (1986).

Wasewar, K.L., et al., "Reactive extraction of lactic acid using alamine 336 in MIBK: equilibria and kinetics", J. Biotechnol., vol. 97, pp. 59-68 (2002).

Yanisch-Perron, C., et al., "Improved M13 phage cloning vectors and host strains: nucleotide sequences . . . ", NCBI Gen. ID No. 20141090, Accession No. L09137, May 22, 2002.

Notice of Allowance in U.S. Appl. No. 12/210,618, now U.S. Pat. No. 7,638,617, mailed Aug. 27, 2009.

Requirement for Restriction/Election in U.S. Appl. No. 11/712,336, now U.S. Pat. No. 7,473,545, mailed Mar. 28, 2008.

Notice of Allowance in U.S. Appl. No. 11/712,336, now U.S. Pat. No. 7,473,545, mailed Aug. 29, 2008.

Requirement for Restriction/Election in U.S. Appl. No. 11/313,541, now U.S. Pat . No. 7,198,927, mailed Aug. 14, 2006.

Notice of Allowance in U.S. Appl. No. 11/313,541, now U.S. Appl. No. 7,198,927, mailed Nov. 30, 2006.

CLUSTAL W (1.83) multiple sequence alignment

```
SEQ ID NO:4    ----------MVSYNSKFLAATVQAEPVWLDADATIDKSIGIIEEAAQKGASLIAFPEVF
SEQ ID NO:5    ----------MQTRKIVRAAAVQAASPNYDLATGVDKTIELARQARDEGCDLIVFGETW
SEQ ID NO:6    ----------MVEYTNTFKVAAVQAQPVWFDAAKTVDKTVSIIAEAARNGCELVAFPEVF
SEQ ID NO:7    -----MSSNPELKYTGKVKVATVQAEPVILDADATIDKAIGFIEEAAKNGAEFLAFPEVW
SEQ ID NO:8    -------------MKVATVQAEPVILDADATIDKAIGYIEEASKNGAEFIAFPEVW
SEQ ID NO:9    ----------MTTHRIAVIQDGPVPGDAMATAEKMSRLAASAKAQGARLALFPEAF
SEQ ID NO:10   MSTSENTPFNGVASSTIVRATIVQASTVYNDTPATLEKANKFIVEAASKGSELVVFPEAF
SEQ ID NO:11   ----------MADKIIVAAAAQIRPVLFSLEGSVARVLAAMAEAAAAGVQLIVFPETF
SEQ ID NO:12   ----------MADKIIVAAAAQIRPVLFSLEGSVARVLAAMAEAAAAGVQLIVFPETF
SEQ ID NO:13   -----MLGKIMLNYTKNIRAAAAQISPVLFSQQGTMEKVLDAIANAAKKGVELIVFPETF
SEQ ID NO:14   ----------MPKSIVAALQVGSLPEGKAATLEQILGYEQAIREAGARLVVMPEAL
SEQ ID NO:15   ----------MSCHRVAVIQAGTSLFDTEKTLDRMEALCRQAAEQNVELAVFPEAY
SEQ ID NO:16   ----------MSNYPKYRVAAVQASPVLLDLDATIDKTCRLVDEAAANGAKVIAFPEAF
SEQ ID NO:17   ----------MKNYPTVKVAAVQAAPVFMNLEATVDKTCKLIAEAASMGAKVIGFPEAF
SEQ ID NO:18   ----------MTTVKVAAAQIRPVLFSLDGSLQKVLDAMAEAAAQGVELIVFPETF
SEQ ID NO:19   ----------MPKSVVAALQIGALPEGKAATLEQILSYEAAIIEAGAQLVVMPEAL
SEQ ID NO:20   ----------MSQRDSFRAAAVQAAPVWLDGAATVDKCVALIEEAADNGAALIAFPETF
SEQ ID NO:21   ----------MQTRKIVRAAAVQAASPNYDLATGVDKTIELARQARDEGCDLIVFGETW
SEQ ID NO:22   ----------MKEPLKVACVQAAPVFLDLDATVDKTITLMEQAAAAGAGLIAFPETW
SEQ ID NO:23   -----LAHPKYKVAVVQAAPAWLDLDASIKKTIALIEEAADKGAKLIAFPEVF
SEQ ID NO:24   ----------MVEYTNTFKVAAVQAQPVWFDAAKTVDKTVSIIAEAARNGCELVAFPEVF
SEQ ID NO:25   ----------MVEYTNTFKVAAVQAQPVWFDAAKTVDKTVSIIAEAARNGCELVAFPEVF
                                  *      .    :                . *:|
```

FIGURE 1A

```
SEQ ID NO:4     IPGYP-----YWAWLGDVKYSLS---FTSRYHENSLELGDDRMRRLQLAARRNKIALVMGYS
SEQ ID NO:5     LPGYP-----FHVWLGAPAWSLK---YSARYYANSLSLDSAEFQRIAQAARTLGIFIALGYS
SEQ ID NO:6     IPGYP-----YHIWVDSPLAGMAK-FAVRYHENSLTMDSPHVQRLLDAARDHNIAVVVGIS
SEQ ID NO:7     IPGYP-----YWAWIGDVKWAVSD-FIPKYHENSLTLGDDRMRRLQLAARQNNIALVMGYS
SEQ ID NO:8     IPGYP-----YWAWIGDVKWAVSE-FIPKYHENSLTLGDDRMRRLQLAARQHNIAMVVGYS
SEQ ID NO:9     VGGYPKGADFHIFLGGRTPQGRA-QYQRYAETAIAVPGPVTERIGQIAAEQDMFIVVGVI
SEQ ID NO:10    IGGYPRGFRFGLGVGVHNEEGRD-EFRKYHASAIKVPGPEVEKLAELAGKNNVYLVMGAI
SEQ ID NO:11    LPGYP-----YFSFVEPPVLMGRS--HLKLYEQAFTMTGPELQQIARAARQHRLFVLLGVN
SEQ ID NO:12    LPGYP-----YFSFVEPPVLMGRS--HLKLYEQAFTMTGPELQQIARAARQHRLFVLLGVN
SEQ ID NO:13    VPYYP-----YFSFVEPPVLMGKS--HLKLYQEAVTVPGKVTQAIAQAAKTHGMVVVLGVN
SEQ ID NO:14    LGGYPKGEGFGTQLGYRLPEGRE-AFARYFANAIDVPGSETAALAGLSARTGASLVLGVI
SEQ ID NO:15    IGGYPKGLDFGARMGTRTEAGRE-DFLRYWKAAIDVPGKETARIGSFAAKMKAYLVVGVI
SEQ ID NO:16    IPGYP-----WWIWLGNADYGMK---YYIQLYKNSVEIPSLAVQKLSSAG-TNKVYFCVSVT
SEQ ID NO:17    IPGYP-----YWIWTSNMDFTGM---MWAVLFKNAIEIPSKEVQQISDAAKKNGVYVCVSVS
SEQ ID NO:18    LPGYP-----YFSFVEPPVLMGRS--HLALYEQAVVVPGPVTDAVAAAASQYGMQVLLGVN
SEQ ID NO:19    LGGYPKGEGFGTQLGYRLPEGRE-AFARYFANAIEVPGVETDALAALSARTGANLVLGVI
SEQ ID NO:20    VPGYP-----WWLWLDSPAWGMQ---FVARYFDNSLALDGPLFARLREAARRSAITVVTGHS
SEQ ID NO:21    LPGYP-----FHVWLGAPAWSLK---YSARYYANSLSLDSAEFQRIAQAARTLGIFIALGYS
SEQ ID NO:22    LPGYP-----WFLWLDAPAWNMP---LVQRYHQQSLVLDSVQARRISDAARHLGLYVVLGYS
SEQ ID NO:23    IPGYP-----WHIWMDSPAWCIGRGFVQRYFDNSLAYDSPQAEALRAAVRKAQLTAVLGLS
SEQ ID NO:24    IPGYP-----YHIWVDSPLAGMAK-FAVRYHENSLTMDSPHVQRLLDAARDHNIAVVVGIS
SEQ ID NO:25    IPGYP-----YHIWVDSPLAGMAK-FAVRYHENSLTMDSPHVQRLLDAARDHNIAVVVGIS
                  **                                                    ..    ..           .   ..        .
```

FIGURE 1B

```
SEQ ID NO:4   EREAGSRYLSQVFIDERGEIVANRRKLKPTHVERTIYGEGNGTDFLTHDFA-FGRVGGLN
SEQ ID NO:5   ERSGGSLYLGQCLIDDKGQMLWSRRKLKPTHVERTVFGEGYARDLIVSDTE-LGRVSALC
SEQ ID NO:6   ERDGGSLYMTQLVIDADGQLVARRRKLKPTHVERSVYGEGNGSDISVYDMP-FARLSALN
SEQ ID NO:7   EKDGASRYLSQVFIDQNGDIVANRRKLKPTHVERTIYGEGNGTDFLTHDFG-FGRVGGLN
SEQ ID NO:8   EKDGASRYLSQVFIDQNGDIVANRRKLKPTHVERTIYGEGNGTDFLTHDFG-FGRVGGLN
SEQ ID NO:9   ERDGGTLYCTILFFSPEGELLGKHRKLMPTALERLLMGYGDGSTFPVYDTP-LGKLGAVV
SEQ ID NO:10  EKDGYTLYCTALFFSPQGQFLGKHRKLMPTSLERCIWGQGDGSTIPVYDTP-IGKLGAAI
SEQ ID NO:11  ERDGGSLYNTQLLISDQGDLLLKRRKITPTYHERMVWGQGGAGLTVVETV-LGKVGALA
SEQ ID NO:12  ERDGGSLYNTQLLISDQGDLLLKRRKITPTYHERMVWGQGGAGLTVVETV-LGKVGALA
SEQ ID NO:13  ERDGGSLYNTQLIFDADGAIVLKRRKITPTYHERMVWGQGDGAGLRTVDTT-VGRLGALA
SEQ ID NO:14  EREEGSLYNTQLIFFEPEGGIVAKHRKLMPTGTERLIWGKGDGSTLPVVDGR-AGRISAAV
SEQ ID NO:15  ERSGNTLYCTVLFFAPDGTLIGKHRKLMPTATERLVWGQGDGSTIEILDTA-VGKLGAAI
SEQ ID NO:16  ERSEATLYCTALFFAPDGTLIGKHRKLMPTATERLVWGQGDGSTIEILDTA-VGKLGAAI
SEQ ID NO:17  EKDGGSLYLTQLWFDPNGDLIGKHRKLKATNAEKTIWGDGDGSMMPVFETE-FGNLGGLQ
SEQ ID NO:18  EKDNASLYLTQLWFDPNGNLIGKHRKFKPTSSERAVWGDGDGSMAPVFKTE-YGNLGGLQ
SEQ ID NO:19  ERDGGTLYNTQLLFNSCGELVLKRRKITPTYHERMVWGQGDGSGLKVVQTP-LARVGALA
SEQ ID NO:20  ERSGSTLYCTALYFDPQQGLSGKHRKLMPTGTERLIWGKGDGSTLPVLDTQ-VGRVGAVI
SEQ ID NO:21  ERSGGSLYLGQCLIDDKGEMLWSRRKLKPTHVERTVFGESDGSNLTVVDTE-LGRLGALC
SEQ ID NO:22  ERNKASLYIGQWIIDDHGETVGVRRKLKATHVERTMFGEGDGASLRTFETP-VGVLGALC
SEQ ID NO:23  ERDGGSLYIAQWLIGADGETIAKRRRKLRPTHAERTVYGEGDGSDLAVHERPDIGRISALC
SEQ ID NO:24  ERDGGSLYMTQLIIDADGQIVARRRKLKPTHVERSVYGEGNGSDISVYDMP-FARLSALN
SEQ ID NO:25  ERDGGSLYMTQLIIDADGQIVARRRKLKPTHVERSVYGEGNGSDISVYDMP-FARLSALN
              *  ::   *              :*.: * ** : .  :     .           ::
```

FIGURE 1C

```
SEQ ID NO:4   CWEHFQPESKFMMYSLGEQVHVASWPAMSPLQPDVFQLSIEANATV------TRSYAIE
SEQ ID NO:5   CWEHLSPESKYALYSQHEAIHIAAWPSFSLYSEQAHALSAKVNMAA------SQIYSVE
SEQ ID NO:6   CWEHFQTETKYAMYSMHEQVHVASWPGMSLYQPEVPAFGVDAQLTA------TRMYALE
SEQ ID NO:7   CWEHFQPESKYMMYSLNEQIHVASWPAMFALTPDVHQLSVEANDTV------TRSYAIE
SEQ ID NO:8   CWEHFQPESKYMMYSLNEQIHVASWPAMFALTPDVHQLSVEANDTV------TRSYAIE
SEQ ID NO:9   CWENYMPELRMAMYGKQIQIYCAPTADDKPTWVSTMQ---------------HVALE
SEQ ID NO:10  CWENRMPEYRTALYAKGIELYCAPTADGSKEWQSSML---------------HIAIE
SEQ ID NO:11  CWENYNPELARFSLMTQGEEIHCAQFPGSLVGPIFSEQTAVT----------LRHHALE
SEQ ID NO:12  CWENYNEELARFSLMTQGEEIHCAQFPGSLVGPIFSEQTAVT----------LRHHALE
SEQ ID NO:13  CWENYNPELARYALMAQHEQIHCGQFPGSMVGQIFADQMEVT----------MRHHALE
SEQ ID NO:14  CWENYMPELRTAMYAKGVQLWCAPTVDERELWQVSMR---------------HVAAE
SEQ ID NO:15  CWENYMPVLRQVMYAGGVNIWCAPTVDQREIWQVSMR---------------HIAYE
SEQ ID NO:16  CWEHFTLPENVAAMASMNEQVHVASWPIGMPQ--EGHLFGPEQCVTA-----TKYAIS
SEQ ID NO:17  CWEHALPENIAAMGSLNEQVHVASWPAFVPKGAVSSRVSSSVCASTNAMHQIISQFYAIS
SEQ ID NO:18  CWENYNPEARYALMAQGEEIHCAQFPGSLVGPIFTEQTAVT-----------MRHHALE
SEQ ID NO:19  CWENMMPELRTAMYAQGIEVWCAPTVDEREMWQVSMR---------------HIAHE
SEQ ID NO:20  CWEHLQPETKYAMYSQHEQIHVAAWPSFSVYRGAAYALGPEVNTGA------ARQYAVE
SEQ ID NO:21  CWEHLSPESKYALYSQHEAIHIAAWPSFSLYSEQAHALSAKVNMAA------SQIYSVE
SEQ ID NO:22  CWEHLQPESKYAMYAQNEQIHVAAWPSFSLYRNATSALGPEVNTAA------SRVYAAE
SEQ ID NO:23  CWEHLQPESKYAMYAQNEQIHVAAWPSFSLYDPFAPALGAEVNNAA------SRVYAVE
SEQ ID NO:24  CWEHFQPETKYAMYSMHEQVHVASWPGMSLYQPEVPAFGVDAQLTA------TRMYALE
SEQ ID NO:25  CWEHFQTETKYAMYSMHEQVHVASWPGMSLYQPEVPAFGVDAQLTA------TRMYALE
              ***  *                                              ..
```

FIGURE 1D

```
SEQ ID NO:4   GQTFVLCSTQVIG----PSAIETFCLNDE--QRALLPQGCGWARIYGPDGSELAKPLAED
SEQ ID NO:5   GQCFTIAASSVVT----QETLDMLEVGEH--NASLLKVGGGSSMIFAPDGRTLAPYLPHD
SEQ ID NO:6   GQTFVVCTTQVVT----PEAHEFFCDNDE--QRKLIGRGGGFARIIGPDGRDLATPLAED
SEQ ID NO:7   GQTFVLASTHVIG----KATQDLFAGDDDA-KRALLPLGQWARIYGPDGKSLAEPLPED
SEQ ID NO:8   GQTFVLAATHVIG----KATQDLFAGDDEA-KRALLPLGQWARIYGPDGKSLAEPLAEN
SEQ ID NO:9   GRCFVLSACQHLRGKDFPPEFHNALDVQP--DTVLMRGGSCIVDPMGQLLAGPVY-D
SEQ ID NO:10  GGCFVLSACQFCLRKDFPDHPDYLFTDWYDDKEPDSIVSQGGSVIISPLGQVLAGPNF-E
SEQ ID NO:11  AGCFVLSSTAWLD----PADYDTITPDRS--LHKAFQGGCHTAIISPEGRYLAGPLP-E
SEQ ID NO:12  AGCFVLSSTAWLD----PADYDTITPDRS--LHKAFQGGCHTAIISPEGRYLAGPLP-E
SEQ ID NO:13  SGCFVINATGWLT----AEQKLQITTDEK--MHQALSGGCYTAIISPEGKHLCEPIA-E
SEQ ID NO:14  GRCFVISACQVQ-----DSPAALGMEVANWPA-ERPLINGGSLIVGPLGDVLAGPLL-G
SEQ ID NO:15  GRLFVLSACQYMTRADAPADYDCIQGNDP--ETELIAGGSVIIDPMGNILAGPLY-G
SEQ ID NO:16  NQVFCLLSSQIWT----EEQRDKICETEE--QRNFMKVGHGFSKIIAPNGMEIGNKLAHD
SEQ ID NO:17  NQVYVIMSTNLVG----QDMIDMIGKDEF--SKNFLPLGSGNTAIISNTG-EILASIPQD
SEQ ID NO:18  AGCFVICSTGWLH----PDDYASITSESG--LHKAFQGGCHTAVISPEGRYLAGPLP-D
SEQ ID NO:19  GRCFVVSACQVQ-----ASPEELGLEIANWPA-QRPLIAGGSVIVGPMGDVLAGPLV-G
SEQ ID NO:20  GQCFVLSPCAVID----EAGVELFCDTPA--KRELLLPGGGFAQIYGPDGRELGTALPET
SEQ ID NO:21  GQCFTIAASSVVT----QETLDMLEVGEH--NAPLLKVGGGSSMIFAPDGRTLAPYLPHD
SEQ ID NO:22  GQCFVLAPCAIVS----PEMIEMLCDSDA--KRSLLQAGGGHARIFGPDGSDLATPLGEH
SEQ ID NO:23  GSCFVLAPCATVS----QAMIDELCDRPD--KHALLHAGGGHAAIFGPDGSALAAQLPPD
SEQ ID NO:24  GQTFVVCTTQVVT----PEAHEFFCENEE--QRKLIGRGGGFARIIGPDGRDLATPLAED
SEQ ID NO:25  GQTFVVCTTQVVT----PEAHEFFCENEE--QRMLIGRGGGFARIIGPDGRDLATPLAED
                   ..                              ..            *  ..
```

FIGURE 1E

```
SEQ ID NO:4   AEGILYAEIDLEQILLAKAGADPVGHYSRPDVLSVQFDPRNHTPVHRIGIDGRLDVNTRS
SEQ ID NO:5   AEGLIIADLNMEEIAFAKAINDPVGHYSKPEATRLVLDLGHREPMTRVHSK------SVIQEE
SEQ ID NO:6   EEGILYADIDLSAITLAKQAADPVGHYSRPDVLSLNFNQRHTTPVN------TAISTI
SEQ ID NO:7   AEGLLYAELDLEQIILAKAAADPAGHYSRPDVLSLKIDTRNHTPVQYITADGRTSLNSNS
SEQ ID NO:8   AEGLLYAELDLEQIIVAKAAADPAGHYSRPDVLSLKVDTRNHTPVQYVTEDGGSSLNSNS
SEQ ID NO:9   EDAILVADIDLDAVTRGKMDFDVVGHYARPDIFSLTVDERPKPPVTTL----------K
SEQ ID NO:10  SEGLITADLDLGDVARAKLYFDSVGHYSRPDVLHLTVNEHPKKPVTFI----------S
SEQ ID NO:11  GEGLAIAELDKSLITKRKRMMDSVGHYSRPDLLSLRINRSPATQVQAIG---------S
SEQ ID NO:12  GEGLAIAELDKSLITKRKRMMDSVGHYSRPDLLSLRINRSPATQVQAIG---------S
SEQ ID NO:13  GEGLAIADLDFSLIAKRKRMMDSVGHYARPDLLQLTLNNQPWSALEAN----------P
SEQ ID NO:14  ARGLVCAEVDTDELVRARYDFDVVGHYARPDVFELSVDERPRPGVR------------F
SEQ ID NO:15  QEGVLVADIDLSDTIKARYDLDVSGHYGRPDIFEIKVDRQSHQVITDQ----------F
SEQ ID NO:16  EEGITYADIDLEQIIPGKFLIDSAGHYSTPGFLSLSFDRTEKKPIKHIG---------E
SEQ ID NO:17  AEGIAVAEIDLNQIIYGKWLLDPAGHYSTPGFLSLTFDQSEHVPVKKIG---------E
SEQ ID NO:18  GEGLAIADLDLALITKRKRMMDSVGHYSRPELLSLQINSSPAVPVQNM----------S
SEQ ID NO:19  RAGLISAQIDTADLVRARYDVVGHYARPDVFELTVDQRPRPGVR--------------F
SEQ ID NO:20  EEGLVYADLEASAVAKSAADPVGHYSRPDVLQLLWDP-----RPRSVVR---------Q
SEQ ID NO:21  AEGLIIADLNMEEIAFAKAINDPVGHYSKPEATRLVLDLGHRDPMTRVHSK---SVTREE
SEQ ID NO:22  EEGLLYATLDPAALTLAKVAADPAGHYSRPDVTRLMFNP-------NPTPCVV------D
SEQ ID NO:23  QEGLLIAEIDLGMIGIAKNAADPAGHYSRPDVTRLLLNK------KPLNRVE-------H
SEQ ID NO:24  EEGILYADIDLSAITLAKQAADPVGHYSRPDVLSLNFNQRRTTPVN--------TPLSTI
SEQ ID NO:25  EEGILYADIDLSAITLAKQAADPVGHYSRPDVLSLNFNQRRTTPVN--------TPLSTI
                *  :  :         *      ***.  *    .         ::
```

FIGURE 1F

| | |
|---|---|
| SEQ ID NO:4 | RVENFRLRQAAEQERQASKRLGTKLFEQS----------------LLAEEPVPAK--- |
| SEQ ID NO:5 | APEPHVQSTAAPVAVSQTQDSDTLLVQEPS--------------------------- |
| SEQ ID NO:6 | HATHTLVPQSGALDGVRELNGADEQRALPS---------------THSDETDRATASI |
| SEQ ID NO:7 | RVENYRLHQLADIEKYENAEAATLPLDAPAPAP------------APEQKSGRAKAEA |
| SEQ ID NO:8 | RVENYRLRQLADIEKYENADSATVPLDVTTPEKQSGDVNANGNAKVNTNPSAKAKA |
| SEQ ID NO:9 | P-------------------------------------------------------- |
| SEQ ID NO:10 | KVEKAEDDSNK--------------------------------------------- |
| SEQ ID NO:11 | AAALPELPNLEAAPAETAEDYLHA-------------------------------- |
| SEQ ID NO:12 | AAALPELPNLEAAPAETAEDYLHA-------------------------------- |
| SEQ ID NO:13 | VTPNAIPAVSDPELTETIEALPNNPIFSH--------------------------- |
| SEQ ID NO:14 | IG------------------------------------------------------ |
| SEQ ID NO:15 | SRDQATEKKPVSDSEISQLD------------------------------------ |
| SEQ ID NO:16 | SAQETVTYEEIQYGNKANVKVHS--------------------------------- |
| SEQ ID NO:17 | QTNHFISYEDLHEDKMDMLTIPPRRVATA--------------------------- |
| SEQ ID NO:18 | TASVPLEPATATDALSSMEALNHV-------------------------------- |
| SEQ ID NO:19 | T------------------------------------------------------- |
| SEQ ID NO:20 | VA-LSVASPAESAD---------DAEPAVR-------------------------- |
| SEQ ID NO:21 | APEQGVQSKIASVAISHPQDSDTLLVQEPS-------------------------- |
| SEQ ID NO:22 | LPDLPISSESIELL-----RPDIALEV----------------------------- |
| SEQ ID NO:23 | FS-LPVDSAAAALPGEAAVARPDQSI------------------------------ |
| SEQ ID NO:24 | HATHTFVPQFGALDGVRELNGADEQRALPS---------------THSDETDRATATL |
| SEQ ID NO:25 | HATHTFVPQFGALDGVRELNGADEQRALPS---------------THSDETDRATATL |

FIGURE 1G

US 7,867,748 B2

IMMOBILIZED MICROBIAL NITRILASE FOR PRODUCTION OF GLYCOLIC ACID

FIELD OF THE INVENTION

This invention relates to the field of organic acid synthesis and microbiology. More specifically, a process is provided to improve the specific activity of a dehydrated enzyme catalyst having nitrilase activity for hydrolysis of glycolonitrile to glycolic acid upon rehydration. In particular, a process is provided for pretreating an enzyme catalyst having nitrilase activity with glutaraldehyde, immobilizing the gutaraldehyde-preteated cells and chemically cross-linking the immobilized cells prior to dehydration. Upon rehydration, the enzyme catalyst exhibits improved specific nitrilase activity as compared to enzyme catalysts having nitrilase activity that are dehydrated and rehydrated without said processing.

BACKGROUND OF THE INVENTION

Glycolic acid ($HOCH_2COOH$; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, as a monomer in the preparation of polyglycolic acid (PGA), and as a component in personal care products. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). It has also been reported that polyglycolic acid is useful as a gas barrier material (i.e., exhibits high oxygen barrier characteristics) for packing foods and carbonated drinks (WO 2005/106005 A1). However, traditional chemical synthesis of glycolic acid produces a significant amount of impurities that must be removed prior to use. New technology to commercially produce glycolic acid, especially one that produces glycolic acid in high purity and at low cost, would be eagerly received by industry.

Microbial enzyme catalysts can hydrolyze a nitrile (e.g., glycolonitrile) directly to the corresponding carboxylic acids (e.g., glycolic acid) using a nitrilase (EC 3.5.5.7), where there is no intermediate production of the corresponding amide (Equation 1), or by a combination of nitrile hydratase (EC 4.2.1.84) and amidase (EC 3.5.1.4) enzymes, where a nitrile hydratase (NHase) initially converts a nitrile to an amide, and then the amide is subsequently converted by the amidase to the corresponding carboxylic acid (Equation 2):

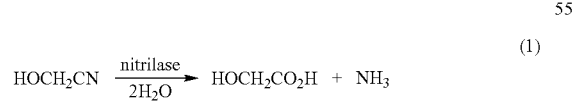
(1)

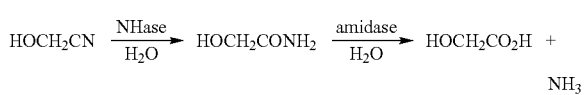
(2)

Enzymatic hydrolysis of nitriles to glycolic acid for commercial purposes requires production of the enzyme catalyst in high-volume by fermentation. Much of the volume is attributable to the water content of the fermentation broth. Because of said high-volume fermentation broth, storing, and in many cases transporting the fermentation broth comprising the enzyme catalyst, poses both logistical and economic issues. A mechanism for providing ease in storage and transportation of the enzyme catalyst is to isolate the enzyme catalyst from the fermentation broth, immobilize the enzyme catalyst (for example, by entrapment in carrageenan gel), and dehydration of the immobilized enzyme catalyst. The immobilized enzyme catalyst may be rehydrated prior to use for glycolic acid production. However, dehydration and rehydration often result in significant loss in enzyme activity.

The dehydration or drying of immobilized cell catalysts has been previously described. U.S. Pat. No. 5,998,180 describes a process for the production of a dried, immobilized microbial nitrilase, where the *Rhodococcus rhodochrous* NCIMB 40757 or NCIMB 408333 cells containing said nitrilase retain at least 80% of their initial activity after immobilization in cross-linked polyacrylamide beads, and where the resulting immobilized cell nitrilase retains at least 90% of its initial immobilized activity after the cross-linked polyacrylamide beads are dried to 12% moisture at 60° C. B. DeGiulio et al (World J. Microbial. Biotechnol. 21:739-746, (2005)) describe the immobilization of lactic acid bacteria in calcium alginate, followed by freeze-drying of the resulting immobilized cell catalyst, where at least 72% of the cells retained metabolic activity after freeze-drying. U.S. Pat. No. 5,846,762 describes the dehydration of gelatin beads containing covalently-immobilized cellobiase, and states in column 6, lines 9-11, that calcium alginate and kappa-carrageenan beads, once dehydrated, generally cannot be rehydrated.

None of the methods described immediately above for dehydration or freeze-drying of immobilized enzyme catalysts and subsequent rehydration report an improvement in recovered enzyme activity after rehydration, or improvement in the stability of enzyme activity when the resulting rehydrated enzyme catalyst is employed in a reaction to convert substrate to product, when compared to a comparable rehydrated immobilized enzyme catalyst that was not prepared with glutaraldehyde-pretreated cells.

In addition to loss of enzyme catalyst activity as a result of enzyme catalyst processing, such as in the case of dehydration/rehydration, enzymatic hydrolysis of glycolonitrile to glycolic acid typically requires a substantially pure form of glycolonitrile. Methods to synthesize glycolonitrile by reacting aqueous solutions of formaldehyde and hydrogen cyanide have previously been reported (U.S. Pat. Nos. 2,175,805; 2,890,238; and 5,187,301; Equation 3).

(3)

However, these methods typically result in an aqueous glycolonitrile reaction product that requires significant purification (e.g., distillative purification) as many of the impurities and/or byproducts of the reaction (including excess reactive formaldehyde) may interfere with the enzymatic conversion of glycolonitrile to glycolic acid, including suppression of catalyst activity (i.e., decreased specific activity). In particular, it is well known that formaldehyde can create undesirable modifications in proteins by reacting with amino groups from N-terminal amino acid residues and the side chains of arginine, cysteine, histidine, and lysine residues (Metz et al., *J. Biol. Chem.*, 279 (8): 6235-6243 (2004)).

Suppression of catalyst activity decreases the overall productivity of the catalyst (i.e., total grams of glycolic acid formed per gram of catalyst), adding a significant cost to the overall process that may make enzymatic production economically non-viable when compared to chemical synthesis. As such, reaction conditions are needed that can help to protect the enzymatic activity against undesirable impurities that decrease the activity of the catalyst.

A method of producing high purity glycolonitrile has been reported by subjecting the formaldehyde to a heat treatment prior to the glycolonitrile synthesis reaction (U.S. Ser. Nos. 11/314,386 and 11/314,905; Equation 3). However, glycolonitrile can reversibly disassociate into formaldehyde and hydrogen cyanide. As such, there remains a need to protect nitrilase activity against the undesirable effects of both formaldehyde and hydrogen cyanide produced by dissociation of glycolonitrile.

U.S. Pat. No. 5,508,181 also describes similar difficulties related to rapid enzyme catalyst inactivation when converting nitrile compounds to $\alpha$-hydroxy acids. Specifically, U.S. Pat. No. 5,508,181 provides that $\alpha$-hydroxy nitrile compounds partially disassociate into the corresponding aldehydes, according to the disassociation equilibrium. These aldehydes were reported to inactivate the enzyme within a short period of time by binding to the protein, thus making it difficult to obtain $\alpha$-hydroxy acid or $\alpha$-hydroxy amide in a high concentration with high productivity from $\alpha$-hydroxy nitriles (col. 2, lines 16-29). As a solution to prevent enzyme inactivation due to accumulation of aldehydes, phosphate or hypophosphite ions were added to the reaction mixture. Similarly, U.S. Pat. No. 5,326,702 describes the use of sulfite, disulfite, or dithionite ions to sequester aldehyde and prevent enzyme inactivation, but concludes that the concentration of $\alpha$-hydroxy acid produced and accumulated even by using such additives is not sufficient for most commercial purposes.

Moreover, U.S. Pat. No. 6,037,155 teaches that low accumulation of $\alpha$-hydroxy acid product is related to enzyme inactivation within a short time due to the disassociated-aldehyde accumulation. These inventors suggest that enzymatic activity is inhibited in the presence of hydrogen cyanide (Asano at al., *Agricultural Biological Chemistry*, Vol. 46, pages 1165-1174 (1982)) generated in the partial disassociation of the $\alpha$-hydroxy nitrile in water together with the corresponding aldehyde or ketone (Mowry, David T., *Chemical Reviews*, Vol. 42, pages 189-283 (1948)). The inventors address the problem of aldehyde-induced enzyme inactivation by using microorganisms whose enzyme activity could be improved by adding a cyanide substance to the reaction mixture. The addition of a cyanide substance limited the disassociation of $\alpha$-hydroxy nitrile to aldehyde and hydrogen cyanide. While this tactic provides a benefit to the system, it only addresses one aspect associated with enzyme inactivation in conversion of glycolonitrile to glycolic acid, in that, as stated above, glycolonitrile is known to reversibly disassociate to hydrogen cyanide and formaldehyde, and both are known to negatively effect enzyme catalyst activity.

A separate process has been developed to protect the specific activity of an enzyme catalyst having nitrilase activity when converting glycolonitrile to glycolic acid in the presence of formaldehyde (see copending U.S. application Ser. No. 2009-0111162 incorporated herein by reference), where significant improvements in catalyst activity and stability were achieved by adding an amine protectant to the reaction mixture, or by immobilization of the nitrilase catalyst in or on a matrix that is comprised of an amine protectant, e.g. PEI, polyallylamine, PVOH/polyvinylamine, etc. In that system, the specific activity of the catalyst in the presence of formaldehyde is improved.

Even though many of the above means improved nitrilase catalyst productivity for glycolic acid, a significant decrease in the initial enzymatic activity of the immobilized microbial nitrilase was still generally observed upon use of said catalyst in reactions for the hydrolysis of glycolonitrile, for example, in consecutive batch reactions with catalyst recycle, or in the initial stage of starting up a continuous stirred tank reaction (CSTR) or a fixed-bed column reactor. The problem of significant loss of initial nitrilase activity during hydrolysis of glycolonitrile was addressed in part by pretreating the microbial catalyst with glutaraldehyde prior to immobilization in carrageenan (as described in U.S. Pat. No. 7,695,945 incorporated herein by reference), where a significantly-greater percentage of the initial immobilized microbial nitrilase specific activity ($\mu$moles of glycolonitrile hydrolyzed per minute per gram of catalyst) was retained during the hydrolysis of glycolonitrile to glycolic acid (as the ammonium salt).

U.S. Pat. No. 4,288,552 discloses (column 1, lines 46-49, and column 2, lines 50-55) that glutaraldehyde-sensitive enzymes (such as thiol-enzymes (e.g., nitrilase) and others with an SH group in or very near the active site of the enzyme molecule) are inactivated by thiol-reactive agents such as glutaraldehyde. Therefore, it was not only unpredictable that pretreatment of an enzyme catalyst having nitrilase activity with glutaraldehyde would not result in a significant decrease in microbial nitrilase activity prior to immobilization, but surprisingly, the glutaraldehyde pretreatment was found to benefit enzyme catalyst activity, particularly when the immobilized enzyme catalyst was dehydrated, and subsequently rehydrated prior to use for the hydrolysis of glycolonitrile to glycolic acid. The process of the present invention prevents a significant loss of activity during the dehydration/rehydration steps, and results in a rehydrated immobilized enzyme catalyst with an initial activity and subsequent stability of enzyme catalyst activity during the subsequent used of the rehydrated immobilized enzyme activity for the conversion of glycolonitrile to glycolic acid. This benefit is incorporated into the process described herein which provides for addressing the need for a commercial process, including a dehydration step, for producing an enzyme catalyst having improved specific activity for glycolic acid production upon rehydration.

Therefore, the problem to be solved is the need for a commercially viable process for producing an enzyme catalyst having nitrilase activity for hydrolysis of glycolonitrile to glycolic acid with improved specific activity. More specifically, there is a need for a commercially acceptable process for using an enzyme catalyst having nitrilase activity for the hydrolysis of glycolonitrile to glycolic acid that minimizes loss in enzyme activity resulting from dehydration and rehydration prior to use and resulting from inactivation by impurities or dissociation of reactants.

SUMMARY OF THE INVENTION

The present problems have been solved by providing a process for producing a dehydrated immobilized enzyme catalyst having improved specific activity upon rehydration and use of said enzyme catalyst for the conversion of glycolonitrile to glycolic acid, said process comprising:
  (a) producing an enzyme catalyst having nitrilase activity by fermentation;
  (b) pretreating said enzyme catalyst with glutaraldehyde;
  (c) optionally inactivating unreacted glutaraldehyde with bisulfate following glutaraldehyde pretreatment;

(d) recovering the enzyme catalyst from (b) or (c) and immobilizing the said enzyme catalyst in carrageenan;
(e) cross-linking the resulting carrageenan-immobilized enzyme catalyst of (d) with glutaraldehyde and polyethylenimine; and
(f) dehydrating the cross-linked immobilized enzyme catalyst produced in step (e).

A further aspect of the invention is rehydrating the dehydrated immobilized catalyst of step (f) above, in an aqueous solution. And further, contacting said rehydrated enzyme catalyst with glycolonitrile in an aqueous solution, whereby glycolic acid is produced. In a further aspect, the glycolic acid is recovered from said aqueous solution.

The immobilized enzyme catalyst that is produced by the process of steps a) through f) above, retains a significantly-greater percentage of its initial specific activity (μmoles of glycolonitrile hydrolyzed per minute per gram of catalyst) when compared to an immobilized enzyme catalyst prepared without glutaraldehyde pretreatement of the enzyme catalyst prior to immobilization, crosslinking, dehydration and rehydration, when used for the conversion of glycolonitrile to glycolic acid (as the ammonium salt).

Another aspect of the invention is directed to the dehydrated enzyme catalyst as an improved enzyme catalyst having nitrilase activity. Said dehydrated enzyme catalyst retains at least about 70%, at least about 75%, at least about 80%, at least about 85%, or at least about 90% of its specific activity after rehydration.

BRIEF DESCRIPTION OF THE FIGURE, SEQUENCE LISTING AND THE BIOLOGICAL DEPOSITS

The invention can be more fully understood from the FIGURE, sequence listing, the biological deposits, and the detailed description that together form this application.

FIGURE

FIG. 1, panels A-G, is a CLUSTALW alignment (version 1.83 using default parameters) of various nitrilase sequences. The conserved catalyst signature sequence surrounding the catalyst cysteine residue is highlighted in gray shading. The amino acids representing the catalytic triad (Glu$_{48}$, Lys$_{130}$, and Cys$_{164}$; numbering based on the amino acid sequence SEQ ID NO: 4) are underlined.

SEQUENCE LISTING

The following sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO: 1 is the amino acid sequence of the catalytic signature motif encompassing the essential cysteine residue of nitrilase enzymes (Formula 1).

SEQ ID NO: 2 is the amino acid sequence of a preferred catalyst signature motif encompassing the essential cysteine residue of nitrilase enzymes (Formula 2).

SEQ ID NO: 3 is the nucleotide sequence of the *Acidovorax facilis* 72W nitrilase coding sequence comprising a change in the start codon from TTG to ATG to facilitate recombinant expression in *E. coli*.

SEQ ID NO: 4 is the deduced amino add sequence of the *Acidovorax facilis* 72W nitrilase (ATCC 55746).

SEQ ID NO: 5 is the amino acid sequence of the *Alcaligenes faecalis* JM3 nitrilase (GENBANK® BAA02684.1).

SEQ ID NO: 6 is the amino acid sequence of the *Rhodococcus rhodochrous* J1 nitrilase (GENBANK® Q03217).

SEQ ID NO: 7 is the amino acid sequence of the *Rhodococcus rhodochrous* K22 nitrilase (GENBANK® Q02068).

SEQ ID NO: 8 is the amino acid sequence of the *Nocardia* sp. C-14-1 nitrilase (GENBANK® AAX18182.1).

SEQ ID NO: 9 is the amino acid sequence of the *Bordetella bronchiseptica* RB50 nitrilase (GENBANK® NP_887662.1).

SEQ ID NO: 10 is the amino acid sequence of the *Arabidopsis thaliana* nitrilase (GENBANK® AAB60275.1 and AAA19627.1).

SEQ ID NO: 11 is the amino acid sequence of the *Synechococcus elongatus* PCC 7942 nitrilase (GENBANK® YP_399857.1).

SEQ ID NO: 12 is the amino acid sequence of the *Synechococcus elongatus* PCC 6301 nitrilase (GENBANK® YP_171411.1).

SEQ ID NO: 13 is the amino acid sequence of the *Synechocystis* sp. PCC 6803 nitrilase (GENBANK® NP_442646.1).

SEQ ID NO: 14 is the amino acid sequence of the *Pseudomonas entomophila* L48 nitrilase (GENBANK® YP_6090481.1).

SEQ ID NO: 15 is the amino acid sequence of the *Zymomonas moblis* nitrilase (GENBANK® YP_162942.1).

SEQ ID NO: 16 is the amino acid sequence of the *Bacillus* sp. OxB-1 nitrilase (GENBANK® BAA90460.1).

SEQ ID NO: 17 is the amino acid sequence of the *Comamonas testosteroni* nitrilase (GENBANK® AAA82085.1).

SEQ ID NO: 18 is the amino acid sequence of the *Synechococcus* sp. CC9605 nitrilase (GENBANK® YP_381420.1).

SEQ ID NO: 19 is the amino acid sequence of the *Pseudomonas fluorescens* Pf-5 nitrilase (GENBANK® YP_260015.1).

SEQ ID NO: 20 is the amino acid sequence of the *Nocardia farcinica* IFM 10152 nitrilase (GENBANK® YP_119480.1).

SEQ ID NO: 21 is the amino acid sequence of the *Alcaligenes faecalis* 1650 nitrilase (GENBANK® AAY06506.1).

SEQ ID NO: 22 is the amino acid sequence of the *Pseudomonas syringae* pv. *syringae* B728a nitrilase (GENBANK® AAY35081.1).

SEQ ID NO: 23 is the amino acid sequence of the *Bradyrhizobium* sp. BTAII nitrilase (GENBANK® ZP_00859948.1).

SEQ ID NO: 24 is the amino acid sequence of the *Rhodococcus rhodochrous*

NCIMB 11216 nitrilase (GENBANK® CAC88237).

SEQ ID NO: 25 is the amino acid sequence of *Rhodococcus rhodochrous* ATCC™ 39484

SEQ ID NO: 26 is the nucleotide sequence of an *A. facilis* 72W nitrilase mutant comprising a codon change which resulted in a single amino acid substitution at residue position 201 (L201Q; Leu→Gln).

SEQ ID NO: 27 is the deduced amino acid sequence of the mutant nitrilase (SEQ ID NO: 26) comprising a single amino acid substitution at residue position 201 (Leu201→Gln) of the *A. facilis* 72W nitrilase.

SEQ ID NO: 28 is the nucleotide sequence of an *A. facilis* 72W nitrilase mutant comprising a codon change which resulted in a single amino acid substitution at residue position 201 (L201A; Leu→Ala).

SEQ ID NO: 29 is the deduced amino acid sequence of the mutant nitrilase (SEQ ID NO: 28) comprising a single amino acid substitution at residue position 201 (Leu201→Ala) of the *A. facilis* 72W nitrilase.

SEQ ID NO: 30 is the nucleotide sequence of an *A. facilis* 72W nitrilase mutant comprising a codon change which resulted in a single amino acid substitution at residue position 201 (L201C; Leu→Cys).

SEQ ID NO: 31 is the deduced amino acid sequence of the mutant nitrilase (SEQ ID NO: 30) comprising a single amino acid substitution at residue position 201 (Leu201→Cys) of the *A. facilis* 72W nitrilase.

SEQ ID NO: 32 is the nucleotide sequence of an *A. facilis* 72W nitrilase mutant comprising a codon change which resulted in a single amino acid substitution at residue position 201 (L201T; Leu→Thr).

SEQ ID NO: 33 is the deduced amino acid sequence of the mutant nitrilase (SEQ ID NO: 32) comprising a single amino acid substitution at residue position 201 (Leu201→Thr) of the *A. facilis* 72W nitrilase.

SEQ ID NO: 34 is the nucleotide sequence of an *A. facilis* 72W nitrilase mutant comprising a codon change which resulted in a single amino acid substitution at residue position 201 (L201G; Leu→Gly).

SEQ ID NO: 35 is the deduced amino acid sequence of the mutant nitrilase (SEQ ID NO: 34) comprising a single amino acid substitution at residue position 201 (Leu201→Gly) of the *A. facilis* 72W nitrilase.

SEQ ID NO: 36 is the nucleotide sequence of an *A. facilis* 72W nitrilase mutant comprising a codon change which resulted in a single amino acid substitution at residue position 201 (L201H; Leu→His).

SEQ ID NO: 37 is the deduced amino acid sequence of the mutant nitrilase (SEQ ID NO: 36) comprising a single amino acid substitution at residue position 201 (Leu201→His) of the *A. facilis* 72W nitrilase.

SEQ ID NO: 38 is the nucleotide sequence of an *A. facilis* 72W nitrilase mutant comprising a codon change which resulted in a single amino acid substitution at residue position 201 (L201K; Leu→Lys).

SEQ ID NO: 39 is the deduced amino acid sequence of the mutant nitrilase (SEQ ID NO: 38) comprising a single amino acid substitution at residue position 201 (Leu201→Lys) of the *A. facilis* 72W nitrilase.

SEQ ID NO: 40 is the nucleotide sequence of an *A. facilis* 72W nitrilase mutant comprising a codon change which resulted in a single amino acid substitution at residue position 201 (L201N; Leu→Asn).

SEQ ID NO: 41 is the deduced amino acid sequence of the mutant nitrilase (SEQ ID NO: 40) comprising a single amino acid substitution at residue position 201 (Leu201→Asn) of the *A. facilis* 72W nitrilase.

SEQ ID NO: 42 is the nucleotide sequence of an *A. facilis* 72W nitrilase mutant comprising a codon change which resulted in a single amino acid substitution at residue position 201 (L201S; Leu→Ser).

SEQ ID NO: 43 is the deduced amino acid sequence of the mutant nitrilase (SEQ ID NO: 42) comprising a single amino acid substitution at residue position 201 (Leu201→Ser) of the *A. facilis* 72W nitrilase.

SEQ ID NO: 44 is the nucleotide sequence of an *A. facilis* 72W nitrilase mutant comprising a codon change which resulted in a single amino acid substitution at residue position 168 (F168K; Phe→Lys).

SEQ ID NO: 45 is the deduced amino acid sequence of the mutant nitrilase (SEQ ID NO: 44) comprising a single amino acid substitution at residue position 168 (Phe168→Lys) of the *A. facilis* 72W nitrilase.

SEQ ID NO: 46 is the nucleotide sequence of an *A. facilis* 72W nitrilase mutant comprising a codon change which resulted in a single amino acid substitution at residue position 168 (F168M; Phe→Met).

SEQ ID NO: 47 is the deduced amino acid sequence of the mutant nitrilase (SEQ ID NO: 46) comprising a single amino acid substitution at residue position 168 (Phe168→Met) of the *A. facilis* 72W nitrilase.

SEQ ID NO: 48 is the nucleotide sequence of an *A. facilis* 72W nitrilase mutant comprising a codon change which resulted in a single amino acid substitution at residue position 168 (F168T; Phe→Thr).

SEQ ID NO: 49 is the deduced amino acid sequence of the mutant nitrilase (SEQ ID NO: 48) comprising a single amino acid substitution at residue position 168 (Phe168→Thr) of the *A. facilis* 72W nitrilase.

SEQ ID NO: 50 is the nucleotide sequence of an *A. facilis* 72W nitrilase mutant comprising a codon change which resulted in a single amino acid substitution at residue position 168 (F168V; Phe→Val).

SEQ ID NO: 51 is the deduced amino acid sequence of the mutant nitrilase (SEQ ID NO:50) comprising a single amino acid substitution at residue position 168 (Phe168→Val) of the *A. facilis* 72W nitrilase.

SEQ ID NO: 52 is the nucleotide sequence of an *A. facilis* 72W nitrilase mutant comprising a codon change which resulted in a single amino acid substitution at residue position 168 (T210A; Thr→Ala).

SEQ ID NO: 53 is the deduced amino acid sequence of the mutant nitrilase (SEQ ID NO: 52) comprising a single amino acid substitution at residue position 210 (Thr210→Ala) of the *A. facilis* 72W nitrilase.

SEQ ID NO: 54 is the nucleotide sequence of an *A. facilis* 72W nitrilase mutant comprising a codon change which resulted in a single amino acid substitution at residue position 168 (T210C; Thr→Cys).

SEQ ID NO: 55 is the deduced amino acid sequence of the mutant nitrilase (SEQ ID NO: 54) comprising a single amino acid substitution at residue position 210 (Thr210→Cys) of the *A. facilis* 72W nitrilase.

SEQ ID NO: 56 is the nucleotide sequence of the *A. facilis* 72W nitrilase expressed in *E. coli* strain SS1001 (ATCC PTA-1177).

SEQ ID NO: 57 is the deduced amino acid sequence of the mutant *A. facilis* 72W nitrilase expressed in *E. coli* SS1001 (ATCC PTA-1177).

BIOLOGICAL DEPOSITS

The following biological deposits have been made under the terms of the Budapest Treaty on the International Recognition of the Deposit of Microorganisms for the Purposes of Patent Procedure:

| Depositor Identification Reference | Int'l. Depository Designation | Date of Deposit |
| --- | --- | --- |
| *Acidovorax facilis* 72W | ATCC 55746 | Mar. 8, 1996 |
| *E. coli* SS1001 | ATCC PTA-1177 | Jan. 11, 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

A process is provided to improve the specific activity of a dehydrated immobilized and cross-linked enzyme catalyst having nitrilase activity for hydrolysis of glycolonitrile to glycolic acid upon rehydration. In particular, a process is provided for pretreating an enzyme catalyst having nitrilase activity with glutaraldehyde, immobilizing the gutaraldehyde-preteated cells and chemically cross-linking the immobilized cells prior to dehydration. Upon rehydration, the glutaraldehyde-pretreated immobilized and cross-linked enzyme catalyst exhibits improved specific nitrilase activity as compared to immobilized and cross-linked enzyme catalysts having nitrilase activity that are dehydrated and rehydrated without said processing.

DEFINITIONS

In this disclosure, a number of terms and abbreviations are used.

The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the term "glycolonitrile" is abbreviated as "GLN" and is synonymous with hydroxyacetonitrile, 2-hydroxyacetonitrile, hydroxymethylnitrile, and all other synonyms of CAS Registry Number 107-16-4.

As used herein, the term "glycolic acid" is abbreviated as "GLA" and is synonymous with hydroxyacetic acid, hydroxyethanoic acid, and all other synonyms of CAS Registry Number 79-14-1. The glycolic acid produced by the present processes may in the form of the protonated carboxylic acid and/or the corresponding ammonium salt.

As used herein, the term "ammonium glycolate" is abbreviated "$NH_4GLA$".

As used herein, the term "glycolamide" is the amide derived from the reaction of ammonia with glycolic acid and refers to all other synonyms of compounds having CAS Registry Number 598-42-5.

As used herein, the term "glycolide" refers to the compound of CAS Registry Number 502-97-6.

As used herein, the term "formaldehyde" is abbreviated as "FA" and is synonymous with formic aldehyde, methyl aldehyde, oxomethane, and all other synonyms of CAS Registry Number 50-00-0. Commercially available formaldehyde is typically comprised of a mixture of monomeric formaldehyde ("free formaldehyde") and various oligomers of formaldehyde along with some methanol (typically about 1 wt % to about 15 wt %).

As used herein, the term "hydrogen cyanide" is synonymous with prussic acid, hydrocyanic acid, and all other synonyms of CAS Registry Number 200-821-6.

As used herein, the term "glutaraldehyde" is abbreviated "GA" and is synonymous with pentanedial, 1,5-pentanedial, 1,5-pentanedione, diglutaric aldehyde, glutaral, glutardialdehyde, glutaric acid dialdehyde, glutaric dialdehyde, and all other synonyms of CAS Registry Number 111-30-8.

As used herein, the term "bisulfite" or "sodium bisulfite" is synonymous with sulfurous acid sodium salt, sulfurous acid monosodium salt, hydrogen sodium sulfite, hydrogen sulfite sodium, monosodium sulfite, sodium acid sulfite, sodium bisulfite, sodium bisulphate, sodium hydrogen sulfite, sodium sulfite ($NaHSO_3$), and all other synonyms of CAS Registry Number 7631-90-5.

As used herein, the term "recovering" means isolating, purifying, or transferring the product formed by the present process. Methods to isolate and purify the product(s) from the reaction mixture are well known in the art may include, but are not limited to selective precipitation, crystallization, filtration, reactive solvent extraction, ion exchange, electrodialysis, polymerization, distillation, thermal decomposition, alcoholysis, column chromatography, and combinations thereof. In one embodiment, the term "recovering" may also include transferring the product mixture (typically after filtering out the enzyme catalyst) to another reaction to create one or more additional products. In a preferred embodiment, ion exchange is used to recover the glycolic acid.

As used herein, the terms "enzyme catalyst", "nitrilase catalyst" or "microbial cell catalyst" refers to a catalyst that is characterized by a nitrilase activity (i.e., comprises at least one polypeptide having nitrilase activity) for converting glycolonitrile to glycolic acid and ammonia. A nitrilase enzyme directly converts a nitrile (preferably, an aliphatic nitrile) to the corresponding carboxylic acid, without forming the corresponding amide as intermediate (see Equation 1). Nitrilases share several conserved signature domains known in the art including a signature domain herein referred to as the "catalytic signature sequence" or "signature sequence". This region comprises an essential cysteine residue (e.g., $Cys_{164}$ of SEQ ID NO: 4). As such, polypeptides having nitrilase activity can be identified by the existence of the catalytic domain signature sequence (SEQ ID NO: 1). In a preferred embodiment, the signature sequence is SEQ ID NO: 2. The enzyme catalyst may be in the form of whole microbial cells or permeabilized microbial cells. As used herein, "recycled enzyme catalyst" refers to an enzyme catalyst that is reused as an enzyme catalyst in batch or continuous reactions. Depending on the step in the process of producing or using the enzyme catalyst as described herein, the enzyme catalyst may be glutaraldehyde pretreated, immobilized, cross-linked and dehydrated or rehydrated.

As used herein, the terms "*Acidovorax facilis*" and "*A. facilis*" are used interchangeably and refer to *Acidovorax facilis* 72W deposited to the American Type Culture Collection (an international depository authority) having accession number 55746 ("ATCC 55746"). The mutant nitrilases derived from *A. facilis* 72W characterized by improved nitrilase activity when converting glycolonitrile to glycolic acid have been previously reported (see co-owned U.S. Pat. No. 7,198,927). Examples of these *A. facilis* 72W-derived mutant nitrilases are provided by SEQ ID NOs: 27, 29, 31, 33, 35, 37, 39, 41, 43, 45, 47, 49, 51, 53, and 55.

As used herein, the terms "*Escherichia coli*" and "*E. coli*" are used interchangeably. Several strains of *E. coli* suitable for recombinant expression are described herein including, but not limited to *E. coli* MG1655 having international depository number ATCC 47076, *E. coli* FM5 having international depository number ATCC 53911, *E. coli* W3110 having international depository number ATCC 27325, *E. coli* MC4100 having international depository number ATCC 35695, and *E. coli* W1485 having international depository number ATCC 12435. In one embodiment, suitable *Escherichia coli* strains include *E. coil* FM5 (ATCC 53911) and *E. coli* MG1655 (ATCC 47076).

As used herein, the terms "*E. coli* SS1001" or "SS1001" refer to a transformed *E. coli* strain expressing the *Acidovorax facilis* 72W nitrilase having ATCC Accession No. PTA-1177 (see U.S. Pat. No. 6,870,038; herein incorporated in its entirety by reference). The recombinantly expressed *E. coli* SS1001 nitrilase (SEQ ID NO: 57) contains 2 minor sequence changes in comparison to the wild-type 72W nitrilase sequence (SEQ ID NO: 4). The start codon was changed from GTG to ATG to facilitate recombinant expression and an artifact was introduced during cloning that resulted in a single amino acid change near the C-terminal (Pro367 [CCA]→Ser [TCA]).

As used herein, the terms "suitable aqueous glycolonitrile reaction mixture" and "suitable aqueous reaction mixture" refer to the materials (including at least one amine protectant) and water in which the glycolonitrile and enzyme catalyst come into contact. The components of the suitable aqueous reaction mixture are provided herein and those skilled in the art appreciate the range of component variations suitable for this process.

As used herein, the terms "aqueous ammonium glycolate solution", "aqueous solution comprising ammonium glycolate", and "aqueous solution of ammonium glycolate" will be used to describe an aqueous solution comprising ammonium glycolate produced by the enzymatic hydrolysis of glycolonitrile under typical enzymatic reaction conditions (i.e., a pH range of about 6 to about 8). The aqueous solution of ammonium glycolate comprises ammonium glycolate at a concentration of at least about 0.1 weight percent (wt %) to about 99 wt % ammonium glycolate. In another embodiment, the aqueous solution of ammonium glycolate is comprised of at least about 10 wt % to about 75 wt % ammonium glycolate. In a further embodiment, the aqueous solution of ammonium glycolate is comprised of at least about 20 wt % to about 50 wt % ammonium glycolate. The pH of the aqueous solution of ammonium glycolate can be about 2 to about 12, preferably 5 to about 10, more preferably 6 to about 8. The pH may be adjusted as needed prior to initiating process steps related to recovering glycolic acid (in the form of the acid or salt) from the aqueous ammonium glycolate solution.

As used herein, the terms "catalyst productivity" and "enzyme catalyst productivity" refer to the total amount of product produced per gram of enzyme catalyst dry cell weight. In the present invention, the enzyme catalyst comprises a nitrilase enzyme (EC 3.5.5.7) and the product formed is glycolic acid and/or ammonium glycolate (depending upon the pH of the reaction). In general, the processes produced pursuant to producing glycolic acid are conducted under essentially pH neutral conditions so that the glycolic acid produced is predominantly in the form of the corresponding salt of glycolic acid (i.e. ammonium glycolate). Generally, in batch reactions with catalyst recycle, the catalyst activity decreases with each recycle reaction (enzyme inactivation).

As used herein, the term "volumetric productivity" refers to the volumetric production of glycolic acid in the reaction, expressed as grams of glycolic acid produced per volume of reaction mixture per unit of time. Typically, volumetric productivity is expressed as grams glycolic acid/L/h.

The term "nitrilase activity" or "specific activity" refers to the enzyme activity per unit mass (for example, milligram) of protein, dry cell weight, or bead weight (immobilized catalyst) when converting glycolonitrile to glycolic acid (or the corresponding ammonium glycolate). Comparisons in nitrilase activity were measured proportional to the dry cell weight or bead weight.

As used herein, the term "one unit of enzyme activity" or "one unit of nitrilase activity" or "U" is defined as the amount of enzyme activity required for the production of 1 µmol of glycolic acid product per minute (GLA U/g dry cell weight or bead weight) at a specified temperature (e.g. 25° C.).

As used herein, the terms "relative nitrilase activity", "improved nitrilase activity", and "relative improvement in nitrilase activity" refers to the nitrilase activity expressed as a multiple (or fraction) of a reference (control) nitrilase activity. The nitrilases described herein exhibit a significant improvement in nitrilase activity relative to the nitrilase activity observed with native *Acidovorax facilis* 72W nitrilase. A "significant improvement" in relative nitrilase activity is an improvement of at least 1.5-fold higher nitrilase activity in comparison to the nitrilase activity of a control under identical reaction conditions. In another embodiment, the improvement is at least 2-fold higher nitrilase activity in comparison to the nitrilase activity of the control under identical reaction conditions. In a further embodiment, the improvement is at least 4-fold higher nitrilase activity in comparison to the nitrilase activity of the control under identical reaction conditions.

As used herein, the term "initial reaction rate" is a measurement of the rate of conversion of glycolonitrile to glycolic acid under the stated reaction conditions, where the measurement of reaction rate begins upon the initial addition of glycolonitrile to the reaction mixture, and where the reaction rate is measured over a period of time where the concentration of glycolonitrile remains above ca. 50 millimolar (mM) during the course of the reaction. The reaction rate is measured as the change in concentration of glycolic acid produced per unit time (e.g., mole glycolic acid/L/min or mM glycolic acid/hour).

As used herein, the term "improved retention of initial specific activity" refers to a comparison of a glutaraldehyde pretreated, immobilized and cross-linked enzyme catalyst with a non-glutaraldehyde pretreated, immobilized and cross-linked enzyme catalyst, both having nitrilase activity, during conversion of glycolonitrile to glycolic acid under the stated reaction conditions following dehydration and rehydration, measured as micromoles of glycolic acid produced per minute per g dry cell weight of enzyme catalyst, or micromoles glycolic acid produced per minute per g immobilized and cross-linked enzyme catalyst, wherein the specific activity as measured in a first or "initial" reaction following rehydration, is retained to a greater extent for the glutaraldehyde pretreated immobilized and cross-linked enzyme catalyst than for the non-glutaraldehyde pretreated, immobilized and cross-linked enzyme catalyst, for one or more subsequent reactions. The most notable improvement, as described herein, is for the amount of activity retained for the reaction immediately following an initial batch reaction, measured in one or more subsequent batch reactions with catalyst recycle. A second notable improvement, as described herein, is for the amount of activity retained during the course of running the reaction in a continuously stirred tank reactor (CSTR), or in a fixed-bed plug flow reactor, or in a fluidized-bed or semifluidized bed reactor, after the production of at least 40 g of glycolic acid per gram dry cell weight of glutaraldehyde-pretreated immobilized and cross-linked enzyme catalyst that has been dehydrated and rehydrated.

As used herein, the terms "recombinant organism", "transformed host", "transformant", "transgenic organism", and "transformed microbial host" refer to a host organism having been transformed with heterologous or foreign DNA. The recombinant organisms of the present invention express foreign coding sequences or genes that encode active nitrilase enzyme. "Transformation" refers to the transfer of a DNA fragment into the host organism. The transferred DNA fragment can be chromosomally or extrachromosomally incorporated (i.e., via a vector) into the host organism. As used herein, the term "transformation cassette" refers to a specific fragment of DNA containing a set of genetic elements conveniently arranged for insertion into a host cell, usually as part of a plasmid. As used herein, the term "expression cassette" refers to a specific fragment of DNA containing a set of genetic elements conveniently arranged for insertion into a host cell, usually as part of a plasmid that also allows for enhanced gene expression in the host.

As used herein, the terms "nucleic acid fragment" and "nucleic acid molecule" refer to DNA molecule that may encode an entire gene, coding sequence, and/or regulatory sequences preceding (5', upstream) or following (3', downstream) the coding sequence. In one aspect, the present nucleic acid molecules encode for polypeptides having nitrilase activity.

As used herein, the term "gene" refers to a nucleic acid molecule that expresses a specific protein. As used herein, it may or may not including regulatory sequences preceding (5' non-coding sequences) and following (3' non-coding sequences) the coding sequence. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding sequence" refers to a DNA sequence that codes for a specific amino acid sequence. As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

As used herein, the term "operably linked" refers to the association of nucleic acid sequences on a single nucleic acid molecule so that the function of one sequence is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "3' non-coding sequences" refers to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias. Codon-optimization is well known in the art and has been described for various systems including, but not limited to yeast (Outchkourov et al., *Protein Expr Purif,* 24(1):18-24 (2002)) and *E. coli* (Feng et al., *Biochemistry,* 39(50):15399-15409 (2000)).

Enzyme Catalysts Having Nitrilase Activity

All nitrilases (EC 3.5.5.7) share a conserved catalytic triad (Glu, Lys, and Cys) (Chauhan et al., *Appl. Microbial. Biotechnol.* 61:118-122 (2003); Pace, H. and Brenner, C., *Genome Biol.* [online computer file] 2(1): reviews 0001.1-0001.9 (2001)). All known nitrilases have a nucleophilic cysteine in the enzyme active site (Cowan et al., *Extremophiles,* 2:207-216 (1998); Pace, H. and Brenner, C., supra; and Chauhan et al., supra) and all are susceptible to inactivation by thiol reagents (1.0 mM concentrations of copper chloride, silver nitrate, mercuric acetate, or ferric chloride each produced major decreases in *A. facilis* 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *A. facilis* 72W cells are robust, capable of retaining much of their nitrilase activity after numerous recycle reactions (U.S. Pat. Nos. 6,870,038; 7,148,051; 7,198,927; and Chauhan et al., supra). Nitrilase catalysts derived from the *A. facilis* 72W nitrilase also been shown to catalyze the conversion of α-hydroxynitriles (i.e., glycolonitrile) to α-hydroxycarboxylic acids (i.e., glycolic acid) (see U.S. Pat. Nos. 6,383,786; 6,416,980; and 7,198,927).

Sequence comparisons of the *A. facilis* 72W nitrilase to other bacterial nitrilases have been reported (U.S. Pat. No. 6,870,038; Chauhan et al., supra). The 72W nitrilase has several conserved signature domains including a 16-amino acid region near the amino terminus (amino acid residues 40-55 of SEQ ID NO: 4) and a 12 amino acid catalytic region (amino acid residues 160-171 of SEQ ID NO: 4) containing the essential cysteine residue. This essential cysteine residue ($Cys_{164}$ of SEQ ID NO: 4), along with conserved glutamic acid ($Glu_{48}$ of SEQ ID NO:4) and lysine residues ($Lys_{130}$ of SEQ ID NO:4), form the catalytic triad motif found in all nitrilases (Pace, H., and Brenner, C., supra).

The regions surrounding each of the catalytic triad residues are highly conserved, especially the region surrounding the catalytic cysteine residue. The essential catalytic cysteine residue is located with a highly conserved region referred to as the "catalytic signature motif" or "signature motif". As such, the present process is useful for protecting the enzymatic activity of any nitrilase comprising the catalytic signature motif defined by Formula 1 (bold indicates strictly conserved amino acid residues, italicized residues are those that exhibit minimal variability [i.e. minimal variation of 3 or fewer amino acid residues], the catalytic cysteine residue is underlined):

Formula 1
(SEQ ID NO: 1).
Gly-*Xaa₁*-*Xaa₂*-Xaa₃-Cys-Trp-Glu-*Xaa₄*-Xaa₅-Xaa₆-Xaa₇-Xaa₈ wherein
$Xaa_1$=Ala or Gly;
$Xaa_2$=Leu, Val, or Ala;
$Xaa_3$=Ala, Asn, Ile, Cys, Val, or Gln;
$Xaa_4$=His or Asn;
$Xaa_5$=Leu, Tyr, Phe, Ala, Met, Lys, Val, Thr, or Arg;
$Xaa_6$=Asn, Gln, Met, Leu, or Ser;
$Xaa_7$=Pro or Thr; and
$Xaa_8$=Leu or Val.

In a preferred embodiment, the nitrilase signature motif of Formula 1 is $Xaa_1$=Ala or Gly; $Xaa_2$=Leu; $Xaa_3$=Ala, Asn, Ile, Cys, Val, or Gln; $Xaa_4$=His; $Xaa_5$=Leu, Tyr, Phe, Ala, Met, Lys, Val, Thr or Arg; $Xaa_6$=Ser, Gln, Asn, or Met; $Xaa_7$=Pro; and $Xaa_8$=Leu; resulting in the catalytic signature motif represented by the following:

(SEQ ID NO: 2)
Gly-Xaa₁-Leu-Xaa₃-Cys-Trp-Glu-His-Xaa₅-Xaa₆-Pro-Leu

Examples of nitrilases, including the sequences and position of the corresponding catalytic signature motif sequence, are provided in Table 1.

TABLE 1

Conserved Catalytic Cysteine Region-Catalytic Signature Motifs

| Nitrilase Source | GenBank® Accession Number | Amino Acid SEQ ID NO. | Sequence of Signature Motif (amino acid residue positions) |
|---|---|---|---|
| Acidovorax Facilis 72W | ABD98457.1 | 4 | GGLNCWEHFQPL (160-171) |
| Alcaligenes faecalis JM3 | BAA02684.1 | 5 | GALCCWEHLSPL (159-170) |
| Rhodococcus rhodochraus J1 | Q03217 | 6 | GALNCWEHFQTL (161-172) |
| Rhodococcus rhodochrous K22 | Q02068 | 7 | GGLNCWEHEQPL (166-177) |
| Nocardia sp. C-14-1 | AAX18182.1 | 8 | GGLNCWEHFQPL (154-165) |
| Bordetella bronchiseptica RB50 | NP_887662.1 | 9 | GAVVCWENYMPL (161-172) |
| Arabidopsis thaliana | AAB60275.1 AAA19627.1 | 10 | GAAICWENRMPL (175-186) |
| Synechococcus elongatus PCC 7942 | YP_399857.1 | 11 | GALACWEHYNPL (157-168) |
| Synechococcus elongatus PCC 6301 | YP_171411.1 | 12 | GALACWEHYNPL (157-168) |
| Synechocystis sp. PCC 6803 | NP_442646.1 | 13 | GALACWEHYNPL (165-176) |
| Pseudomonas entomophila L48 | YP_609048I.1 | 14 | GAAVCWENYMPL (161-172) |
| Zymomonas moblis | YP_162942.1 | 15 | GAAICWENYMPV (161-172) |
| Bacillus sp. OxB-1 | BAA90460.1 | 16 | GGLQCWEHFLPL (158-169) |
| Comamonas testosteroni | AAA82085.1 | 17 | GGLQCWEHALPL (159-170) |
| Synechococcus sp. CC9605 | YP_381420.1 | 18 | GALACWEHYNPL (156-167) |
| Pseudomonas fluorescans Pf-5 | YP_260015.1 | 19 | GAVICWENMMPL (161-172) |
| Nocardia farcinica IFM 10152 | YP_119480.1 | 20 | GALCCWEHLQPL (159-170) |
| Alcaligenes faecalis 1650 | AAY06506.1 | 21 | GALCCWEHLSPL (159-170) |

TABLE 1-continued

Conserved Catalytic Cysteine Region-Catalytic Signature Motifs

| Nitrilase Source | GenBank® Accession Number | Amino Acid SEQ ID NO. | Sequence of Signature Motif (amino acid residue positions) |
|---|---|---|---|
| *Pseudomonas syringae* pv. *syringae* B728a | AAY35081.1 | 22 | GALCGWEHLQPL (157-168) |
| *Bradyrhizobium* sp. BTAi1 | ZP_00859948.1 | 23 | GALCCWEHLQPL (163-174) |
| *Rhodococcus rhodochrous* NCIMB 11216 | CAC88237 | 24 | GALNCWEHFQTL (161-172) |
| *Rhodococcus rhodochrous* ATCC 39484™ | N/A | 25 | GALNCWEHFQTL (161-172) |

In one embodiment, the nitrilase catalyst comprises a polypeptide having nitrilase activity isolated from a genera selected from the group consisting of *Acidovorax, Rhodococcus, Nocardia, Bacillus,* and *Alcaligenes.* In one embodiment, the nitrilase catalyst comprises a polypeptide having nitrilase activity isolated from a genera selected from the group consisting of *Acidovorax* and *Rhodococcus.*

In another embodiment, the polypeptide having nitrilase activity is derived from *Acidovorax facilis* 72W (ATCC 55746) or a polypeptide (having nitrilase activity) that is substantially similar to the *Acidovorax facilis* 72W nitrilase (SEQ ID NO: 4) or the *A. facilis* 72W derived enzyme represented by SEQ ID NO: 51.

In one embodiment, the nitrilase catalyst is a microbial host cell transformed to express at least one polypeptide having nitrilase activity. In one embodiment the transformed host cell is selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. In a preferred embodiment, the microbial host cell is selected from the group consisting of *Bacillus* sp., *Pseudomonas* sp., and *Escherichia* sp. In a preferred embodiment, the catalyst is an *Escherichia coli* host cell recombinantly expressing one or more of the polypeptides having nitrilase activity.

In another embodiment, the nitrilase catalyst comprises a polypeptide having nitrilase activity wherein said polypeptide having nitrilase activity has at least 60% identity to SEQ ID NO: 51, preferably at least 70% identity to SEQ ID NO: 51, even more preferably at least 80% identity to SEQ ID NO: 51, yet even more preferably at least 90% identity to SEQ ID NO: 51, and most preferably at least 95% identity to SEQ ID NO: 51.

Working examples of several catalysts having nitrilase activity derived from various sources are described herein, including a catalyst derived from the *A. facilis* 72W nitrilase.

Various mutants derived from the *Acidovorax facilis* 72W nitrilase enzyme have been reported in the art (U.S. Pat. No. 7,148,051 and U.S. Pat. No. 7,198,927).

In one embodiment, the polypeptide having nitrilase activity is selected from the group consisting of SEQ ID NOs: 4, 5, 6, 7, 8, 9, 10, 11, 12, 13, 14, 15, 16, 17, 18, 19, 20, 21, 22, 23, 24, 25, 27, 29, 31, 33, 35, 37, 39, 41, 43, 45, 47, 49, 51, 53, 55, and 57. In another embodiment, the polypeptide having nitrilase activity is selected from the group consisting of 4, 24, 25, 27, 29, 31, 33, 35, 37, 39, 41, 43, 45, 47, 49, 51, 53, 55, and 57. In another embodiment, the polypeptide having nitrilase activity is selected from the group consisting of 4, 27, 29, 31, 33, 35, 37, 39, 41, 43, 45, 47, 49, 51, 53, 55, and 57. n another embodiment, the polypeptide having nitrilase activity is selected from the group consisting of 4, 24, 25, and 51. In another embodiment, the nitrilase catalyst comprises the polypeptide of SEQ ID NO: 51.

*Acidovorax facilis* 72W (ATCC 55746) Nitrilase

The *A. facilis* 72W nitrilase (EC 3.5.5.1) is a robust catalyst for producing carboxylic acids from aliphatic or aromatic nitriles (WO 01/75077; U.S. Pat. No. 6,870,038; and Chauhan et al., supra). It has also been shown to catalyze the conversion of α-hydroxynitriles (i.e., glycolonitrile) to α-hydroxycarboxylic acids (i.e., glycolic acid) (see U.S. Pat. No. 6,383,786 and U.S. Pat. No. 6,416,980). However, nitrilase catalysts having improved nitrilase activity and/or stability (relative to the *A. facilis* 72W nitrilase) when converting glycolonitrile to glycolic acid would reduce the cost of manufacturing glycolic acid. As such, a method of producing glycolic acid using an improved nitrilase catalyst is useful to reduce the cost of manufacturing glycolic acid, however *A. facilis* 72W nitrilase is an enzyme catalyst for purposes of the processes herein, as well as said improved nitrilases described in detail above.

Industrial Production of the Microbial Catalyst

Where commercial production of the enzyme catalysts described herein is desired, a variety of culture methodologies may be used. Fermentation runs may be conducted in batch, fed-batch, or continuous mode, methods well-known in the art (Thomas D. Brock in *Biotechnology: A Textbook of Industrial Microbiology*, Second Edition (1989) Sinauer Associates, Inc., Sunderland, Mass., (1989); Deshpande, Mukund V., *Appl. Biochem. Biotechnol.* 36(3): 227-234 (1992)).

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of the present enzyme catalysts having nitrilase activity may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end cell concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of cell formation, are well known in the art of industrial microbiology and a variety of methods are detailed by Brock (supra).

Fermentation media in the present invention must contain suitable carbon substrates. Suitable substrates may include, but are not limited to monosaccharides such as glucose and fructose, disaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon-containing substrates and will only be limited by the choice of organism.

Glutaraldehyde Pretreatment of the Enzyme Catalyst Prior to Immobilization

Treatment of an enzyme catalyst fermentation culture with glutaraldehyde can be a convenient way to kill the microbes in the culture, thus avoiding containment and safety issues for handling, storage and transportation associated with live recombinant cultures. It has now been discovered that pretreatment with glutaraldehyde, or glutaraldehyde pretreatment followed by bisulfite treatment, can preserve nitrilase activity in cells in suspension and in an immobilized form.

Preservation of nitrilase activity with glutaraldehyde pretreatment of an enzyme catalyst is affected by time, temperature, glutaraldehyde concentration, pH and the concentration of inhibitory products like ammonia and other amines (e.g., amino acids and peptides) in the media that interact with glutaraldehyde. A preferred glutaraldehyde pretreatment method treats cells from high-density fermentation (100-150 $OD_{550}$) with 5-10 wt % glutaraldehyde in water that is preferably delivered with adequate mixing at 50 mg to 500 mg glutaraldehyde/L-min, more preferably delivered with adequate mixing at 50 mg to 200 mg glutaraldehyde/L-min, most preferably delivered with adequate mixing at 50 mg to 100 mg glutaraldehyde/L-min, resulting in a final concentration of about 3 g to about 5 g glutaraldehyde/L (about 0.025 g to about 0.042 g glutaraldehyde per $OD_{550}$), more preferably about 3.6 g to about 5 g glutaraldehyde/L (about 0.030 g to about 0.042 g glutaraldehyde per $OD_{550}$). The glutaraldehyde pretreated culture may be held in the fermenter for about 1 to 5 hours. A 10 wt % solution of sodium bisulfite in water is then optionally added at 1 g/L to inactivate the residual glutaraldehyde.

The preferred pH for the glutaraldehyde pretreatment of the enzyme catalyst in the fermentation broth or cell suspension is from pH 5.0 to 9.0, more preferably from pH 5.0 to 8.0, even more preferably from pH 5.0 to 7.0, still more preferably pH 5.0 to 6.0, and most preferably pH 5.0 to 5.5. The residual glutaraldehyde concentration after glutaraldehyde pretreatment is typically low, in the range of 10-200 ppm, and can be inactivated as stated above, with the addition of sodium bisulfite to a final concentration of about 1 g/L. Glutaraldehyde and bisulfite pretreatment were found to have no significant detrimental effect on the nitrilase activity. The glutaraldehyde or glutaraldehyde/bisulfite pretreated cell suspension is optionally chilled to 5-10° C., and optionally washed (by concentration and re-dilution of the cell suspension or fermentation broth) with water or an appropriate storage buffer to remove residual bisulfite and unreacted glutaraldehyde.

Immobilization of Glutaraldehyde Pretreated Enzyme Catalyst and Chemical Cross-linking Methods for the immobilization of enzyme catalysts have been widely reported and are well known to those skilled in the art (Methods in Biotechnology, Vol. 1: *Immobilization of Enzymes and Cells*; Gordon F. Bickerstaff, Editor; Humana Press, Totowa, N.J., USA; 1997). The immobilization of the *A. facilis* 72W nitrilase catalyst has also been previously reported (U.S. Pat. No. 6,870,038).

Further, a method for immobilization in carrageenan and subsequent glutaraldehyde/polyethylenimine cross-linking of the immobilized enzyme catalyst follows (and as disclosed in U.S. Pat. No. 6,870,038, and as described in detail in U.S. Pat. No. 6,551,804 B, herein incorporated by reference), however, one of ordinary skill in the art would recognize and readily apply variations to accomplish immobilization and cross-linking. Said variations are contemplated herein and are within the scope of the instant process. Further, the amounts or concentrations of components used for immobilization and chemical cross-linking will vary depending on the amount and type of enzyme catalyst and fermentative production of enzyme catalyst. One of ordinary skill in the art would recognize these factors and adjust the immobilization and chemical cross-linking procedures accordingly. With regard to cross-linking with glutaraldehyde and polyethylenimine, U.S. Pat. No. 6,551,804 (supra), describes the processes and procedures for chemically cross-linking alginate immobilized cells. Said description applies here for carrageenan immobilized cells as well.

Dehydration/Rehydration of Glutaraldehyde/Polyethylenimine Cross-Linked Carrageenan-Immobilized Microbial Enzyme Catalyst As stated above, a particular issue related to the use of a microbial nitrilase catalyst addressed in the present application is storage and shipment of the enzyme catalyst. Aspects of concern for storage and shipment of enzyme catalysts having nitrilase activity include difficulties with the volume of the material and inactivation of the enzyme activity of the material over time. When immobilized in carrageenan and subsequently cross-linked with glutaraldehyde and polyethylenimine, the resulting immobilized microbial nitrilase catalyst was about 90% by weight water, and the catalyst was typically stored at 5° C. in an equivalent weight of aqueous buffer. A reduction in the amount of water present in the immobilized microbial nitrilase catalyst, and elimination of the aqueous buffer used to store the catalyst, would decrease the volume of catalyst and associated buffer that needed to be shipped and stored prior to use, and further significantly improve the economics of glycolic acid manufacture.

Dehydration of the glutaraldehyde/polyethylenimine cross-linked immobilized enzyme catalyst can be accomplished by any method known to those skilled in the art, including, but not limited to, dehydration in air, dehydration in a stream of an inert gas, dehydration in a vacuum oven with or without an inert gas (for example, nitrogen or argon) purge, or lyophilization (freeze-drying). The temperature for dehydration may preferably range from about 5° C. to about 60° C., more preferably range from about 15° C. to about 50° C., and most preferably range from about 20° C. to about 40° C. The resulting dehydrated beads may lose up to about 91% of their initial wet weight (when starting with beads comprised of about 5% dry cell weight microbial nitrilase-containing cells). The dehydrated immobilized cell catalyst may be stored in air or under an inert atmosphere, and at temperatures preferably in the range from −25° C. to 35° C., preferably from 5° C. to 25° C. The dehydrated immobilized cell catalyst may be rehydrated by placing the dehydrated beads in water, or in an appropriate aqueous buffer, for example, a solution of 0.10 M ammonium glycolate (pH 7.3), the rehydration temperature is preferably from about 5° C. to about 35° C. The resulting rehydrated beads may be used directly in a reaction for the production of glycolic acid from glycolonitrile, or stored in the rehydration liquid at from about 5° C. to about 35° C. until used.

Hydrolysis of Glycolonitrile to Glycolic Acid Using a Nitrilase Catalyst

The enzymatic conversion of glycolonitrile to glycolic acid (in the form of the acid and/or the corresponding ammonium salt) may be performed by contacting an enzyme catalyst, immobilized enzyme catalyst, or cross-linked immobilized enzyme catalyst having nitrilase activity under suitable reaction conditions as described below (i.e. in an aqueous reaction mixture at certain pH range, temperatures, concentrations, etc.). In one embodiment, whole recombinant microbial cells are glutaraldehyde pretreated, immobilized in carrageenan, cross-linked, dehydrated, and upon rehydration the resulting enzyme catalyst is used directly for the conversion of glycolonitrile to glycolic acid, or unimmobilized cells can be maintained separately from the bulk reaction mixture using hollow-fiber membrane cartridges or ultrafiltration membranes. In a second embodiment, whole recombinant microbial cells are immobilized in polyacrylamide gel, and the resulting enzyme catalyst used directly for the conversion of glycolonitrile to glycolic acid.

The concentration of enzyme catalyst in the aqueous reaction mixture depends on the specific activity of the enzyme catalyst and is chosen to obtain the desired rate of reaction. The wet cell weight of the microbial cells used as catalyst in hydrolysis reactions typically ranges from 0.001 grams to 0.250 grams of wet cells per mL of total reaction volume, preferably from 0.002 grams to 0.050 grams of wet cells per mL. The indicated wt % of wet cells per volume of total reaction volume may be present in the reaction mixture in the form of an immobilized enzyme catalyst prepared as previously described (supra), where the weight of wet cells as a percentage of the total weight of the immobilized enzyme catalyst is known from the method of preparation of the immobilized enzyme catalyst.

The temperature of the glycolonitrile hydrolysis reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C. The enzyme catalyst suspension may be prepared by suspending the dehydrated immobilized cells in distilled water, or in a aqueous solution of a buffer which will maintain the initial pH of the reaction between about 5.0 and about 10.0, preferably between about 5.5 and about 8.0, more preferably between about 5.5 and about 7.7, and most preferably about 6.0 to about 7.7. As the reaction proceeds, the pH of the reaction mixture may change due to the formation of an ammonium salt of the carboxylic acid from the corresponding nitrile functionality. The reaction can be run to complete conversion of glycolonitrile with no pH control, or a suitable acid or base can be added over the course of the reaction to maintain the desired pH.

Glycolonitrile was found to be completely miscible with water in all proportions at 25° C. In cases where reaction conditions are chosen such that the solubility of the substrate (i.e., an α-hydroxynitrile) is also dependent on the temperature of the solution and/or the salt concentration (buffer or product glycolic acid ammonium salt, also known as ammonium glycolate) in the aqueous phase, the reaction mixture may initially be composed of two phases: an aqueous phase containing the enzyme catalyst and dissolved α-hydroxynitrile, and an organic phase (the undissolved α-hydroxynitrile). As the reaction progresses, the α-hydroxynitrile dissolves into the aqueous phase, and eventually a single phase product mixture is obtained. The reaction may also be run by adding the α-hydroxynitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

Glycolic acid may exist in the product mixture as a mixture of the protonated carboxylic acid and/or its corresponding ammonium salt (dependent on the pH of the product mixture; pKa of glycolic acid is about 3.83), and may additionally be present as a salt of the carboxylic acid with any buffer that may additionally be present in the product mixture. Typically, the glycolic acid produced is primarily in the form of the ammonium salt (pH of the glycolonitrile hydrolysis reaction is typically between about 5.5 and about 7.7). The glycolic acid product may be isolated from the reaction mixture as the protonated carboxylic acid, or as a salt of the carboxylic acid, as desired.

The final concentration of glycolic acid in the product mixture at complete conversion of glycolonitrile may range from 0.001 M to the solubility limit of the glycolic acid product. In one embodiment, the concentration of glycolic acid will range from about 0.10 M to about 5.0 M. In another embodiment, the concentration of glycolic acid will range from about 0.2 M to about 3.0 M.

Glycolic acid may be recovered in the form of the acid or corresponding salt using a variety of techniques including, but not limited to ion exchange, electrodialysis, reactive solvent extraction, polymerization, thermal decomposition, alcoholysis, and combinations thereof.

Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

GENERAL METHODS

The following examples are provided to demonstrate preferred embodiments of the invention. It should be appreciated by those of skill in the art that the techniques disclosed in the examples which follow represent techniques discovered by the inventor to function well in the practice of the invention, and thus may be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and methods suitable for the maintenance and growth of bacterial cultures are well known in the art. Techniques suitable for use in the following examples may be found as set out in *Manual of Methods for General Bacteriology* (1994) (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C.) or by Thomas D. Brock, in *Biotechnology: A Textbook of Industrial Microbiology*, (1989) Second Edition, (Sinauer Associates, Inc., Sunderland, Mass.). Methods to immobilize enzymatic catalysts can be found in Bickerstaff, G. F., supra).

Procedures required for genomic DNA preparation, PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis, supra; and by T. J. Silhavy, M. L. Bennan, and L. W. Enquist, *Experiments with Gene Fusions*, (1984) Cold Spring Harbor Laboratory Press, Cold Spring, N.Y.; and by Ausubel, F. M. et al., *Current Protocols in Molecular Biology*, (1994-1998) John Wiley & Sons, Inc., New York.

All reagents and materials were obtained from Aldrich Chemicals (Milwaukee, Wis.), DIFCO Laboratories (Detroit, Mich.), GIBCO/BRL (Gaithersburg, Md.), or Sigma/Aldrich Chemical Company (St. Louis, Mo.) unless otherwise specified.

The abbreviations in the specification correspond to units of measure, techniques, properties, or compounds as follows: "sec" means second(s), "min" means minute(s), "h" or "hr" means hour(s), "d" means density in g/mL, "μL" means microliters, "mL" means milliliters, "L" means liters, "mM" means millimolar, "M" means molar, "mmol" means millimole(s), "wt" means weight, "wt %" means weight percent, "g" means grams, "μg" means micrograms, "HPLC" means high performance liquid chromatography, "O.D." means optical density at the designated wavelength, "dcw" means dry cell weight, "U" means units of nitrilase activity, "EDTA" means ethylenediaminetetraacetic acid, and "DTT" means dithiothreitol. One U of nitrilase activity corresponds to the hydrolysis of 1 μmol glycolonitrile/min.

Analytical Methodology

HPLC Analysis

Unless otherwise noted, the following HPLC method was used. The reaction product mixtures were analyzed by the following HPLC method. Aliquots (0.01 mL) of the reaction mixture were added to 1.50 mL of water, and analyzed by HPLC (HPX 87H column, 30 cm×7.8 mm; 0.01 N $H_2SO_4$ mobile phase; 1.0 mL/min flow at 50° C.; 10 μL injection volume; RI detector, 20 min analysis time). The method was calibrated for glycolonitrile at a series of concentrations using commercially available glycolonitrile purchased from Aldrich.

Quantitative $^{13}C$ NMR Analysis

Quantitative $^{13}C$ NMR spectra were obtained using a Varian Unity Inova spectrometer (Varian, Inc., Palo Alto, Calif.) operating at 400 MHz. Samples were prepared by taking 3.0 mL of the reaction product along with 0.5 mL of $D_2O$ in a 10 mm NMR tube. $^{13}C$ NMR spectra were typically acquired using a spectral width of 26 KHz with the transmitter located at 100 ppm, 128K points, and a 90-degree pulse (pw90=10.7 microseconds at a transmitter power of 56 db). The longest 13C T1 (23 sec) was associated with the GLN nitrile carbon, and the total recycle time was set greater than ten times this value (recycle delay d1=240 sec, acquisition time at=2.52 sec). Signal averaging of 360 scans gave a total experiment time of 26.3 hours. The Nuclear Overhauser Enhancement (NOE) was suppressed by gating on the Waltz-modulated 1H decoupling only during the acquisition time (at).

EXAMPLE 1

Fermentation of *E. coli* MG1655/pSW138-168V

Seed cultures of *E. coli* MG1655/pSW138-168V were grown in 500 mL LB media supplemented with 0.1 mg ampicillin per mL for 6-10 h ($OD_{550}$=1-2) at 30° C. with shaking (300 rpm) prior to inoculation of the fermentor. Growth of *E. coli* MG1655/pSW138-168V nitrilase strain was in 14-L Braun Biostat C fermenters (B. Braun Biotech International Gmbh, Melsungen, Germany) using mineral medium with glucose, ammonia, and salts, and lactose was used for induction. Pre-sterilization fermenter media (7.5 L) is described in Table 2. Post-sterilization additions include filter-sterilized trace elements (Table 3), 0.1 mg ampicillin per mL, 2 g casamino acids (Difco) per L, 4 g glucose per L, and 500 mL seed culture.

Fermentation set points are described in Table 4. $NH_4OH$ (40% w/v) and $H_3PO_4$ (20% w/v) were used for pH control. The dissolved oxygen concentration was controlled at 25% of air saturation with the agitation set to rise first with increase in oxygen demand, with aeration to follow. The fermentation feed protocol used with lactose induction is given in Table 5. Glucose feed rates were reduced if glucose accumulated above 5 g/L. After 40-56 h, the fermentation broth was chilled to 5-10° C. and the cells harvested by centrifugation. Cell paste was frozen and stored at −70° C. The cell paste was designated as NIT 60 (1910 GLN U/g dcw),

TABLE 2

| Fermentation media, pre-sterilization. | |
|---|---|
| $(NH_4)_2SO_4$ | 5.0 g/L |
| $K_2HPO_4$ | 4.0 g/L |
| $KH_2PO_4$ | 3.5 g/L |
| $MgSO_4*7H_2O$ | 0.6 g/L |
| $Na_3Citrate*2H_2O$ | 1.0 g/L |
| NZ Amine AS (Quest) | 2.5 g/L |
| Antifoam - Biospumex 153K | 0.25 ml/L |

TABLE 3

| Fermentation trace elements | |
|---|---|
| | Concentration |
| Citric acid | 10 g/L |
| $CaCl_2*2H_2O$ | 1.5 g/L |

TABLE 3-continued

Fermentation trace elements

| | Concentration |
|---|---|
| $FeSO_4 \cdot 7H_2O$ | 5 g/L |
| $ZnSO_4 \cdot 7H_2O$ | 0.39 g/L |
| $CuSO_4 \cdot 5H_2O$ | 0.38 g/L |
| $CoCl_2 \cdot 6H_2O$ | 0.2 g/L |
| $MnCl_2 \cdot 4H_2O$ | 0.3 g/L |

TABLE 4

Fermentation set points

| | Initial Set-Point | Minimum | Maximum |
|---|---|---|---|
| Stirrer (rpm) | 400 | 400 | 1000 |
| Airflow (slpm) | 2 | 2 | 10 |
| pH | 6.8 | 6.8 | 6.8 |
| Pressure (kPa) | 0.5 | 0.5 | 0.5 |
| DO | 25% | 25% | 25% |
| Temperature ° C. | 30 | 30 | 30 |

TABLE 5

Fermentation feed protocol used with lactose induction

| EFT (h) | Feed Rate (g/min) | Substrate |
|---|---|---|
| 0 | 0 | Glucose (batched) |
| 5 | 0.27 | Glucose (50% w/w) |
| 14 | 1.3 | Lactose (25% w/w) |

EXAMPLE 2

Immobilization of *E. coli* MG1655/pNM18-168V in GA/PEI-Cross-linked Carrageenan Beads With rapid stirring, 12 g of carrageenan (FMC GP911) was slowly added to 228 g deionized distilled water at 50° C., the resulting mixture heated to 80° C. until the carrageenan was completely dissolved, and the resulting solution cooled with stirring to 52° C. In a separate beaker equipped with stir bar, 83.2 g of frozen *E. coli* MG1655/pNM18-168V cells (25.2% dcw) were added to 84.8 g of 0.35 M $Na_2HPO_4$ (pH 7.3) at ca. 25° C. and mixed until the cells were suspended, then a deoxyribonuclease I solution (10 µL of 12,500 U/mL DNase (Sigma)/100 mL of cell suspension) was added. The cell suspension was filtered consecutively through a 230 micron and 140 micron Nupro TF strainer element filter, and heated with stirring to 50° C. With stirring, 160.0 g of *E. coli* MG1655/pNM18-168V cell suspension at 50° C. was added to the carrageenan solution at 52° C., and the resulting cell/carrageenan suspension was pumped through an electrically-heated 20 gauge needle at 47° C. and dripped into 0.25 M $KHCO_3$ (pH=7.3) with stirring at ca. 37-38° C.); the flow rate through the needle was set at 5-8 mL/min. The resulting beads were allowed to harden in this same buffer for 1 h at room temperature with stirring, and were stored in 0.25 M potassium bicarbonate (pH 7.3).

Chemical cross-linking of the immobilized cell/carrageenan beads was performed by addition of 0.5 g of 25% glutaraldehyde (GA) in water (Sigma M 752-07) to 20 g beads suspended in 48 mL of 0.25 M potassium bicarbonate (pH 7.3), and stirring for 1 h at room temperature. To the suspension of beads was then added 2.0 g of 12.5 wt % polyethylenimine (PEI, BASF LUPASOL PS) in water, and the bead suspension stirred for an additional 18 h at room temperature. The GA/PEI-cross-linked beads were recovered from the suspension, stirred twice for 15 min in 48 mL of 0.25 M potassium bicarbonate (pH 7.3), then stored in 1.0 M ammonium bicarbonate (pH 7.3) at 5° C. Prior to use as catalyst for conversion of glycolonitrile to glycolic acid (as the ammonium salt), the beads were washed twice for 15 min with 180 mL of 0.1 M ammonium glycolate (pH 7.3) at room temperature to remove the 1.0 M ammonium bicarbonate (pH 7.3) storage buffer. The resulting immobilized cell catalyst was identified as immobilized NIT 60.

EXAMPLE 3

Dehydration/Rehydration of Glutaraldehyde/polyethylenimine Cross-linked Carrageenan-immobilized *E. coli* MG1655/pSW138-F168V Transformant Glutaraldehyde/polyethylenimine cross-linked carrageenan-immobilized *E. coli* MG1655/pSW138-F168V transformant beads prepared as described in Example 2 were dehydrated in a vacuum oven (176 mm Hg) at 35° C. with nitrogen purge for 24 h. The ratio of dehydrated bead weight to original (not dehydrated) bead weight was 0.0914. The dehydrated beads were subsequently rehydrated by placing the dehydrated beads in a 20-fold (by weight) solution of 0.10 M ammonium glycolate (pH 7.3) at either 5° C. or 25° C. for 18 h. The resulting rehydrated beads were washed twice with a 9-fold (by weight) solution of 0.10 M ammonium glycolate (pH 7.3), then weighed; the ratio of rehydrated bead weight to original (not dehydrated) bead weight was 0.210 for beads rehydrated at 5° C., and the ratio of rehydrated bead weight to original bead weight was 0.212 for beads rehydrated at 25° C.

EXAMPLE 4

Specific Activity of Glutaraldehyde/polyethylenimine Cross-linked Carrageenan-immobilized *E. coli* MG1655/pSW138-F168V Transformant Before and after Dehydration/Rehydration Batch reactions for the conversion of glycolonitrile to glycolic acid were run at 25° C. in a temperature-controlled water bath. A first reaction vessel equipped with magnetic stir bar was charged with 8.0 g of GA/PEI-cross-linked *E. coli* MG1655/pSW138-168V/carrageenan beads (0.40 g dry cell weight, prepared as described in Example 2 with no dehydration/rehydration), 6.0 mL of aqueous ammonium glycolate (4.0 M, pH 7.0) and 21.7 mL of deionized, distilled water. A second reaction vessel equipped with magnetic stir bar was charged with 1.71 g of rehydrated GA/PEI cross-linked *E. coli* MG1655/pSW138-168V/carrageenan beads (0.41 g dry cell weight, prepared as described in Example 3 with dehydration at 35° C. and rehydration at 5° C.), 6.0 mL of aqueous ammonium glycolate (4.0 M, pH 7.0) and 28.0 mL of deionized, distilled water. A third reaction vessel equipped with magnetic stir bar was charged with 1.70 g of rehydrated GA/PEI cross-linked *E. coli* MG1655/pSW138-168V/carrageenan beads (0.40 g dry cell weight, prepared as described in Example 2 with dehydration at 35° C. and rehydration at 25° C.), 6.0 mL of aqueous ammonium glycolate (4.0 M, pH 7.0) and 28.0 mL of deionized, distilled water. To each reaction vessel was then added simultaneously with stirring 3.50 mL (3.75 g) of 60.8 wt % glycolonitrile (GLN) in water (40.0 mmol GLN, 0.320 mmol formaldehyde; stabilized with 0.7 wt % glycolic acid)) and 0.80 mL of aqueous ammonium hydroxide (1.875 wt % $NH_3$) was added (final pH 7.5). Reaction samples (0.100 mL) were removed at pre-determined times after GLN addition and mixed with 0.100 mL of water, 0.010 mL of 6.0 N HCl and 0.200 mL of 0.25 M n-propanol in water (HPLC external standard), the mixture centrifuged, and the resulting supernatant analyzed by HPLC to determine the initial reaction rate and catalyst specific activity (U/g dcw) (Table 6).

TABLE 6

Specific Activity of Glutaraldehyde/polyethylenimine Cross-linked Carrageenan-immobilized E. coli MG1655/pSW138-F168V Transformant Before and After Dehydration/Rehydration.

| immobilized cell biocatalyst | dehydration temperature (° C.) | rehydration temperature (° C.) | specific activity (U/g dcw) | activity after rehydration (%) |
|---|---|---|---|---|
| No dehydration | none | None | 1787 | |
| dehydrated/rehydrated | 35 | 5 | 1049 | 59 |
| dehydrated/rehydrated | 35 | 25 | 1032 | 58 |

EXAMPLE 5

Pretreatment of E. coli MG1655/pSW138-168V with Glutaraldehyde Prior to Immobilization A 200-L fermentation was performed to produce a broth containing E. coli MG1655/pSW138-168V cells that were subsequently pretreated with glutaraldehyde in-situ prior to immobilization. A pre-seed culture was first prepared by charging a 2-L shake flask with 0.5 L seed medium containing yeast extract (Ambrex 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (10 mL, 50 wt %) and 1 mL ampicillin (25 mg/mL). The pre-seed medium was inoculated with a 1-mL frozen stock culture of E. coli MG1655/pSW138-168V in 20% glycerol, and cultivated at 35° C. and 300 rpm. The seed culture was transferred at ca. 2 $OD_{550}$ to a 14 L seed fermentor (Braun) with 8 L of medium containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Biospumex153K antifoam (0.25 mL/L, Cognis Corporation), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included 120 g glucose solution (50% w/w) and ampicillin 16 mL stock solution (25 mg/mL).

The dissolved oxygen (dO) concentration was controlled at 25% of air saturation. The dO was controlled first by impeller agitation rate (400 to 1400 rpm) and later by aeration rate (2 to 10 slpm). The pH was controlled at 6.8. $NH_4OH$ (29% w/w) and $H_2SO_4$ (20% w/v) were used for pH control. The temperature was controlled at 35° C. and the head pressure was 0.5 bars. At ca 6 $OD_{550}$ the culture was transferred to the 200 L Biostat-D Braun fermenter. The medium used was the same as in the seed fermenter, the initial working volume was 140 L and 50% w/w glucose was charged to 8 g/L. The fermentation started as a batch operation, and once the glucose was depleted (<0.5 g/L) a fed batch operation with 50% w/w glucose was initiated with a predetermined rate (Table 6), at ca 25 $OD_{550}$ the feed was switched to 25% D-lactose solution with a pre-determined rate (Table 7).

The temperature was controlled at 35.0° C., the head pressure at 0.5 bar, the pH at $1^{st}$ stage (glucose phase) at 6.8 and at the $2^{nd}$ stage (lactose phase) at 7.2, $NH_4OH$ (29% w/w) and $H_2SO_4$ (20% w/v) were used for pH control, the dO controlled at $1^{st}$ stage at 25% of air saturation and $2^{nd}$ stage at 10%, the dO was controlled by agitation first (250-450 rpm) and later by aeration (25-35 slpm). Glucose and lactose levels were monitored during the fed operation and if the levels of glucose exceeds 0.1 g/L or lactose above 1 g/L the feed program was either temporarily halted or reduced. The run was ended 40 h after the initiation of lactose feed, and cells were either harvested by centrifugation or microfiltration or kept in the vessel for treatment with glutaraldehyde. The fermentation produced about 8 kg dry cell weight with a nitrilase specific activity of 2819 BZN U/g dcw (1788 GLN U/g dcw).

TABLE 7

Feed protocol

| Feed time intervals (h) | Feed rate g/min | Substrate | Stage |
|---|---|---|---|
| 0 | 6.13 | 50% w/w glucose | $1^{st}$ |
| 1 | 7.13 | 50% w/w glucose | $1^{st}$ |
| 2 | 8.28 | 50% w/w glucose | $1^{st}$ |
| 3 | 9.62 | 50% w/w glucose | $1^{st}$ |
| 4 | 11.18 | 50% w/w glucose | $1^{st}$ |
| 5 | 11.18 | 50% w/w glucose | $1^{st}$ |
| 6 | 11.18 | 50% w/w glucose | $1^{st}$ |
| 7 | 11.18 | 50% w/w glucose | $1^{st}$ |
| 8 | 11.18 | 50% w/w glucose | $1^{st}$ |
| 0 | 11.22 | 25% w/w lactose | $2^{nd}$ |
| 2 | 24.42 | 25% w/w lactose | $2^{nd}$ |
| 20 | 16.72 | 25% w/w lactose | $2^{nd}$ |
| 30 | 18.7 | 25% w/w lactose | $2^{nd}$ |
| 40 | 18.7 | 25% w/w lactose | $2^{nd}$ |

At the end of the fermentation, the agitation was reduced to 150 rpm, the aeration stopped and the temperature maintained at 35° C. Part of the fermentation broth was withdrawn, leaving ca. 180 kg in the fermenter. This remaining broth was titrated to pH 5.2 and maintained at this pH with 20% $H_2SO_4$ (20% w/w) and NaOH (50% w/w) while 9.0 L of aqueous glutaraldehyde (GA, 10% w/w) was added with stirring at a rate of ~90 mL/min; this rate of addition was equivalent to 50 mg glutaraldehyde/L fermentation broth/min, and the final concentration of glutaraldehyde was ca. 5 g glutaraldehyde/L (0.035 g glutaraldehyde/$OD_{550}$). After 5 h from initiation of glutaraldehyde addition to the broth, the pH was adjusted to 7.0, and 1.8 L of aqueous sodium bisulfate (10% w/w, pH 7) was added (ca. 1 g sodium bisulfite/L final concentration) with stirring, and the broth stirred for an additional 15 min. The temperature of the broth was then decreased to 10° C., and the agitation decreased to 100 rpm. The broth was concentrated to 40 kg of cell suspension using a Diskstack centrifuge (Alfa Laval), then 50 kg DI water (20° C.) was added to the suspension and the mixture was concentrated by centrifugation to produce 40 kg of washed cell suspension. The suspension (identified as NIT 188A-C2) was stored at 5° C., and a portion of the cell suspension was used directly for the preparation of an immobilized cell catalyst (Example 6). Nitrilase specific activity during each process step is summarized in Table 8.

TABLE 8

Nitrilase activity during different stages of GA and bisulfite treatment

| fermentation stage | BZN U/g dcw |
|---|---|
| pre GA treatment | 2819 |
| post GA | 3300 |
| post NaHSO3 | 2493 |

EXAMPLE 6

Immobilization of Glutaraldehyde Pretreated *E. coli* MG1655/pNM18-168V in GA/PEI-Cross-linked Carrageenan Beads The final cell suspension concentrate recovered from the glutaraldehyde and sodium bisulfite-treated fermentation broth of Example 5 was centrifuged at 5° C. The resulting cell pellet was re-suspended in a 5-fold by weight amount of 0.35 M potassium phosphate buffer (pH 7.2), and centrifugation of the resulting cell suspension at 5° C. produced a wet cell paste that was immobilized and chemically cross-linked with GA and PEI as described in Example 2. The resulting immobilized cell catalyst was identified as immobilized NIT 188A-C2.

EXAMPLE 7

Dehydration/Rehydration of Glutaraldehyde/polyethylenimine Cross-linked Carrageenan-immobilized Biocatalyst Prepared Using a Glutaraldehyde Pretreated *E. coli* MG1655/pNM18-168V *E. coli* MG1655/pSW138-F168V Transformant Glutaraldehyde/polyethylenimine cross-linked carrageenan-immobilized *E. coli* MG1655/pSW138-F168V transformant beads prepared as described in Example 6 using glutaraldehyde-pretreated cells were dehydrated in a vacuum oven (176 mm Hg) at 35° C. with nitrogen purge for 20, weighed, and dehydrated as before for an additional 4 h (total of 24 h). The ratio of final dehydrated bead weight to original (not dehydrated) bead weight was 0.217. The dehydrated beads were subsequently rehydrated by placing the beads in 20-fold (by weight) solution of 0.10 M ammonium glycolate (pH 7.3) at 5° C. for 72 h. The resulting rehydrated beads were washed twice with a 9-fold (by weight) solution of 0.10 M ammonium glycolate (pH 7.3), then weighed; the ratio of rehydrated bead weight to original (not dehydrated) bead weight was 0.578 for beads rehydrated at 5° C. The resulting biocatalyst was identified as immobilized NIT 188A-C2-D.

EXAMPLE 8

Specific Activity of Glutaraldehyde/polyethylenimine Cross-linked Carrageenan-immobilized *E. coli* MG1655/pSW138-F168V Biocatalyst Prepared Using a Glutaraldehyde Pretreated *E. coli* MG1655/pNM18-168V *E. coli* MG1655/pSW138-F168V Transformant, Before and After Immobilized Biocatalyst Dehydration/Rehydration In a typical procedure, duplicate sets of batch reactions for the conversion of glycolonitrile to glycolic acid were run in 50-mL jacketed reaction vessels equipped with overhead stirring and temperature control at 25 C. In a first set of duplicate reactions, each reaction vessel was charged with 4 g of GA/PEI-cross-linked *E. coli* MG1655/pSW138-168V/carrageenan beads (0.20 g dry cell weight; immobilized NIT 188A-C2, prepared as described in Example 6 (GA pretreatment of cells prior to immobilization)), 3.0 mL of aqueous ammonium glycolate (4.0 M, pH 7.0) and 7.75 mL of deionized, distilled water. In a second set of duplicate reactions, each reaction vessel was charged with 2.55 g of GA/PEI-cross-linked *E. coli* MG1655/pSW138-168V/carrageenan beads (0.20 g dry cell weight; immobilized NIT 188A-C2-D, prepared as described in Example 7 (GA pretreatment of cells prior to immobilization and subsequent dehydration/rehydration)), 3.0 mL of aqueous ammonium glycolate (4.0 M, pH 7.0) and 9.10 mL of deionized, distilled water.

Each reaction vessel was flushed with nitrogen, and the mixture stirred at 25° C. while programmable syringe pumps were used to simultaneously add 0.520 mL of 62 wt % glycolonitrile (GLN) in water (6.0 mmol GLN, 0.006 mmol formaldehyde; stabilized with 0.7 wt % glycolic acid)) and 0.150 mL of aqueous ammonium hydroxide (0.9375 wt % $NH_3$); one equivalent volume of GLN and ammonium hydroxide solutions were added simultaneously every 2 h (total of eight simultaneous additions of GLN solution and aqueous ammonium hydroxide) to maintain the concentration of GLN at $\leq$400 mM and the pH within a range of 7.0-7.5. Reaction samples (0.050 mL) were removed at predetermined times after the first GLN addition and added to 0.010 mL of 6.0 N HCl and 0.200 mL of 0.25 M iso-propanol in water (HPLC external standard), the resulting mixture centrifuged, and the supernatant analyzed by HPLC to determine the initial reaction rate and the catalyst specific activity ($\mu$mol glycolic acid/min/g dcw biocatalyst). At completion of the reaction, there was 100% conversion of GLN to produce glycolic acid (as the ammonium salt) in >99% yield. Table 9 lists the initial specific activities of the biocatalysts.

At the end of the first reaction, the aqueous product mixture was decanted from the catalyst (under nitrogen) in each reaction vessel, leaving a mixture of immobilized cell catalyst and remaining product solution. To the reaction vessel then added sufficient distilled, deionized water to reproduce the initial reaction volume in the first reaction prior to the addition of GLN and ammonium hydroxide solutions (ca. 15.3 mL initial reaction volume), and a second reaction was performed at 25° C. by the addition of aliquots of aqueous GLN and ammonium hydroxide as described immediately above. The specific activities of recovered biocatalyst in consecutive batch reactions with catalyst recycle are listed in Table 10.

TABLE 9

Specific Activity of Glutaraldehyde/polyethylenimine Cross-linked Carrageenan-immobilized *E. coli* MG1655/pSW138-F168V Biocatalyst Prepared Using a Glutaraldehyde Pretreated *E. coli* MG1655/pNM18-168V *E. coli* MG1655/pSW138-F168V Transformant

| immobilized cell biocatalyst | dehydration temperature (° C.) | rehydration temperature (° C.) | specific activity (U/g dcw) | activity after rehydration (%) |
|---|---|---|---|---|
| NIT 188A-C2 | none | none | 1826 | |
| NIT 188A-C2 | none | none | 1857 | |
| NIT 188A-C2-D | 35 | 5 | 1660 | 90 |
| NIT 188A-C2-D | 35 | 5 | 1584 | 86 |

TABLE 10

Recovered biocatalyst specific activity in consecutive batch reactions with biocatalyst recycle using a glutaraldehyde/PEI cross-linked carrageenan-immobilized microbial biocatalyst prepared using cells pretreated with glutaraldehyde.

| immobilized cell biocatalyst | dehydrated/ rehydrated immobilized cells | biocatalyst specific activity (GLN U/g dcw) in consecutive batch reactions | | | | decrease in specific activity, rxn1 to rxn4 (%) |
|---|---|---|---|---|---|---|
| | | reaction 1 | reaction 2 | reaction 3 | reaction 4 | |
| NIT 188C2 | no | 1826 | 1518 | 1596 | 1759 | 4 |
| NIT 188C2 | no | 1857 | 1656 | 1581 | 1947 | 0 |
| NIT 188C2-D | yes | 1660 | 1369 | 1472 | 1674 | 0 |
| NIT 188C2-D | yes | 1584 | 1392 | 1485 | 1417 | 10 |

EXAMPLE 9

Storage Stability of Glutaraldehyde/polyethylenimine Cross-linked Carrageenan-immobilized Biocatalyst Prepared Using a Glutaraldehyde Pretreated *E. coli* MG1655/pNM18-168V Transformant, Before and After Immobilized Biocatalyst Dehydration/Rehydration Freshly-prepared GA/PEI-cross-linked *E. coli* MG 1655/pSW138-168V/carrageenan beads (immobilized NIT 188A-C2, prepared as described in Example 6 (GA pretreatment of cells prior to immobilization)) were stored for 28 days in 1.0 M ammonium bicarbonate (pH 7.3) at 5° C. Dehydrated GA/PEI-cross-linked *E. coli* MG 1655/pSW138-168V/carrageenan beads (immobilized NIT 188A-C2, dehydrated as described in Example 7) were stored dry under nitrogen at 5° C. for 28 days, then rehydrated as described in Example 7. Prior to use, the biocatalysts were washed twice for 15 min with 180 mL of 0.1 M ammonium glycolate (pH 7.0) at room temperature, then evaluated in duplicate sets of consecutive batch reactions with biocatalyst recycle using the procedure described in Example 8. The specific activity of each biocatalyst in four consecutive batch reactions to convert glycolonitrile to ammonium glycolate is presented in Table 11.

TABLE 11

Specific activity in consecutive batch reactions with biocatalyst recycle using glutaraldehyde/PEI cross-linked, carrageenan-immobilized microbial catalyst prepared using cells pretreated with glutaraldehyde; biocatalyst stored for 28 days at 5° C., with or without dehydration.

| immobilized cell biocatalyst (glutaraldehyde pretreated cells) | biocatalyst specific activity in consecutive batch reactions (GLN U/g dcw) | | | | decrease in specific activity, rxn1 to rxn4 (%) |
|---|---|---|---|---|---|
| | reaction 1 | reaction 2 | reaction 3 | reaction 4 | |
| Not dehydrated | 1910 | 1455 | 1580 | 1543 | 19 |
| Not dehydrated | 1987 | 1434 | 1472 | 1783 | 10 |
| dehydrated/rehydrated | 1474 | 1467 | 1585 | 1318 | 11 |
| dehydrated/rehydrated | 1493 | 1412 | — | 1665 | 0 |

What is claimed is:

1. An isolated dehydrated enzyme catalyst having nitrilase activity with improved specific activity produced by a process comprising:
(a) producing an enzyme catalyst having nitrilase activity by fermentation, said enzyme catalyst comprising a polypeptide having an amino acid sequence selected from the group consisting of SEQ ID NOs: 4, 5, 6, 7, 8, 9, 10, 11, 12, 13, 14, 15, 16, 17, 18, 19, 20, 21, 22, 23, 24, 25, 27, 29, 31, 33, 35, 37, 39, 41, 43, 45, 47, 49, 51, 53, 55, and 57;
(b) pretreating said enzyme catalyst with glutaraldehyde;
(c) optionally inactivating unreacted glutaraldehyde with bisulfite following glutaraldehyde pretreatment;
(d) recovering the enzyme catalyst from (b) or (c) and immobilizing said enzyme catalyst in carrageenan;
(e) cross-linking the resulting carrageenan-immobilized enzyme catalyst of (d) with glutaraldehyde and polyethylenimine;
(f) producing a glutaraldehyde-pretreated immobilized and cross-linked enzyme catalyst, wherein said glutaraldehyde-pretreated immobilized and cross-linked enzyme catalyst has improved retention of initial specific activity during conversion of glycolonitrile to glycolic acid as compared to non-glutaraldehyde-pretreated immobilized and cross-linked enzyme catalysts under the same reaction conditions; and
(g) dehydrating the cross-linked immobilized enzyme catalyst produced in step (f).

2. The isolated dehydrated enzyme catalyst of claim 1, wherein said catalyst retains at least about 70% of its specific activity for hydrolyzing glycolonitrile to glycolic acid after rehydration.

3. The isolated dehydrated enzyme catalyst of claim 1 further comprising step (h) rehydrating the enzyme catalyst of step (g) in an aqueous solution.

4. The isolated dehydrated enzyme catalyst of claim 3 further comprising step (i) contacting the rehydrated enzyme catalyst of claim 3 with glycolonitrile in an aqueous solution under suitable reaction conditions whereby glycolic acid is produced.

5. The isolated dehydrated enzyme catalyst of claim 4 further comprising step (j) recovering the glycolic acid produced in step (i).

6. The isolated dehydrated enzyme catalyst of claim 1 wherein the pH is maintained between 5.0 and 9.0 during pretreatment with glutaraldehyde.

7. The isolated dehydrated enzyme catalyst of claim 1 wherein the pretreating with glutaraldehyde in step (b) comprises adding glutaraldehyde to a fermentation broth produced by step (a) in an amount in the range of about 3 g/L (0.025 g GA per $OD_{550}$) and about 5 g/L (0.042 g GA per $OD_{550}$).

8. The isolated dehydrated enzyme catalyst of claim 1 wherein the pretreating with glutaraldehyde in step (b) comprises adding glutaraldehyde to a fermentation broth produced by step (a) at a rate of 50 mg/L/h to 500 mg/L/h.

* * * * *

SEQUENCE LISTING

<160> NUMBER OF SEQ ID NOS: 57

<210> SEQ ID NO 1
<211> LENGTH: 12
<212> TYPE: PRT
<213> ORGANISM: artificial sequence
<220> FEATURE:
<223> OTHER INFORMATION: Catalytic signature motif
<220> FEATURE:
<221> NAME/KEY: MISC_FEATURE
<222> LOCATION: (2)..(2)
<223> OTHER INFORMATION: Xaa = Ala or Gly
<220> FEATURE:
<221> NAME/KEY: MISC_FEATURE
<222> LOCATION: (3)..(3)
<223> OTHER INFORMATION: Xaa = Leu, Val, or Ala
<220> FEATURE:
<221> NAME/KEY: MISC_FEATURE

```
<222> LOCATION: (4)..(3)
<223> OTHER INFORMATION: Xaa = Ala, Asn, Ile, Cys, Val, or Gln;
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa = His or Asn;
<220> FEATURE:
<221> NAME/KEY: MISC_FEATURE
<222> LOCATION: (9)..(9)
<223> OTHER INFORMATION: Xaa = Leu, Tyr, Phe, Ala, Met, Lys, Val, Thr,
      or Arg
<220> FEATURE:
<221> NAME/KEY: MISC_FEATURE
<222> LOCATION: (10)..(10)
<223> OTHER INFORMATION: Xaa = Asn, Gln, Met, Leu, or Ser;
<220> FEATURE:
<221> NAME/KEY: MISC_FEATURE
<222> LOCATION: (11)..(11)
<223> OTHER INFORMATION: Xaa = Pro or Thr
<220> FEATURE:
<221> NAME/KEY: MISC_FEATURE
<222> LOCATION: (12)..(12)
<223> OTHER INFORMATION: Xaa = Leu or Val

<400> SEQUENCE: 1

Gly Xaa Xaa Xaa Cys Trp Glu Xaa Xaa Xaa Xaa Xaa
 1               5                  10

<210> SEQ ID NO 2
<211> LENGTH: 12
<212> TYPE: PRT
<213> ORGANISM: artificial sequence
<220> FEATURE:
<223> OTHER INFORMATION: Catalytic sequence motif #2
<220> FEATURE:
<221> NAME/KEY: MISC_FEATURE
<222> LOCATION: (2)..(2)
<223> OTHER INFORMATION: Xaa = Ala or Gly
<220> FEATURE:
<221> NAME/KEY: MISC_FEATURE
<222> LOCATION: (4)..(4)
<223> OTHER INFORMATION: Xaa = Ala or Gly
<220> FEATURE:
<221> NAME/KEY: MISC_FEATURE
<222> LOCATION: (9)..(9)
<223> OTHER INFORMATION: Xaa = Leu, Tyr, Phe, Ala, Met, Lys, Val, Thr,
      or Arg
<220> FEATURE:
<221> NAME/KEY: MISC_FEATURE
<222> LOCATION: (10)..(10)
<223> OTHER INFORMATION: Xaa = Asn, Gln, Met, or Ser

<400> SEQUENCE: 2

Gly Xaa Leu Xaa Cys Trp Glu His Xaa Xaa Pro Leu
 1               5                  10

<210> SEQ ID NO 3
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)
<220> FEATURE:
<221> NAME/KEY: misc_feature
<222> LOCATION: (1)..(3)
<223> OTHER INFORMATION: Start codon TTG changed to ATG to facilitate
      recombinant expression

<400> SEQUENCE: 3
```

-continued

| | |
|---|---|
| atg gtt tcg tat aac agc aag ttc ctc gcg gca acc gtt cag gca gag<br>Met Val Ser Tyr Asn Ser Lys Phe Leu Ala Ala Thr Val Gln Ala Glu<br>1                      5                       10                  15 | 48 |
| ccg gta tgg ctc gac gca gac gca acg atc gac aag tcg atc ggc atc<br>Pro Val Trp Leu Asp Ala Asp Ala Thr Ile Asp Lys Ser Ile Gly Ile<br>              20                     25                     30 | 96 |
| atc gaa gaa gct gcc caa aag ggc gcg agt ctg atc gct ttc ccg gaa<br>Ile Glu Glu Ala Ala Gln Lys Gly Ala Ser Leu Ile Ala Phe Pro Glu<br>      35                   40                   45 | 144 |
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>50                       55                   60 | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65                       70                   75                   80 | 240 |
| ggt gac gac cgt atg cgt cgc ctc cag ctg gcc gcg cgc cgc aac aaa<br>Gly Asp Asp Arg Met Arg Arg Leu Gln Leu Ala Ala Arg Arg Asn Lys<br>                     85                   90                   95 | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>                  100                    105                  110 | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>         115                    120                  125 | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130                     135                  140 | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                     150                    155                  160 | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>                  165                    170                  175 | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>         180                    185                  190 | 576 |
| cct ctt cag ccg gat gtt ttc caa ctg agc atc gaa gcc aac gcg acg<br>Pro Leu Gln Pro Asp Val Phe Gln Leu Ser Ile Glu Ala Asn Ala Thr<br>                195                    200                  205 | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>210                     215                    220 | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                     230                    235                  240 | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                     245                    250                  255 | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>         260                    265                  270 | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>                275                    280                  285 | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290                     295                    300 | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305                     310                    315                  320 | 960 |

```
gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
            355                 360                 365 aag tag                                                            1110
Lys

<210> SEQ ID NO 4
<211> LENGTH: 369
<212> TYPE: PRT
<213> ORGANISM: Acidovorax facilis 72W

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
```

-continued

```
                290                 295                 300
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 5
<211> LENGTH: 356
<212> TYPE: PRT
<213> ORGANISM: Alcaligenes faecalis LM3

<400> SEQUENCE: 5

Met Gln Thr Arg Lys Ile Val Arg Ala Ala Val Gln Ala Ala Ser
1               5                   10                  15

Pro Asn Tyr Asp Leu Ala Thr Gly Val Asp Lys Thr Ile Glu Leu Ala
            20                  25                  30

Arg Gln Ala Arg Asp Glu Gly Cys Asp Leu Ile Val Phe Gly Glu Thr
        35                  40                  45

Trp Leu Pro Gly Tyr Pro Phe His Val Trp Leu Gly Ala Pro Ala Trp
    50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Gln Met Leu Trp Ser Arg Arg
        115                 120                 125

Lys Leu Lys Pro Thr His Val Glu Arg Thr Val Phe Gly Glu Gly Tyr
    130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Ser Leu Leu Lys Val Gly Gly Gly Ser Ser Met Ile Phe Ala
                245                 250                 255

Pro Asp Gly Arg Thr Leu Ala Pro Tyr Leu Pro His Asp Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
```

```
            290                 295                 300
Val Leu Asp Leu Gly His Arg Glu Pro Met Thr Arg Val His Ser Lys
305                 310                 315                 320

Ser Val Ile Gln Glu Glu Ala Pro Gly Pro His Val Gln Ser Thr Ala
                325                 330                 335

Ala Pro Val Ala Val Ser Gln Thr Gln Asp Ser Asp Thr Leu Leu Val
            340                 345                 350

Gln Glu Pro Ser
        355

<210> SEQ ID NO 6
<211> LENGTH: 366
<212> TYPE: PRT
<213> ORGANISM: Rhodococcus rhodochrous J1

<400> SEQUENCE: 6

Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
        35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Val Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Asp Asn
225                 230                 235                 240

Asp Glu Gln Arg Lys Leu Ile Gly Arg Gly Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300
```

```
Ser Leu Asn Phe Asn Gln Arg His Thr Thr Pro Val Asn Thr Ala Ile
305                 310                 315                 320

Ser Thr Ile His Ala Thr His Thr Leu Val Pro Gln Ser Gly Ala Leu
            325                 330                 335

Asp Gly Val Arg Glu Leu Asn Gly Ala Asp Glu Gln Arg Ala Leu Pro
        340                 345                 350

Ser Thr His Ser Asp Glu Thr Asp Arg Ala Thr Ala Ser Ile
        355                 360                 365
```

<210> SEQ ID NO 7
<211> LENGTH: 383
<212> TYPE: PRT
<213> ORGANISM: Rhodococcus rhodochrous K22

<400> SEQUENCE: 7

```
Met Ser Ser Asn Pro Glu Leu Lys Tyr Thr Gly Lys Val Lys Val Ala
1               5                   10                  15

Thr Val Gln Ala Glu Pro Val Ile Leu Asp Ala Asp Ala Thr Ile Asp
            20                  25                  30

Lys Ala Ile Gly Phe Ile Glu Glu Ala Ala Lys Asn Gly Ala Glu Phe
        35                  40                  45

Leu Ala Phe Pro Glu Val Trp Ile Pro Gly Tyr Pro Tyr Trp Ala Trp
    50                  55                  60

Ile Gly Asp Val Lys Trp Ala Val Ser Asp Phe Ile Pro Lys Tyr His
65                  70                  75                  80

Glu Asn Ser Leu Thr Leu Gly Asp Asp Arg Met Arg Arg Leu Gln Leu
                85                  90                  95

Ala Ala Arg Gln Asn Asn Ile Ala Leu Val Met Gly Tyr Ser Glu Lys
            100                 105                 110

Asp Gly Ala Ser Arg Tyr Leu Ser Gln Val Phe Ile Asp Gln Asn Gly
        115                 120                 125

Asp Ile Val Ala Asn Arg Arg Lys Leu Lys Pro Thr His Val Glu Arg
    130                 135                 140

Thr Ile Tyr Gly Glu Gly Asn Gly Thr Asp Phe Leu Thr His Asp Phe
145                 150                 155                 160

Gly Phe Gly Arg Val Gly Gly Leu Asn Cys Trp Glu His Phe Gln Pro
                165                 170                 175

Leu Ser Lys Tyr Met Met Tyr Ser Leu Asn Glu Gln Ile His Val Ala
            180                 185                 190

Ser Trp Pro Ala Met Phe Ala Leu Thr Pro Asp Val His Gln Leu Ser
        195                 200                 205

Val Glu Ala Asn Asp Thr Val Thr Arg Ser Tyr Ala Ile Glu Gly Gln
    210                 215                 220

Thr Phe Val Leu Ala Ser Thr His Val Ile Gly Lys Ala Thr Gln Asp
225                 230                 235                 240

Leu Phe Ala Gly Asp Asp Ala Lys Arg Ala Leu Leu Pro Leu Gly
                245                 250                 255

Gln Gly Trp Ala Arg Ile Tyr Gly Pro Asp Gly Lys Ser Leu Ala Glu
            260                 265                 270

Pro Leu Pro Glu Asp Ala Glu Gly Leu Leu Tyr Ala Glu Leu Asp Leu
        275                 280                 285

Glu Gln Ile Ile Leu Ala Lys Ala Ala Ala Asp Pro Ala Gly His Tyr
    290                 295                 300

Ser Arg Pro Asp Val Leu Ser Leu Lys Ile Asp Thr Arg Asn His Thr
305                 310                 315                 320
```

```
Pro Val Gln Tyr Ile Thr Ala Asp Gly Arg Thr Ser Leu Asn Ser Asn
                325                 330                 335

Ser Arg Val Glu Asn Tyr Arg Leu His Gln Leu Ala Asp Ile Glu Lys
            340                 345                 350

Tyr Glu Asn Ala Glu Ala Thr Leu Pro Leu Asp Ala Pro Ala Pro
        355                 360                 365

Ala Pro Ala Pro Glu Gln Lys Ser Gly Arg Ala Lys Ala Glu Ala
    370                 375                 380

<210> SEQ ID NO 8
<211> LENGTH: 381
<212> TYPE: PRT
<213> ORGANISM: Norcardia sp. C-14-1

<400> SEQUENCE: 8

Met Lys Val Ala Thr Val Gln Ala Glu Pro Val Ile Leu Asp Ala Asp
1               5                   10                  15

Ala Thr Ile Asp Lys Ala Ile Gly Tyr Ile Glu Ala Ser Lys Asn
            20                  25                  30

Gly Ala Glu Phe Ile Ala Phe Pro Glu Val Trp Ile Pro Gly Tyr Pro
        35                  40                  45

Tyr Trp Ala Trp Ile Gly Asp Val Lys Trp Ala Val Ser Glu Phe Ile
    50                  55                  60

Pro Lys Tyr His Glu Asn Ser Leu Thr Leu Gly Asp Asp Arg Met Arg
65                  70                  75                  80

Arg Leu Gln Leu Ala Ala Arg Gln His Asn Ile Ala Met Val Val Gly
                85                  90                  95

Tyr Ser Glu Lys Asp Gly Ala Ser Arg Tyr Leu Ser Gln Val Phe Ile
            100                 105                 110

Asp Gln Asn Gly Asp Ile Val Ala Asn Arg Arg Lys Leu Lys Pro Thr
        115                 120                 125

His Val Glu Arg Thr Ile Tyr Gly Glu Gly Asn Gly Thr Asp Phe Leu
    130                 135                 140

Thr His Asp Phe Gly Phe Gly Arg Val Gly Gly Leu Asn Cys Trp Glu
145                 150                 155                 160

His Phe Gln Pro Leu Ser Lys Tyr Met Met Tyr Ser Leu Asn Glu Gln
                165                 170                 175

Ile His Val Ala Ser Trp Pro Ala Met Phe Ala Leu Thr Pro Asp Val
            180                 185                 190

His Gln Leu Ser Val Glu Ala Asn Asp Thr Val Thr Arg Ser Tyr Ala
        195                 200                 205

Ile Glu Gly Gln Thr Phe Val Leu Ala Ala Thr His Val Ile Gly Lys
    210                 215                 220

Ala Thr Gln Asp Leu Phe Ala Gly Asp Glu Ala Lys Arg Ala Leu
225                 230                 235                 240

Leu Pro Leu Gly Gln Gly Trp Ala Arg Ile Tyr Gly Pro Asp Gly Lys
                245                 250                 255

Ser Leu Ala Glu Pro Leu Ala Glu Asn Ala Gly Leu Leu Tyr Ala
            260                 265                 270

Glu Leu Asp Leu Glu Gln Ile Ile Val Ala Lys Ala Ala Asp Pro
        275                 280                 285

Ala Gly His Tyr Ser Arg Pro Asp Val Leu Ser Leu Lys Val Asp Thr
    290                 295                 300

Arg Asn His Thr Pro Val Gln Tyr Val Thr Glu Asp Gly Gly Ser Ser
```

-continued

```
            305                 310                 315                 320
Leu Asn Ser Asn Ser Arg Val Glu Asn Tyr Arg Leu Arg Gln Leu Ala
                325                 330                 335
Asp Ile Glu Lys Tyr Glu Asn Ala Asp Ser Ala Thr Val Pro Leu Asp
            340                 345                 350
Val Thr Thr Pro Glu Lys Gln Ser Gly Asp Val Asn Ala Asn Gly Asn
        355                 360                 365
Ala Lys Val Asn Thr Asn Pro Ser Ala Lys Ala Lys Ala
    370                 375                 380

<210> SEQ ID NO 9
<211> LENGTH: 310
<212> TYPE: PRT
<213> ORGANISM: Bordetella bronchiseptica RB50

<400> SEQUENCE: 9

Met Thr Thr His Arg Ile Ala Val Ile Gln Asp Gly Pro Val Pro Gly
1               5                   10                  15
Asp Ala Met Ala Thr Ala Glu Lys Met Ser Arg Leu Ala Ala Ser Ala
            20                  25                  30
Lys Ala Gln Gly Ala Arg Leu Ala Leu Phe Pro Glu Ala Phe Val Gly
        35                  40                  45
Gly Tyr Pro Lys Gly Ala Asp Phe His Ile Phe Leu Gly Gly Arg Thr
    50                  55                  60
Pro Gln Gly Arg Ala Gln Tyr Gln Arg Tyr Ala Glu Thr Ala Ile Ala
65                  70                  75                  80
Val Pro Gly Pro Val Thr Glu Arg Ile Gly Gln Ile Ala Ala Glu Gln
                85                  90                  95
Asp Met Phe Ile Val Gly Val Ile Glu Arg Asp Gly Gly Thr Leu
            100                 105                 110
Tyr Cys Thr Ile Leu Phe Phe Ser Pro Glu Gly Glu Leu Leu Gly Lys
        115                 120                 125
His Arg Lys Leu Met Pro Thr Ala Leu Glu Arg Leu Leu Trp Gly Tyr
    130                 135                 140
Gly Asp Gly Ser Thr Phe Pro Val Tyr Asp Thr Pro Leu Gly Lys Leu
145                 150                 155                 160
Gly Ala Val Val Cys Trp Glu Asn Tyr Met Pro Leu Leu Arg Met Ala
                165                 170                 175
Met Tyr Gly Lys Gln Ile Gln Ile Tyr Cys Ala Pro Thr Ala Asp Asp
            180                 185                 190
Lys Pro Thr Trp Val Ser Thr Met Gln His Val Ala Leu Glu Gly Arg
        195                 200                 205
Cys Phe Val Leu Ser Ala Cys Gln His Leu Arg Gly Lys Asp Phe Pro
    210                 215                 220
Pro Glu Phe His Asn Ala Leu Asp Val Gln Pro Asp Thr Val Leu Met
225                 230                 235                 240
Arg Gly Gly Ser Cys Ile Val Asp Pro Met Gly Gln Leu Leu Ala Gly
                245                 250                 255
Pro Val Tyr Asp Glu Asp Ala Ile Leu Val Ala Asp Ile Asp Leu Asp
            260                 265                 270
Ala Val Thr Arg Gly Lys Met Asp Phe Asp Val Val Gly His Tyr Ala
        275                 280                 285
Arg Pro Asp Ile Phe Ser Leu Thr Val Asp Glu Arg Pro Lys Pro
    290                 295                 300
```

```
Val Thr Thr Leu Lys Pro
305             310

<210> SEQ ID NO 10
<211> LENGTH: 339
<212> TYPE: PRT
<213> ORGANISM: Arabidopsis thaliana

<400> SEQUENCE: 10

Met Ser Thr Ser Glu Asn Thr Pro Phe Asn Gly Val Ala Ser Ser Thr
1               5                   10                  15

Ile Val Arg Ala Thr Ile Val Gln Ala Ser Thr Val Tyr Asn Asp Thr
            20                  25                  30

Pro Ala Thr Leu Glu Lys Ala Asn Lys Phe Ile Val Glu Ala Ala Ser
        35                  40                  45

Lys Gly Ser Glu Leu Val Val Phe Pro Glu Ala Phe Ile Gly Gly Tyr
    50                  55                  60

Pro Arg Gly Phe Arg Phe Gly Leu Gly Val Gly Val His Asn Glu Glu
65                  70                  75                  80

Gly Arg Asp Glu Phe Arg Lys Tyr His Ala Ser Ala Ile Lys Val Pro
                85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125

Thr Ala Leu Phe Phe Ser Pro Gln Gly Gln Phe Leu Gly Lys His Arg
    130                 135                 140

Lys Leu Met Pro Thr Ser Leu Glu Arg Cys Ile Trp Gly Gln Gly Asp
145                 150                 155                 160

Gly Ser Thr Ile Pro Val Tyr Asp Thr Pro Ile Gly Lys Leu Gly Ala
                165                 170                 175

Ala Ile Cys Trp Glu Asn Arg Met Pro Leu Tyr Arg Thr Ala Leu Tyr
            180                 185                 190

Ala Lys Gly Ile Glu Leu Tyr Cys Ala Pro Thr Ala Asp Gly Ser Lys
        195                 200                 205

Glu Trp Gln Ser Ser Met Leu His Ile Ala Ile Glu Gly Gly Cys Phe
    210                 215                 220

Val Leu Ser Ala Cys Gln Phe Cys Leu Arg Lys Asp Phe Pro Asp His
225                 230                 235                 240

Pro Asp Tyr Leu Phe Thr Asp Trp Tyr Asp Lys Glu Pro Asp Ser
                245                 250                 255

Ile Val Ser Gln Gly Gly Ser Val Ile Ser Pro Leu Gly Gln Val
            260                 265                 270

Leu Ala Gly Pro Asn Phe Glu Ser Glu Gly Leu Ile Thr Ala Asp Leu
        275                 280                 285

Asp Leu Gly Asp Val Ala Arg Ala Lys Leu Tyr Phe Asp Ser Val Gly
    290                 295                 300

His Tyr Ser Arg Pro Asp Val Leu His Leu Thr Val Asn Glu His Pro
305                 310                 315                 320

Lys Lys Pro Val Thr Phe Ile Ser Lys Val Glu Lys Ala Glu Asp Asp
                325                 330                 335

Ser Asn Lys

<210> SEQ ID NO 11
<211> LENGTH: 334
```

US 7,867,748 B2
51                                    52
-continued

```
<212> TYPE: PRT
<213> ORGANISM: Synechococcus elongatus PCC 7942

<400> SEQUENCE: 11

Met Ala Asp Lys Ile Ile Val Ala Ala Ala Gln Ile Arg Pro Val Leu
1               5                   10                  15

Phe Ser Leu Glu Gly Ser Val Ala Arg Val Leu Ala Ala Met Ala Glu
            20                  25                  30

Ala Ala Ala Ala Gly Val Gln Leu Ile Val Phe Pro Glu Thr Phe Leu
        35                  40                  45

Pro Tyr Tyr Pro Tyr Phe Ser Phe Val Glu Pro Val Leu Met Gly
    50                  55                  60

Arg Ser His Leu Lys Leu Tyr Glu Gln Ala Phe Thr Met Thr Gly Pro
65                  70                  75                  80

Glu Leu Gln Gln Ile Ala Arg Ala Ala Arg Gln His Arg Leu Phe Val
                85                  90                  95

Leu Leu Gly Val Asn Glu Arg Asp Gly Gly Ser Leu Tyr Asn Thr Gln
            100                 105                 110

Leu Leu Ile Ser Asp Gln Gly Asp Leu Leu Leu Lys Arg Arg Lys Ile
        115                 120                 125

Thr Pro Thr Tyr His Glu Arg Met Val Trp Gly Gln Gly Gly Gly Ala
    130                 135                 140

Gly Leu Thr Val Val Glu Thr Val Leu Gly Lys Val Gly Ala Leu Ala
145                 150                 155                 160

Cys Trp Glu His Tyr Asn Pro Leu Ala Arg Phe Ser Leu Met Thr Gln
                165                 170                 175

Gly Glu Glu Ile His Cys Ala Gln Phe Pro Gly Ser Leu Val Gly Pro
            180                 185                 190

Ile Phe Ser Glu Gln Thr Ala Val Thr Leu Arg His His Ala Leu Glu
        195                 200                 205

Ala Gly Cys Phe Val Leu Ser Ser Thr Ala Trp Leu Asp Pro Ala Asp
    210                 215                 220

Tyr Asp Thr Ile Thr Pro Asp Arg Ser Leu His Lys Ala Phe Gln Gly
225                 230                 235                 240

Gly Cys His Thr Ala Ile Ile Ser Pro Glu Gly Arg Tyr Leu Ala Gly
                245                 250                 255

Pro Leu Pro Glu Gly Glu Gly Leu Ala Ile Ala Glu Leu Asp Lys Ser
            260                 265                 270

Leu Ile Thr Lys Arg Lys Arg Met Met Asp Ser Val Gly His Tyr Ser
        275                 280                 285

Arg Pro Asp Leu Leu Ser Leu Arg Ile Asn Arg Ser Pro Ala Thr Gln
    290                 295                 300

Val Gln Ala Ile Gly Ser Ala Ala Ala Leu Pro Glu Leu Pro Asn Leu
305                 310                 315                 320

Glu Ala Ala Pro Ala Glu Thr Ala Glu Asp Tyr Leu His Ala
                325                 330

<210> SEQ ID NO 12
<211> LENGTH: 334
<212> TYPE: PRT
<213> ORGANISM: Synechococcus elongatus PCC 6301

<400> SEQUENCE: 12

Met Ala Asp Lys Ile Ile Val Ala Ala Ala Gln Ile Arg Pro Val Leu
1               5                   10                  15
```

```
Phe Ser Leu Glu Gly Ser Val Ala Arg Val Leu Ala Ala Met Ala Glu
            20                  25                  30

Ala Ala Ala Ala Gly Val Gln Leu Ile Val Phe Pro Glu Thr Phe Leu
        35                  40                  45

Pro Tyr Tyr Pro Tyr Phe Ser Phe Val Glu Pro Val Leu Met Gly
    50                  55                  60

Arg Ser His Leu Lys Leu Tyr Glu Gln Ala Phe Thr Met Thr Gly Pro
65                  70                  75                  80

Glu Leu Gln Gln Ile Ala Arg Ala Ala Arg Gln His Arg Leu Phe Val
                85                  90                  95

Leu Leu Gly Val Asn Glu Arg Asp Gly Gly Ser Leu Tyr Asn Thr Gln
                100                 105                 110

Leu Leu Ile Ser Asp Gln Gly Asp Leu Leu Lys Arg Arg Lys Ile
            115                 120                 125

Thr Pro Thr Tyr His Glu Arg Met Val Trp Gly Gln Gly Gly Gly Ala
    130                 135                 140

Gly Leu Thr Val Val Glu Thr Val Leu Gly Lys Val Gly Ala Leu Ala
145                 150                 155                 160

Cys Trp Glu His Tyr Asn Pro Leu Ala Arg Phe Ser Leu Met Thr Gln
                165                 170                 175

Gly Glu Glu Ile His Cys Ala Gln Phe Pro Gly Ser Leu Val Gly Pro
                180                 185                 190

Ile Phe Ser Glu Gln Thr Ala Val Thr Leu Arg His His Ala Leu Glu
            195                 200                 205

Ala Gly Cys Phe Val Leu Ser Ser Thr Ala Trp Leu Asp Pro Ala Asp
        210                 215                 220

Tyr Asp Thr Ile Thr Pro Asp Arg Ser Leu His Lys Ala Phe Gln Gly
225                 230                 235                 240

Gly Cys His Thr Ala Ile Ile Ser Pro Glu Gly Arg Tyr Leu Ala Gly
                245                 250                 255

Pro Leu Pro Glu Gly Glu Gly Leu Ala Ile Ala Glu Leu Asp Lys Ser
                260                 265                 270

Leu Ile Thr Lys Arg Lys Arg Met Met Asp Ser Val Gly His Tyr Ser
            275                 280                 285

Arg Pro Asp Leu Leu Ser Leu Arg Ile Asn Arg Ser Pro Ala Thr Gln
    290                 295                 300

Val Gln Ala Ile Gly Ser Ala Ala Ala Leu Pro Glu Leu Pro Asn Leu
305                 310                 315                 320

Glu Ala Ala Pro Ala Glu Thr Ala Glu Asp Tyr Leu His Ala
                325                 330

<210> SEQ ID NO 13
<211> LENGTH: 346
<212> TYPE: PRT
<213> ORGANISM: Synechocystis sp. PCC 6803

<400> SEQUENCE: 13

Met Leu Gly Lys Ile Met Leu Asn Tyr Thr Lys Asn Ile Arg Ala Ala
1               5                   10                  15

Ala Ala Gln Ile Ser Pro Val Leu Phe Ser Gln Gln Gly Thr Met Glu
            20                  25                  30

Lys Val Leu Asp Ala Ile Ala Asn Ala Ala Lys Lys Gly Val Glu Leu
        35                  40                  45

Ile Val Phe Pro Glu Thr Phe Val Pro Tyr Tyr Pro Tyr Phe Ser Phe
    50                  55                  60
```

Val Glu Pro Pro Val Leu Met Gly Lys Ser His Leu Lys Leu Tyr Gln
65                  70                  75                  80

Glu Ala Val Thr Val Pro Gly Lys Val Thr Gln Ala Ile Ala Gln Ala
            85                  90                  95

Ala Lys Thr His Gly Met Val Val Leu Gly Val Asn Glu Arg Glu
        100                 105                 110

Glu Gly Ser Leu Tyr Asn Thr Gln Leu Ile Phe Asp Ala Asp Gly Ala
            115                 120                 125

Leu Val Leu Lys Arg Arg Lys Ile Thr Pro Thr Tyr His Glu Arg Met
        130                 135                 140

Val Trp Gly Gln Gly Asp Gly Ala Gly Leu Arg Thr Val Asp Thr Thr
145                 150                 155                 160

Val Gly Arg Leu Gly Ala Leu Ala Cys Trp Glu His Tyr Asn Pro Leu
            165                 170                 175

Ala Arg Tyr Ala Leu Met Ala Gln His Glu Gln Ile His Cys Gly Gln
        180                 185                 190

Phe Pro Gly Ser Met Val Gly Gln Ile Phe Ala Asp Gln Met Glu Val
        195                 200                 205

Thr Met Arg His His Ala Leu Glu Ser Gly Cys Phe Val Ile Asn Ala
210                 215                 220

Thr Gly Trp Leu Thr Ala Glu Gln Lys Leu Gln Ile Thr Thr Asp Glu
225                 230                 235                 240

Lys Met His Gln Ala Leu Ser Gly Gly Cys Tyr Thr Ala Ile Ile Ser
            245                 250                 255

Pro Glu Gly Lys His Leu Cys Glu Pro Ile Ala Glu Gly Glu Gly Leu
        260                 265                 270

Ala Ile Ala Asp Leu Asp Phe Ser Leu Ile Ala Lys Arg Lys Arg Met
        275                 280                 285

Met Asp Ser Val Gly His Tyr Ala Arg Pro Asp Leu Leu Gln Leu Thr
290                 295                 300

Leu Asn Asn Gln Pro Trp Ser Ala Leu Glu Ala Asn Pro Val Thr Pro
305                 310                 315                 320

Asn Ala Ile Pro Ala Val Ser Asp Pro Glu Leu Thr Glu Thr Ile Glu
            325                 330                 335

Ala Leu Pro Asn Asn Pro Ile Phe Ser His
        340                 345

<210> SEQ ID NO 14
<211> LENGTH: 307
<212> TYPE: PRT
<213> ORGANISM: Pseudomonas entomophila L48

<400> SEQUENCE: 14

Met Pro Lys Ser Ile Val Ala Ala Leu Gln Val Gly Ser Leu Pro Glu
1               5                   10                  15

Gly Lys Ala Ala Thr Leu Glu Gln Ile Leu Gly Tyr Glu Gln Ala Ile
            20                  25                  30

Arg Glu Ala Gly Ala Arg Leu Val Met Pro Glu Ala Leu Leu Gly
        35                  40                  45

Gly Tyr Pro Lys Gly Glu Gly Phe Gly Thr Gln Leu Gly Tyr Arg Leu
        50                  55                  60

Pro Glu Gly Arg Glu Ala Phe Ala Arg Tyr Phe Ala Asn Ala Ile Asp
65                  70                  75                  80

Val Pro Gly Ser Glu Thr Ala Ala Leu Ala Gly Leu Ser Ala Arg Thr

```
                    85                  90                  95
Gly Ala Ser Leu Val Leu Gly Val Ile Glu Arg Ser Gly Asn Thr Leu
            100                 105                 110
Tyr Cys Thr Val Leu Phe Phe Glu Pro Glu Gly Gly Leu Val Ala Lys
        115                 120                 125
His Arg Lys Leu Met Pro Thr Gly Thr Glu Arg Leu Ile Trp Gly Lys
    130                 135                 140
Gly Asp Gly Ser Thr Leu Pro Val Val Asp Gly Arg Ala Gly Arg Ile
145                 150                 155                 160
Gly Ala Ala Val Cys Trp Glu Asn Tyr Met Pro Leu Leu Arg Thr Ala
                165                 170                 175
Met Tyr Ala Lys Gly Val Gln Leu Trp Cys Ala Pro Thr Val Asp Glu
            180                 185                 190
Arg Glu Leu Trp Gln Val Ser Met Arg His Val Ala Ala Glu Gly Arg
        195                 200                 205
Cys Phe Val Ile Ser Ala Cys Gln Val Gln Asp Ser Pro Ala Ala Leu
    210                 215                 220
Gly Met Glu Val Ala Asn Trp Pro Ala Glu Arg Pro Leu Ile Asn Gly
225                 230                 235                 240
Gly Ser Leu Ile Val Gly Pro Leu Gly Asp Val Leu Ala Gly Pro Leu
                245                 250                 255
Leu Gly Ala Arg Gly Leu Val Cys Ala Glu Val Asp Thr Asp Glu Leu
            260                 265                 270
Val Arg Ala Arg Tyr Asp Phe Asp Val Val Gly His Tyr Ala Arg Pro
        275                 280                 285
Asp Val Phe Glu Leu Ser Val Asp Glu Arg Pro Arg Pro Gly Val Arg
    290                 295                 300
Phe Ile Gly
305

<210> SEQ ID NO 15
<211> LENGTH: 329
<212> TYPE: PRT
<213> ORGANISM: Zymomonas mobilis subsp. mobilis ZM4

<400> SEQUENCE: 15

Met Ser Cys His Arg Val Ala Val Ile Gln Ala Gly Thr Ser Leu Phe
1               5                   10                  15
Asp Thr Glu Lys Thr Leu Asp Arg Met Glu Ala Leu Cys Arg Gln Ala
            20                  25                  30
Ala Glu Gln Asn Val Glu Leu Ala Val Phe Pro Glu Ala Tyr Ile Gly
        35                  40                  45
Gly Tyr Pro Lys Gly Leu Asp Phe Gly Ala Arg Met Gly Thr Arg Thr
    50                  55                  60
Glu Ala Gly Arg Glu Asp Phe Leu Arg Tyr Trp Lys Ala Ala Ile Asp
65                  70                  75                  80
Val Pro Gly Lys Glu Thr Ala Arg Ile Gly Ser Phe Ala Ala Lys Met
                85                  90                  95
Lys Ala Tyr Leu Val Val Gly Val Ile Glu Arg Ser Glu Ala Thr Leu
            100                 105                 110
Tyr Cys Thr Ala Leu Phe Phe Ala Pro Asp Gly Thr Leu Ile Gly Lys
        115                 120                 125
His Arg Lys Leu Met Pro Thr Ala Thr Glu Arg Leu Val Trp Gly Gln
    130                 135                 140
```

```
Gly Asp Gly Ser Thr Ile Glu Ile Leu Asp Thr Ala Val Gly Lys Leu
145                 150                 155                 160

Gly Ala Ala Ile Cys Trp Glu Asn Tyr Met Pro Val Leu Arg Gln Val
            165                 170                 175

Met Tyr Ala Gly Gly Val Asn Ile Trp Cys Ala Pro Thr Val Asp Gln
        180                 185                 190

Arg Glu Ile Trp Gln Val Ser Met Arg His Ile Ala Tyr Glu Gly Arg
    195                 200                 205

Leu Phe Val Leu Ser Ala Cys Gln Tyr Met Thr Arg Ala Asp Ala Pro
210                 215                 220

Ala Asp Tyr Asp Cys Ile Gln Gly Asn Asp Pro Glu Thr Glu Leu Ile
225                 230                 235                 240

Ala Gly Gly Ser Val Ile Ile Asp Pro Met Gly Asn Ile Leu Ala Gly
                245                 250                 255

Pro Leu Tyr Gly Gln Glu Gly Val Leu Val Ala Asp Ile Asp Leu Ser
            260                 265                 270

Asp Thr Ile Lys Ala Arg Tyr Asp Leu Asp Val Ser Gly His Tyr Gly
        275                 280                 285

Arg Pro Asp Ile Phe Glu Ile Lys Val Asp Arg Gln Ser His Gln Val
    290                 295                 300

Ile Thr Asp Gln Phe Ser Arg Asp Gln Ala Thr Glu Lys Lys Pro Val
305                 310                 315                 320

Ser Asp Ser Glu Ile Ser Gln Leu Asp
                325

<210> SEQ ID NO 16
<211> LENGTH: 339
<212> TYPE: PRT
<213> ORGANISM: Bacillus sp. OxB-1

<400> SEQUENCE: 16

Met Ser Asn Tyr Pro Lys Tyr Arg Val Ala Ala Val Gln Ala Ser Pro
1               5                   10                  15

Val Leu Leu Asp Leu Asp Ala Thr Ile Asp Lys Thr Cys Arg Leu Val
            20                  25                  30

Asp Glu Ala Ala Ala Asn Gly Ala Lys Val Ile Ala Phe Pro Glu Ala
        35                  40                  45

Phe Ile Pro Gly Tyr Pro Trp Trp Ile Trp Leu Gly Asn Ala Asp Tyr
    50                  55                  60

Gly Met Lys Tyr Tyr Ile Gln Leu Tyr Lys Asn Ser Val Glu Ile Pro
65                  70                  75                  80

Ser Leu Ala Val Gln Lys Leu Ser Ser Ala Gly Thr Asn Lys Val Tyr
                85                  90                  95

Phe Cys Val Ser Val Thr Glu Lys Asp Gly Gly Ser Leu Tyr Leu Thr
            100                 105                 110

Gln Leu Trp Phe Asp Pro Asn Gly Asp Leu Ile Gly Lys His Arg Lys
        115                 120                 125

Leu Lys Ala Thr Asn Ala Glu Lys Thr Ile Trp Gly Asp Gly Asp Gly
    130                 135                 140

Ser Met Met Pro Val Phe Glu Thr Glu Phe Gly Asn Leu Gly Gly Leu
145                 150                 155                 160

Gln Cys Trp Glu His Phe Leu Pro Leu Asn Val Ala Ala Met Ala Ser
                165                 170                 175

Met Asn Glu Gln Val His Val Ala Ser Trp Pro Ile Gly Met Pro Gln
            180                 185                 190
```

```
Glu Gly His Leu Phe Gly Pro Glu Gln Cys Val Thr Ala Thr Lys Tyr
            195                 200                 205

Tyr Ala Ile Ser Asn Gln Val Phe Cys Leu Leu Ser Ser Gln Ile Trp
210                 215                 220

Thr Glu Glu Gln Arg Asp Lys Ile Cys Glu Thr Glu Gln Arg Asn
225                 230                 235                 240

Phe Met Lys Val Gly His Gly Phe Ser Lys Ile Ile Ala Pro Asn Gly
                    245                 250                 255

Met Glu Ile Gly Asn Lys Leu Ala His Asp Glu Glu Gly Ile Thr Tyr
                260                 265                 270

Ala Asp Ile Asp Leu Glu Gln Ile Ile Pro Gly Lys Phe Leu Ile Asp
            275                 280                 285

Ser Ala Gly His Tyr Ser Thr Pro Gly Phe Leu Ser Leu Ser Phe Asp
        290                 295                 300

Arg Thr Glu Lys Lys Pro Ile Lys His Ile Gly Glu Ser Ala Gln Glu
305                 310                 315                 320

Thr Val Thr Tyr Glu Glu Ile Gln Tyr Gly Asn Lys Ala Asn Val Lys
                    325                 330                 335

Val His Ser

<210> SEQ ID NO 17
<211> LENGTH: 354
<212> TYPE: PRT
<213> ORGANISM: Comamonas testosterone

<400> SEQUENCE: 17

Met Lys Asn Tyr Pro Thr Val Lys Val Ala Ala Val Gln Ala Ala Pro
1               5                   10                  15

Val Phe Met Asn Leu Glu Ala Thr Val Asp Lys Thr Cys Lys Leu Ile
                20                  25                  30

Ala Glu Ala Ala Ser Met Gly Ala Lys Val Ile Gly Phe Pro Glu Ala
            35                  40                  45

Phe Ile Pro Gly Tyr Pro Tyr Trp Ile Trp Thr Ser Asn Met Asp Phe
    50                  55                  60

Thr Gly Met Met Trp Ala Val Leu Phe Lys Asn Ala Ile Glu Ile Pro
65                  70                  75                  80

Ser Lys Glu Val Gln Gln Ile Ser Asp Ala Ala Lys Lys Asn Gly Val
                85                  90                  95

Tyr Val Cys Val Ser Val Ser Glu Lys Asp Asn Ala Ser Leu Tyr Leu
            100                 105                 110

Thr Gln Leu Trp Phe Asp Pro Asn Gly Asn Leu Ile Gly Lys His Arg
        115                 120                 125

Lys Phe Lys Pro Thr Ser Ser Glu Arg Ala Val Trp Gly Asp Gly Asp
    130                 135                 140

Gly Ser Met Ala Pro Val Phe Lys Thr Glu Tyr Gly Asn Leu Gly Gly
145                 150                 155                 160

Leu Gln Cys Trp Glu His Ala Leu Pro Leu Asn Ile Ala Ala Met Gly
                165                 170                 175

Ser Leu Asn Glu Gln Val His Val Ala Ser Trp Pro Ala Phe Val Pro
            180                 185                 190

Lys Gly Ala Val Ser Ser Arg Val Ser Ser Val Cys Ala Ser Thr
        195                 200                 205

Asn Ala Met His Gln Ile Ile Ser Gln Phe Tyr Ala Ile Ser Asn Gln
    210                 215                 220
```

Val Tyr Val Ile Met Ser Thr Asn Leu Val Gly Gln Asp Met Ile Asp
225                 230                 235                 240

Met Ile Gly Lys Asp Glu Phe Ser Lys Asn Phe Leu Pro Leu Gly Ser
            245                 250                 255

Gly Asn Thr Ala Ile Ile Ser Asn Thr Gly Glu Ile Leu Ala Ser Ile
            260                 265                 270

Pro Gln Asp Ala Glu Gly Ile Ala Val Ala Glu Ile Asp Leu Asn Gln
            275                 280                 285

Ile Ile Tyr Gly Lys Trp Leu Leu Asp Pro Ala Gly His Tyr Ser Thr
290                 295                 300

Pro Gly Phe Leu Ser Leu Thr Phe Asp Gln Ser Glu His Val Pro Val
305                 310                 315                 320

Lys Lys Ile Gly Glu Gln Thr Asn His Phe Ile Ser Tyr Glu Asp Leu
            325                 330                 335

His Glu Asp Lys Met Asp Met Leu Thr Ile Pro Pro Arg Arg Val Ala
            340                 345                 350

Thr Ala

<210> SEQ ID NO 18
<211> LENGTH: 332
<212> TYPE: PRT
<213> ORGANISM: Synechococcus sp. CC9605

<400> SEQUENCE: 18

Met Thr Thr Val Lys Val Ala Ala Ala Gln Ile Arg Pro Val Leu Phe
1               5                   10                  15

Ser Leu Asp Gly Ser Leu Gln Lys Val Leu Asp Ala Met Ala Glu Ala
            20                  25                  30

Ala Ala Gln Gly Val Glu Leu Ile Val Phe Pro Glu Thr Phe Leu Pro
        35                  40                  45

Tyr Tyr Pro Tyr Phe Ser Phe Val Glu Pro Pro Val Leu Met Gly Arg
50                  55                  60

Ser His Leu Ala Leu Tyr Glu Gln Ala Val Val Pro Gly Pro Val
65                  70                  75                  80

Thr Asp Ala Val Ala Ala Ala Ser Gln Tyr Gly Met Gln Val Leu
                85                  90                  95

Leu Gly Val Asn Glu Arg Asp Gly Gly Thr Leu Tyr Asn Thr Gln Leu
            100                 105                 110

Leu Phe Asn Ser Cys Gly Glu Leu Val Leu Lys Arg Arg Lys Ile Thr
        115                 120                 125

Pro Thr Tyr His Glu Arg Met Val Trp Gly Gln Gly Asp Gly Ser Gly
130                 135                 140

Leu Lys Val Val Gln Thr Pro Leu Ala Arg Val Gly Ala Leu Ala Cys
145                 150                 155                 160

Trp Glu His Tyr Asn Pro Leu Ala Arg Tyr Ala Leu Met Ala Gln Gly
                165                 170                 175

Glu Glu Ile His Cys Ala Gln Phe Pro Gly Ser Leu Val Gly Pro Ile
            180                 185                 190

Phe Thr Glu Gln Thr Ala Val Thr Met Arg His His Ala Leu Glu Ala
        195                 200                 205

Gly Cys Phe Val Ile Cys Ser Thr Gly Trp Leu His Pro Asp Asp Tyr
210                 215                 220

Ala Ser Ile Thr Ser Glu Ser Gly Leu His Lys Ala Phe Gln Gly Gly
225                 230                 235                 240

```
Cys His Thr Ala Val Ile Ser Pro Glu Gly Arg Tyr Leu Ala Gly Pro
                245                 250                 255

Leu Pro Asp Gly Glu Gly Leu Ala Ile Ala Asp Leu Asp Leu Ala Leu
            260                 265                 270

Ile Thr Lys Arg Lys Arg Met Met Asp Ser Val Gly His Tyr Ser Arg
        275                 280                 285

Pro Glu Leu Leu Ser Leu Gln Ile Asn Ser Ser Pro Ala Val Pro Val
    290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330

<210> SEQ ID NO 19
<211> LENGTH: 306
<212> TYPE: PRT
<213> ORGANISM: Pseudomonas fluorescens Pf-5

<400> SEQUENCE: 19

Met Pro Lys Ser Val Val Ala Ala Leu Gln Ile Gly Ala Leu Pro Glu
1               5                   10                  15

Gly Lys Ala Ala Thr Leu Glu Gln Ile Leu Ser Tyr Glu Ala Ala Ile
            20                  25                  30

Ile Glu Ala Gly Ala Gln Leu Val Val Met Pro Glu Ala Leu Leu Gly
        35                  40                  45

Gly Tyr Pro Lys Gly Glu Gly Phe Gly Thr Gln Leu Gly Tyr Arg Leu
    50                  55                  60

Pro Glu Gly Arg Glu Ala Phe Ala Arg Tyr Phe Ala Asn Ala Ile Glu
65                  70                  75                  80

Val Pro Gly Val Glu Thr Asp Ala Leu Ala Ala Leu Ser Ala Arg Thr
                85                  90                  95

Gly Ala Asn Leu Val Leu Gly Val Ile Glu Arg Ser Gly Ser Thr Leu
            100                 105                 110

Tyr Cys Thr Ala Leu Tyr Phe Asp Pro Gln Gln Gly Leu Ser Gly Lys
        115                 120                 125

His Arg Lys Leu Met Pro Thr Gly Thr Glu Arg Leu Ile Trp Gly Lys
    130                 135                 140

Gly Asp Gly Ser Thr Leu Pro Val Leu Asp Thr Gln Val Gly Arg Val
145                 150                 155                 160

Gly Ala Val Ile Cys Trp Glu Asn Met Met Pro Leu Leu Arg Thr Ala
                165                 170                 175

Met Tyr Ala Gln Gly Ile Glu Val Trp Cys Ala Pro Thr Val Asp Glu
            180                 185                 190

Arg Glu Met Trp Gln Val Ser Met Arg His Ile Ala His Glu Gly Arg
        195                 200                 205

Cys Phe Val Val Ser Ala Cys Gln Val Gln Ala Ser Pro Glu Glu Leu
    210                 215                 220

Gly Leu Glu Ile Ala Asn Trp Pro Ala Gln Arg Pro Leu Ile Ala Gly
225                 230                 235                 240

Gly Ser Val Ile Val Gly Pro Met Gly Asp Val Leu Ala Gly Pro Leu
                245                 250                 255

Val Gly Arg Ala Gly Leu Ile Ser Ala Gln Ile Asp Thr Ala Asp Leu
            260                 265                 270

Val Arg Ala Arg Tyr Asp Tyr Asp Val Val Gly His Tyr Ala Arg Pro
```

```
                275                 280                 285
Asp Val Phe Glu Leu Thr Val Asp Gln Arg Pro Arg Pro Gly Val Arg
    290                 295                 300

Phe Thr
305

<210> SEQ ID NO 20
<211> LENGTH: 336
<212> TYPE: PRT
<213> ORGANISM: Nocardia farcinica IFM 10152]

<400> SEQUENCE: 20

Met Ser Gln Arg Asp Ser Phe Arg Ala Ala Val Gln Ala Ala Ala Pro
1               5                   10                  15

Val Trp Leu Asp Gly Ala Ala Thr Val Asp Lys Cys Val Ala Leu Ile
            20                  25                  30

Glu Glu Ala Ala Asp Asn Gly Ala Ala Leu Ile Ala Phe Pro Glu Thr
        35                  40                  45

Phe Val Pro Gly Tyr Pro Trp Trp Leu Trp Leu Asp Ser Pro Ala Trp
    50                  55                  60

Gly Met Gln Phe Val Ala Arg Tyr Phe Asp Asn Ser Leu Ala Leu Asp
65                  70                  75                  80

Gly Pro Leu Phe Ala Arg Leu Arg Glu Ala Ala Arg Arg Ser Ala Ile
                85                  90                  95

Thr Val Val Thr Gly His Ser Glu Arg Asp Gly Gly Ser Leu Tyr Met
            100                 105                 110

Gly Gln Ala Ile Ile Gly Ala Asp Gly Glu Val Leu Ala Ala Arg Arg
        115                 120                 125

Lys Leu Lys Pro Thr His Val Glu Arg Thr Val Phe Gly Glu Ser Asp
    130                 135                 140

Gly Ser Asn Leu Thr Val Val Asp Thr Glu Leu Gly Arg Leu Gly Ala
145                 150                 155                 160

Leu Cys Cys Trp Glu His Leu Gln Pro Leu Thr Lys Tyr Ala Met Tyr
                165                 170                 175

Ser Gln His Glu Gln Ile His Val Ala Ala Trp Pro Ser Phe Ser Val
            180                 185                 190

Tyr Arg Gly Ala Ala Tyr Ala Leu Gly Pro Glu Val Asn Thr Gly Ala
        195                 200                 205

Ala Arg Gln Tyr Ala Val Glu Gly Gln Cys Phe Val Leu Ser Pro Cys
    210                 215                 220

Ala Val Ile Asp Glu Ala Gly Val Glu Leu Phe Cys Asp Thr Pro Ala
225                 230                 235                 240

Lys Arg Glu Leu Leu Pro Gly Gly Gly Phe Ala Gln Ile Tyr Gly
                245                 250                 255

Pro Asp Gly Arg Glu Leu Gly Thr Ala Leu Pro Glu Thr Glu Glu Gly
            260                 265                 270

Leu Val Tyr Ala Asp Leu Glu Ala Ser Ala Val Ala Val Ala Lys Ser
        275                 280                 285

Ala Ala Asp Pro Val Gly His Tyr Ser Arg Pro Asp Val Leu Gln Leu
    290                 295                 300

Leu Trp Asp Pro Arg Pro Arg Ser Val Val Arg Gln Val Ala Leu Ser
305                 310                 315                 320

Val Ala Ser Pro Ala Glu Ser Ala Asp Asp Ala Glu Pro Ala Val Arg
                325                 330                 335
```

<210> SEQ ID NO 21
<211> LENGTH: 356
<212> TYPE: PRT
<213> ORGANISM: Alcaligenes faecalis 1650

<400> SEQUENCE: 21

Met Gln Thr Arg Lys Ile Val Arg Ala Ala Val Gln Ala Ser
1               5                   10                  15

Pro Asn Tyr Asp Leu Ala Thr Gly Val Asp Lys Thr Ile Glu Leu Ala
            20                  25                  30

Arg Gln Ala Arg Asp Glu Gly Cys Asp Leu Ile Val Phe Gly Glu Thr
        35                  40                  45

Trp Leu Pro Gly Tyr Pro Phe His Val Trp Leu Gly Ala Pro Ala Trp
    50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Glu Met Leu Trp Ser Arg Arg
        115                 120                 125

Lys Leu Lys Pro Thr His Val Glu Arg Thr Val Phe Gly Glu Gly Tyr
    130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Pro Leu Leu Lys Val Gly Gly Gly Ser Ser Met Ile Phe Ala
                245                 250                 255

Pro Asp Gly Arg Thr Leu Ala Pro Tyr Leu Pro His Asp Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
    290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
            340                 345                 350

Gln Glu Pro Ser
        355

<210> SEQ ID NO 22

<211> LENGTH: 336
<212> TYPE: PRT
<213> ORGANISM: Pseudomonas syringae pv. syringae B728a

<400> SEQUENCE: 22

```
Met Lys Glu Pro Leu Lys Val Ala Cys Val Gln Ala Ala Pro Val Phe
1               5                   10                  15

Leu Asp Leu Asp Ala Thr Val Asp Lys Thr Ile Thr Leu Met Glu Gln
            20                  25                  30

Ala Ala Ala Ala Gly Ala Gly Leu Ile Ala Phe Pro Glu Thr Trp Ile
        35                  40                  45

Pro Gly Tyr Pro Trp Phe Leu Trp Leu Asp Ala Pro Ala Trp Asn Met
    50                  55                  60

Pro Leu Val Gln Arg Tyr His Gln Gln Ser Leu Val Leu Asp Ser Val
65                  70                  75                  80

Gln Ala Arg Arg Ile Ser Asp Ala Ala Arg His Leu Gly Leu Tyr Val
                85                  90                  95

Val Leu Gly Tyr Ser Glu Arg Asn Lys Ala Ser Leu Tyr Ile Gly Gln
            100                 105                 110

Trp Ile Ile Asp Asp His Gly Glu Thr Val Gly Val Arg Arg Lys Leu
        115                 120                 125

Lys Ala Thr His Val Glu Arg Thr Met Phe Gly Glu Gly Asp Gly Ala
    130                 135                 140

Ser Leu Arg Thr Phe Glu Thr Pro Val Gly Val Leu Gly Ala Leu Cys
145                 150                 155                 160

Cys Trp Glu His Leu Gln Pro Leu Ser Lys Tyr Ala Met Tyr Ala Gln
                165                 170                 175

Asn Glu Gln Ile His Val Ala Ala Trp Pro Ser Phe Ser Leu Tyr Arg
            180                 185                 190

Asn Ala Thr Ser Ala Leu Gly Pro Glu Val Asn Thr Ala Ala Ser Arg
        195                 200                 205

Val Tyr Ala Ala Glu Gly Gln Cys Phe Val Leu Ala Pro Cys Ala Ile
    210                 215                 220

Val Ser Pro Glu Met Ile Glu Met Leu Cys Asp Ser Asp Ala Lys Arg
225                 230                 235                 240

Ser Leu Leu Gln Ala Gly Gly His Ala Arg Ile Phe Gly Pro Asp
                245                 250                 255

Gly Ser Asp Leu Ala Thr Pro Leu Gly Glu His Glu Glu Gly Leu Leu
            260                 265                 270

Tyr Ala Thr Leu Asp Pro Ala Ala Leu Thr Leu Ala Lys Val Ala Ala
        275                 280                 285

Asp Pro Ala Gly His Tyr Ser Arg Pro Asp Val Thr Arg Leu Met Phe
    290                 295                 300

Asn Pro Asn Pro Thr Pro Cys Val Val Asp Leu Pro Asp Leu Pro Ile
305                 310                 315                 320

Ser Ser Glu Ser Ile Glu Leu Leu Arg Pro Asp Ile Ala Leu Glu Val
                325                 330                 335
```

<210> SEQ ID NO 23
<211> LENGTH: 345
<212> TYPE: PRT
<213> ORGANISM: Bradyrhizobium sp. BTAi1

<400> SEQUENCE: 23

```
Met Gly Leu Ala His Pro Lys Tyr Lys Val Ala Val Val Gln Ala Ala
1               5                   10                  15
```

```
Pro Ala Trp Leu Asp Leu Asp Ala Ser Ile Lys Lys Thr Ile Ala Leu
            20                  25                  30

Ile Glu Glu Ala Ala Asp Lys Gly Ala Lys Leu Ile Ala Phe Pro Glu
        35                  40                  45

Val Phe Ile Pro Gly Tyr Pro Trp His Ile Trp Met Asp Ser Pro Ala
    50                  55                  60

Trp Cys Ile Gly Arg Gly Phe Val Gln Arg Tyr Phe Asn Ser Leu
65                  70                  75                  80

Ala Tyr Asp Ser Pro Gln Ala Glu Ala Leu Arg Ala Val Arg Lys
                85                  90                  95

Ala Gln Leu Thr Ala Val Leu Gly Leu Ser Glu Arg Asp Gly Gly Ser
            100                 105                 110

Leu Tyr Ile Ala Gln Trp Leu Ile Gly Ala Asp Gly Glu Thr Ile Ala
        115                 120                 125

Lys Arg Arg Lys Leu Arg Pro Thr His Ala Glu Arg Thr Val Tyr Gly
    130                 135                 140

Glu Gly Asp Gly Ser Asp Leu Ala Val His Glu Arg Pro Asp Ile Gly
145                 150                 155                 160

Arg Ile Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
            180                 185                 190

Ser Phe Ser Leu Tyr Asp Pro Phe Ala Pro Ala Leu Gly Ala Glu Val
        195                 200                 205

Asn Asn Ala Ala Ser Arg Val Tyr Ala Val Glu Gly Ser Cys Phe Val
    210                 215                 220

Leu Ala Pro Cys Ala Thr Val Ser Gln Ala Met Ile Asp Glu Leu Cys
225                 230                 235                 240

Asp Arg Pro Asp Lys His Ala Leu Leu His Ala Gly Gly His Ala
                245                 250                 255

Ala Ile Phe Gly Pro Asp Gly Ser Ala Leu Ala Gln Leu Pro Pro
            260                 265                 270

Asp Gln Glu Gly Leu Leu Ile Ala Glu Ile Asp Leu Gly Met Ile Gly
        275                 280                 285

Ile Ala Lys Asn Ala Ala Asp Pro Ala Gly His Tyr Ser Arg Pro Asp
    290                 295                 300

Val Thr Arg Leu Leu Leu Asn Lys Lys Pro Leu Asn Arg Val Glu His
305                 310                 315                 320

Phe Ser Leu Pro Val Asp Ser Ala Ala Ala Leu Pro Gly Glu Ala
                325                 330                 335

Ala Val Ala Arg Pro Asp Gln Ser Ile
            340                 345

<210> SEQ ID NO 24
<211> LENGTH: 366
<212> TYPE: PRT
<213> ORGANISM: Rhodococcus rhodochrous NCIMB 11216

<400> SEQUENCE: 24

Met Val Glu Tyr Thr Asn Thr Phe Lys Val Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
```

-continued

```
                35                  40                  45
Val Phe Ile Pro Gly Tyr Pro Tyr His Ile Trp Val Asp Ser Pro Leu
 50                  55                  60

Ala Gly Met Ala Lys Phe Ala Val Arg Tyr His Glu Asn Ser Leu Thr
 65                  70                  75                  80

Met Asp Ser Pro His Val Gln Arg Leu Leu Asp Ala Ala Arg Asp His
                 85                  90                  95

Asn Ile Ala Val Val Gly Ile Ser Glu Arg Asp Gly Gly Ser Leu
                100                 105                 110

Tyr Met Thr Gln Leu Ile Ile Asp Ala Asp Gly Gln Leu Val Ala Arg
                115                 120                 125

Arg Arg Lys Leu Lys Pro Thr His Val Glu Arg Ser Val Tyr Gly Glu
130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
                180                 185                 190

Ser Leu Tyr Gln Pro Glu Val Pro Ala Phe Gly Val Asp Ala Gln Leu
                195                 200                 205

Thr Ala Thr Arg Met Tyr Ala Leu Glu Gly Gln Thr Phe Val Val Cys
                210                 215                 220

Thr Thr Gln Val Val Thr Pro Glu Ala His Glu Phe Phe Cys Glu Asn
225                 230                 235                 240

Glu Glu Gln Arg Lys Leu Ile Gly Arg Gly Gly Phe Ala Arg Ile
                245                 250                 255

Ile Gly Pro Asp Gly Arg Asp Leu Ala Thr Pro Leu Ala Glu Asp Glu
                260                 265                 270

Glu Gly Ile Leu Tyr Ala Asp Ile Asp Leu Ser Ala Ile Thr Leu Ala
                275                 280                 285

Lys Gln Ala Ala Asp Pro Val Gly His Tyr Ser Arg Pro Asp Val Leu
290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
                340                 345                 350

Ser Thr His Ser Asp Glu Thr Asp Arg Ala Thr Ala Thr Leu
                355                 360                 365

<210> SEQ ID NO 25
<211> LENGTH: 366
<212> TYPE: PRT
<213> ORGANISM: Rhodococcus rhodochrous ATCC 39484

<400> SEQUENCE: 25

Met Val Glu Tyr Thr Asn Thr Phe Lys Val Ala Ala Val Gln Ala Gln
 1                   5                  10                  15

Pro Val Trp Phe Asp Ala Ala Lys Thr Val Asp Lys Thr Val Ser Ile
                20                   25                  30

Ile Ala Glu Ala Ala Arg Asn Gly Cys Glu Leu Val Ala Phe Pro Glu
                35                   40                  45
```

-continued

```
Val Phe Ile Pro Gly Tyr Pro Tyr His Ile Trp Val Asp Ser Pro Leu
 50                  55                  60

Ala Gly Met Ala Lys Phe Ala Val Arg Tyr His Glu Asn Ser Leu Thr
 65                  70                  75                  80

Met Asp Ser Pro His Val Gln Arg Leu Leu Asp Ala Ala Arg Asp His
                 85                  90                  95

Asn Ile Ala Val Val Gly Ile Ser Glu Arg Asp Gly Gly Ser Leu
                100                 105                 110

Tyr Met Thr Gln Leu Ile Ile Asp Ala Asp Gly Gln Leu Val Ala Arg
                115                 120                 125

Arg Arg Lys Leu Lys Pro Thr His Val Glu Arg Ser Val Tyr Gly Glu
130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
                180                 185                 190

Ser Leu Tyr Gln Pro Glu Val Pro Ala Phe Gly Val Asp Ala Gln Leu
                195                 200                 205

Thr Ala Thr Arg Met Tyr Ala Leu Glu Gly Gln Thr Phe Val Val Cys
210                 215                 220

Thr Thr Gln Val Val Thr Pro Glu Ala His Glu Phe Phe Cys Glu Asn
225                 230                 235                 240

Glu Glu Gln Arg Met Leu Ile Gly Arg Gly Gly Gly Phe Ala Arg Ile
                245                 250                 255

Ile Gly Pro Asp Gly Arg Asp Leu Ala Thr Pro Leu Ala Glu Asp Glu
                260                 265                 270

Glu Gly Ile Leu Tyr Ala Asp Ile Asp Leu Ser Ala Ile Thr Leu Ala
                275                 280                 285

Lys Gln Ala Ala Asp Pro Val Gly His Tyr Ser Arg Pro Asp Val Leu
290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Phe Gly Ala Leu
                325                 330                 335

Asp Gly Val Arg Glu Leu Asn Gly Ala Asp Glu Gln Arg Ala Leu Pro
                340                 345                 350

Ser Thr His Ser Asp Glu Thr Asp Arg Ala Thr Ala Thr Leu
355                 360                 365
```

```
<210> SEQ ID NO 26
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 26 atg gtt tcg tat aac agc aag ttc ctc gcg gca acc gtt cag gca gag      48
Met Val Ser Tyr Asn Ser Lys Phe Leu Ala Ala Thr Val Gln Ala Glu
 1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
             20                  25                  30
```

| | | |
|---|---|---|
| atc gaa gaa gct gcc caa aag ggc gcg agt ctg atc gct ttc ccg gaa<br>Ile Glu Glu Ala Ala Gln Lys Gly Ala Ser Leu Ile Ala Phe Pro Glu<br>35 40 45 | | 144 |
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>50 55 60 | | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65 70 75 80 | | 240 |
| ggt gac gac cgt atg cgt cgc ctc cag ctg gcc gcg cgc aac aaa<br>Gly Asp Asp Arg Met Arg Arg Leu Gln Leu Ala Ala Arg Arg Asn Lys<br>85 90 95 | | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>100 105 110 | | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>115 120 125 | | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130 135 140 | | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145 150 155 160 | | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>165 170 175 | | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>180 185 190 | | 576 |
| cct ctt cag ccg gat gtt ttc caa cag agc atc gaa gcc aac gcg acg<br>Pro Leu Gln Pro Asp Val Phe Gln Gln Ser Ile Glu Ala Asn Ala Thr<br>195 200 205 | | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>210 215 220 | | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225 230 235 240 | | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>245 250 255 | | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>260 265 270 | | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>275 280 285 | | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290 295 300 | | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305 310 315 320 | | 960 |
| gac ggt cgc ttg gat gtg aat acc cgc agt cgc gtg gag aat ttc cga<br>Asp Gly Arg Leu Asp Val Asn Thr Arg Ser Arg Val Glu Asn Phe Arg<br>325 330 335 | | 1008 |
| ctg cga caa gcg gct gag cag gag cgt cag gca tcc aag cgg ctc gga<br>Leu Arg Gln Ala Ala Glu Gln Glu Arg Gln Ala Ser Lys Arg Leu Gly<br>340 345 350 | | 1056 |

```
acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365 aag tag                                                              1110
Lys
```

<210> SEQ ID NO 27
<211> LENGTH: 369
<212> TYPE: PRT
<213> ORGANISM: Acidovorax facilis 72W

<400> SEQUENCE: 27

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Gln Ser Ile Glu Ala Asn Ala Thr
        195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335
```

```
Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 28
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 28
```

| | | | | | | | | | | | | | | | | |
|---|---|---|---|---|---|---|---|---|---|---|---|---|---|---|---|---|
| atg gtt tcg tat aac agc aag ttc ctc gcg gca acc gtt cag gca gag | | | | | | | | | | | | | | | | 48 |
| Met Val Ser Tyr Asn Ser Lys Phe Leu Ala Ala Thr Val Gln Ala Glu | | | | | | | | | | | | | | | | |
| 1               5                   10                  15 | | | | | | | | | | | | | | | | |
| ccg gta tgg ctc gac gca gac gca acg atc gac aag tcg atc ggc atc | | | | | | | | | | | | | | | | 96 |
| Pro Val Trp Leu Asp Ala Asp Ala Thr Ile Asp Lys Ser Ile Gly Ile | | | | | | | | | | | | | | | | |
|             20                  25                  30 | | | | | | | | | | | | | | | | |
| atc gaa gaa gct gcc caa aag ggc gcg agt ctg atc gct ttc ccg gaa | | | | | | | | | | | | | | | | 144 |
| Ile Glu Glu Ala Ala Gln Lys Gly Ala Ser Leu Ile Ala Phe Pro Glu | | | | | | | | | | | | | | | | |
|         35                  40                  45 | | | | | | | | | | | | | | | | |
| gta ttc att ccg ggc tac ccc tat tgg gcg tgg ctc ggc gac gtg aag | | | | | | | | | | | | | | | | 192 |
| Val Phe Ile Pro Gly Tyr Pro Tyr Trp Ala Trp Leu Gly Asp Val Lys | | | | | | | | | | | | | | | | |
|     50                  55                  60 | | | | | | | | | | | | | | | | |
| tac agc cta agc ttt act tca cgc tat cac gag aat tcg ttg gag cta | | | | | | | | | | | | | | | | 240 |
| Tyr Ser Leu Ser Phe Thr Ser Arg Tyr His Glu Asn Ser Leu Glu Leu | | | | | | | | | | | | | | | | |
| 65                  70                  75                  80 | | | | | | | | | | | | | | | | |
| ggt gac gac cgt atg cgt cgc ctc cag ctg gcc gcg cgc cgc aac aaa | | | | | | | | | | | | | | | | 288 |
| Gly Asp Asp Arg Met Arg Arg Leu Gln Leu Ala Ala Arg Arg Asn Lys | | | | | | | | | | | | | | | | |
|             85                  90                  95 | | | | | | | | | | | | | | | | |
| atc gca ctc gtc atg ggc tat tcg gag cgg gaa gcc gga tcg cgc tat | | | | | | | | | | | | | | | | 336 |
| Ile Ala Leu Val Met Gly Tyr Ser Glu Arg Glu Ala Gly Ser Arg Tyr | | | | | | | | | | | | | | | | |
|         100                 105                 110 | | | | | | | | | | | | | | | | |
| ctg agc cag gtg ttc atc gac gag cgt ggc gag atc gtt gcc aat cgg | | | | | | | | | | | | | | | | 384 |
| Leu Ser Gln Val Phe Ile Asp Glu Arg Gly Glu Ile Val Ala Asn Arg | | | | | | | | | | | | | | | | |
|     115                 120                 125 | | | | | | | | | | | | | | | | |
| cgc aag ctg aag ccc aca cac gtt gag cgt acg atc tac ggc gaa ggc | | | | | | | | | | | | | | | | 432 |
| Arg Lys Leu Lys Pro Thr His Val Glu Arg Thr Ile Tyr Gly Glu Gly | | | | | | | | | | | | | | | | |
| 130                 135                 140 | | | | | | | | | | | | | | | | |
| aac gga acc gat ttc ctc acg cac gac ttc gcg ttc gga cgc gtc ggt | | | | | | | | | | | | | | | | 480 |
| Asn Gly Thr Asp Phe Leu Thr His Asp Phe Ala Phe Gly Arg Val Gly | | | | | | | | | | | | | | | | |
| 145                 150                 155                 160 | | | | | | | | | | | | | | | | |
| gga ttg aac tgc tgg gaa cat ttc caa ccg ctc agc aag ttc atg atg | | | | | | | | | | | | | | | | 528 |
| Gly Leu Asn Cys Trp Glu His Phe Gln Pro Leu Ser Lys Phe Met Met | | | | | | | | | | | | | | | | |
|             165                 170                 175 | | | | | | | | | | | | | | | | |
| tac agc ctc ggt gag cag gtc cac gtt gca tcg tgg ccg gcg atg tcc | | | | | | | | | | | | | | | | 576 |
| Tyr Ser Leu Gly Glu Gln Val His Val Ala Ser Trp Pro Ala Met Ser | | | | | | | | | | | | | | | | |
|         180                 185                 190 | | | | | | | | | | | | | | | | |
| cct ctt cag ccg gat gtt ttc caa gct agc atc gaa gcc aac gcg acg | | | | | | | | | | | | | | | | 624 |
| Pro Leu Gln Pro Asp Val Phe Gln Ala Ser Ile Glu Ala Asn Ala Thr | | | | | | | | | | | | | | | | |
|     195                 200                 205 | | | | | | | | | | | | | | | | |
| gtc acc cgc tcg tac gca atc gaa ggc caa acc ttt gtg ctt tgc tcg | | | | | | | | | | | | | | | | 672 |
| Val Thr Arg Ser Tyr Ala Ile Glu Gly Gln Thr Phe Val Leu Cys Ser | | | | | | | | | | | | | | | | |
| 210                 215                 220 | | | | | | | | | | | | | | | | |
| acg cag gtg atc gga cct agc gcg atc gaa acg ttc tgc ctc aac gac | | | | | | | | | | | | | | | | 720 |
| Thr Gln Val Ile Gly Pro Ser Ala Ile Glu Thr Phe Cys Leu Asn Asp | | | | | | | | | | | | | | | | |
| 225                 230                 235                 240 | | | | | | | | | | | | | | | | |

```
gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att     960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
        355                 360                 365 aag tag                                                             1110
Lys

<210> SEQ ID NO 29
<211> LENGTH: 369
<212> TYPE: PRT
<213> ORGANISM: Acidovorax facilis 72W

<400> SEQUENCE: 29

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190
```

```
Pro Leu Gln Pro Asp Val Phe Gln Ala Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 30
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 30 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
```

```
                Arg Lys Leu Lys Pro Thr His Val Glu Arg Thr Ile Tyr Gly Glu Gly
                    130                 135                 140 aac gga acc gat ttc ctc acg cac gac ttc gcg ttc gga cgc gtc ggt            480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg            528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc            576
Tyr Ser Leu Gly Glu Gln Val His Val Ala Ser Trp Pro Ala Met Ser
            180                 185                 190 cct ctt cag ccg gat gtt ttc caa tgt agc atc gaa gcc aac gcg acg            624
Pro Leu Gln Pro Asp Val Phe Gln Cys Ser Ile Glu Ala Asn Ala Thr
        195                 200                 205 gtc acc cgc tcg tac gca atc gaa ggc caa acc ttt gtg ctt tgc tcg            672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac            720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac            768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag            816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag            864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg            912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att            960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga           1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga           1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca           1104
Thr Lys Leu Phe Glu Gln Ser Leu Leu Ala Glu Glu Pro Val Pro Ala
        355                 360                 365 aag tag                                                                    1110
Lys <210> SEQ ID NO 31
<211> LENGTH: 369
<212> TYPE: PRT
<213> ORGANISM: Acidovorax facilis 72W

<400> SEQUENCE: 31

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45
```

```
Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Cys Ser Ile Glu Ala Asn Ala Thr
        195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 32
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 32 atg gtt tcg tat aac agc aag ttc ctc gcg gca acc gtt cag gca gag      48
Met Val Ser Tyr Asn Ser Lys Phe Leu Ala Ala Thr Val Gln Ala Glu
 1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
```

-continued

```
                  20                  25                  30 atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
         35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
 50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
            115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa acc agc atc gaa gcc aac gcg acg      624
Pro Leu Gln Pro Asp Val Phe Gln Thr Ser Ile Glu Ala Asn Ala Thr
            195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
```

```
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
            355                 360                 365 aag tag                                                              1110
Lys
```

<210> SEQ ID NO 33
<211> LENGTH: 369
<212> TYPE: PRT
<213> ORGANISM: Acidovorax facilis 72W

<400> SEQUENCE: 33

```
Met Val Ser Tyr Asn Ser Lys Phe Leu Ala Ala Thr Val Gln Ala Glu
1               5                  10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
```

```
                      325                 330                 335
Leu Arg Gln Ala Ala Glu Gln Glu Arg Gln Ala Ser Lys Arg Leu Gly
        340                 345                 350

Thr Lys Leu Phe Glu Gln Ser Leu Leu Ala Glu Glu Pro Val Pro Ala
        355                 360                 365

Lys

<210> SEQ ID NO 34
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 34 atg gtt tcg tat aac agc aag ttc ctc gcg gca acc gtt cag gca gag        48
Met Val Ser Tyr Asn Ser Lys Phe Leu Ala Ala Thr Val Gln Ala Glu
 1               5                  10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
             20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
         35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
     50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg       528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa gga agc atc gaa gcc aac gcg acg       624
Pro Leu Gln Pro Asp Val Phe Gln Gly Ser Ile Glu Ala Asn Ala Thr
        195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
```

```
                    225                 230                 235                 240
gaa cag cgc gca ctg ttg ccg caa gga tgt ggc tgg gcg cgc att tac         768
Glu Gln Arg Ala Leu Leu Pro Gln Gly Cys Gly Trp Ala Arg Ile Tyr
                        245                 250                 255 ggc ccg gat gga agc gag ctt gcg aag cct ctg gcg gaa gat gct gag         816
Gly Pro Asp Gly Ser Glu Leu Ala Lys Pro Leu Ala Glu Asp Ala Glu
                260                 265                 270 ggg atc ttg tac gca gag atc gat ctg gag cag att ctg ctg gcg aag         864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg         912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att         960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga        1008
Asp Gly Arg Leu Asp Val Asn Thr Arg Ser Arg Val Glu Asn Phe Arg
                    325                 330                 335 ctg cga caa gcg gct gag cag gag cgt cag gca tcc aag cgg ctc gga        1056
Leu Arg Gln Ala Ala Glu Gln Glu Arg Gln Ala Ser Lys Arg Leu Gly
                340                 345                 350 acg aaa ctc ttt gaa caa tcc ctt ctg gct gaa gaa ccg gtc cca gca        1104
Thr Lys Leu Phe Glu Gln Ser Leu Leu Ala Glu Glu Pro Val Pro Ala
            355                 360                 365 aag tag                                                                 1110
Lys
```

<210> SEQ ID NO 35
<211> LENGTH: 369
<212> TYPE: PRT
<213> ORGANISM: Acidovorax facilis 72W

<400> SEQUENCE: 35

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
```

-continued

```
                    180                 185                 190
Pro Leu Gln Pro Asp Val Phe Gln Gly Ser Ile Glu Ala Asn Ala Thr
            195                 200                 205
Val Thr Arg Ser Tyr Ala Ile Glu Gly Gln Thr Phe Val Leu Cys Ser
        210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
            340                 345                 350
Thr Lys Leu Phe Glu Gln Ser Leu Leu Ala Glu Glu Pro Val Pro Ala
        355                 360                 365
Lys

<210> SEQ ID NO 36
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 36 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125
```

| | | |
|---|---|---|
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130 135 140 | | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145 150 155 160 | | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>165 170 175 | | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>180 185 190 | | 576 |
| cct ctt cag ccg gat gtt ttc caa cac agc atc gaa gcc aac gcg acg<br>Pro Leu Gln Pro Asp Val Phe Gln His Ser Ile Glu Ala Asn Ala Thr<br>195 200 205 | | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>210 215 220 | | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225 230 235 240 | | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>245 250 255 | | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>260 265 270 | | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>275 280 285 | | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290 295 300 | | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305 310 315 320 | | 960 |
| gac ggt cgc ttg gat gtg aat acc cgc agt cgc gtg gag aat ttc cga<br>Asp Gly Arg Leu Asp Val Asn Thr Arg Ser Arg Val Glu Asn Phe Arg<br>325 330 335 | | 1008 |
| ctg cga caa gcg gct gag cag gag cgt cag gca tcc aag cgg ctc gga<br>Leu Arg Gln Ala Ala Glu Gln Glu Arg Gln Ala Ser Lys Arg Leu Gly<br>340 345 350 | | 1056 |
| acg aaa ctc ttt gaa caa tcc ctt ctg gct gaa gaa ccg gtc cca gca<br>Thr Lys Leu Phe Glu Gln Ser Leu Leu Ala Glu Glu Pro Val Pro Ala<br>355 360 365 | | 1104 |
| aag tag<br>Lys | | 1110 |

<210> SEQ ID NO 37
<211> LENGTH: 369
<212> TYPE: PRT
<213> ORGANISM: Acidovorax facilis 72W

<400> SEQUENCE: 37

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu

```
              35                  40                  45
Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
                115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln His Ser Ile Glu Ala Asn Ala Thr
                195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
                275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
                355                 360                 365

Lys
```

<210> SEQ ID NO 38
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 38

```
atg gtt tcg tat aac agc aag ttc ctc gcg gca acc gtt cag gca gag    48
Met Val Ser Tyr Asn Ser Lys Phe Leu Ala Ala Thr Val Gln Ala Glu
  1               5                  10                  15
```

-continued

| | | |
|---|---|---|
| ccg gta tgg ctc gac gca gac gca acg atc gac aag tcg atc ggc atc<br>Pro Val Trp Leu Asp Ala Asp Ala Thr Ile Asp Lys Ser Ile Gly Ile<br>        20                   25                  30 | | 96 |
| atc gaa gaa gct gcc caa aag ggc gcg agt ctg atc gct ttc ccg gaa<br>Ile Glu Glu Ala Ala Gln Lys Gly Ala Ser Leu Ile Ala Phe Pro Glu<br>         35                  40                   45 | | 144 |
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>50                   55                   60 | | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65                   70                   75                  80 | | 240 |
| ggt gac gac cgt atg cgt cgc ctc cag ctg gcc gcg cgc cgc aac aaa<br>Gly Asp Asp Arg Met Arg Arg Leu Gln Leu Ala Ala Arg Arg Asn Lys<br>                 85                  90                  95 | | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>                100                 105                110 | | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>        115                    120                   125 | | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130                   135                   140 | | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                   150                 155                160 | | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>                165                 170                175 | | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>                180                 185                190 | | 576 |
| cct ctt cag ccg gat gtt ttc caa aag agc atc gaa gcc aac gcg acg<br>Pro Leu Gln Pro Asp Val Phe Gln Lys Ser Ile Glu Ala Asn Ala Thr<br>        195                    200                   205 | | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>210                   215                   220 | | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                   230                 235                240 | | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                        245                 250                255 | | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>                260                 265                270 | | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>        275                    280                   285 | | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290                   295                   300 | | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305                   310                 315                320 | | 960 |
| gac ggt cgc ttg gat gtg aat acc cgc agt cgc gtg gag aat ttc cga<br>Asp Gly Arg Leu Asp Val Asn Thr Arg Ser Arg Val Glu Asn Phe Arg<br>                        325                 330                335 | | 1008 |

```
ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365 aag tag                                                              1110
Lys

<210> SEQ ID NO 39
<211> LENGTH: 369
<212> TYPE: PRT
<213> ORGANISM: Acidovorax facilis 72W

<400> SEQUENCE: 39

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Lys Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320
```

```
Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 40
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 40 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa        144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag        192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta        240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa        288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg        528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
            180                 185                 190 cct ctt cag ccg gat gtt ttc caa aat agc atc gaa gcc aac gcg acg        624
Pro Leu Gln Pro Asp Val Phe Gln Asn Ser Ile Glu Ala Asn Ala Thr
        195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
    210                 215                 220
```

-continued

```
acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa ggt tgt ggc tgg gcg cgc att tac      768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
    355                 360                 365 aag tag                                                             1110
Lys
```

<210> SEQ ID NO 41
<211> LENGTH: 369
<212> TYPE: PRT
<213> ORGANISM: Acidovorax facilis 72W

<400> SEQUENCE: 41

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175
```

-continued

```
Tyr Ser Leu Gly Glu Gln Val His Val Ala Ser Trp Pro Ala Met Ser
            180                 185                 190

Pro Leu Gln Pro Asp Val Phe Gln Asn Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 42
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 42

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
```

```
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc    432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt    480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg    528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc    576
Tyr Ser Leu Gly Glu Gln Val His Val Ala Ser Trp Pro Ala Met Ser
            180                 185                 190 cct ctt cag ccg gat gtt ttc caa tct agc atc gaa gcc aac gcg acg    624
Pro Leu Gln Pro Asp Val Phe Gln Ser Ser Ile Glu Ala Asn Ala Thr
        195                 200                 205 gtc acc cgc tcg tac gca atc gaa ggc caa acc ttt gtg ctt tgc tcg    672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac    720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac    768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag    816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag    864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga   1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga   1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca   1104
Thr Lys Leu Phe Glu Gln Ser Leu Leu Ala Glu Glu Pro Val Pro Ala
        355                 360                 365 aag tag                                                            1110
Lys

<210> SEQ ID NO 43
<211> LENGTH: 369
<212> TYPE: PRT
<213> ORGANISM: Acidovorax facilis 72W

<400> SEQUENCE: 43

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30
```

```
Ile Glu Glu Ala Ala Gln Lys Gly Ala Ser Leu Ile Ala Phe Pro Glu
         35                  40                  45

Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
             100                 105                 110

Leu Ser Gln Val Phe Ile Asp Glu Arg Gly Glu Ile Val Ala Asn Arg
         115                 120                 125

Arg Lys Leu Lys Pro Thr His Val Glu Arg Thr Ile Tyr Gly Glu Gly
         130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                 165                 170                 175

Tyr Ser Leu Gly Glu Gln Val His Val Ala Ser Trp Pro Ala Met Ser
             180                 185                 190

Pro Leu Gln Pro Asp Val Phe Gln Ser Ser Ile Glu Ala Asn Ala Thr
         195                 200                 205

Val Thr Arg Ser Tyr Ala Ile Glu Gly Gln Thr Phe Val Leu Cys Ser
         210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                 245                 250                 255

Gly Pro Asp Gly Ser Glu Leu Ala Lys Pro Leu Ala Glu Asp Ala Glu
             260                 265                 270

Gly Ile Leu Tyr Ala Glu Ile Asp Leu Glu Gln Ile Leu Leu Ala Lys
         275                 280                 285

Ala Gly Ala Asp Pro Val Gly His Tyr Ser Arg Pro Asp Val Leu Ser
         290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                 325                 330                 335

Leu Arg Gln Ala Ala Glu Gln Glu Arg Gln Ala Ser Lys Arg Leu Gly
             340                 345                 350

Thr Lys Leu Phe Glu Gln Ser Leu Leu Ala Glu Glu Pro Val Pro Ala
         355                 360                 365

Lys

<210> SEQ ID NO 44
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 44 atg gtt tcg tat aac agc aag ttc ctc gcg gca acc gtt cag gca gag      48
Met Val Ser Tyr Asn Ser Lys Phe Leu Ala Ala Thr Val Gln Ala Glu
```

```
1               5                    10                   15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
             20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
         35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
     50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
 65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                 85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
             100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
         115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
     130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat aaa caa ccg ctc agc aag ttc atg atg       528
Gly Leu Asn Cys Trp Glu His Lys Gln Pro Leu Ser Lys Phe Met Met
                 165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
             180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
         195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
     210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                 245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
             260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
         275                 280                 285 gct gga gcc gat ccg gtc ggg cac tat tcg cgg cct gac gtg ctg tcg       912
Ala Gly Ala Asp Pro Val Gly His Tyr Ser Arg Pro Asp Val Leu Ser
     290                 295                 300 gtc cag ttc gac ccg cgc aat cat acg cca gtt cat cgc atc ggc att       960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga      1008
```

```
                                                     -continued

Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
        355                 360                 365 aag tag                                                             1110
Lys

<210> SEQ ID NO 45
<211> LENGTH: 369
<212> TYPE: PRT
<213> ORGANISM: Acidovorax facilis 72W

<400> SEQUENCE: 45

Met Val Ser Tyr Asn Ser Lys Phe Leu Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
        50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Lys Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300
```

-continued

```
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Gln Ala Ala Glu Gln Glu Arg Gln Ala Ser Lys Arg Leu Gly
        340                 345                 350

Thr Lys Leu Phe Glu Gln Ser Leu Leu Ala Glu Glu Pro Val Pro Ala
    355                 360                 365

Lys

<210> SEQ ID NO 46
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 46 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat atg caa ccg ctc agc aag ttc atg atg     528
Gly Leu Asn Cys Trp Glu His Met Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg     624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
```

```
                210                 215                 220
acg cag gtg atc gga cct agc gcg atc gaa acg ttc tgc ctc aac gac    720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac    768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag    816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag    864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
            355                 360                 365 aag tag                                                            1110
Lys

<210> SEQ ID NO 47
<211> LENGTH: 369
<212> TYPE: PRT
<213> ORGANISM: Acidovorax facilis 72W

<400> SEQUENCE: 47

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160
```

```
Gly Leu Asn Cys Trp Glu His Met Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 48
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 48 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110
```

```
ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat acc caa ccg ctc agc aag ttc atg atg      528
Gly Leu Asn Cys Trp Glu His Thr Gln Pro Leu Ser Lys Phe Met Met
                165                 170                 175 tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365 aag tag                                                              1110
Lys

<210> SEQ ID NO 49
<211> LENGTH: 369
<212> TYPE: PRT
<213> ORGANISM: Acidovorax facilis 72W

<400> SEQUENCE: 49

Met Val Ser Tyr Asn Ser Lys Phe Leu Ala Ala Thr Val Gln Ala Glu
1               5                   10                  15
```

```
Pro Val Trp Leu Asp Ala Asp Ala Thr Ile Asp Lys Ser Ile Gly Ile
         20                  25                  30

Ile Glu Glu Ala Ala Gln Lys Gly Ala Ser Leu Ile Ala Phe Pro Glu
         35                  40                  45

Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Thr Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 50
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 50
```

```
                                                    -continued atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65              70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat gtg caa ccg ctc agc aag ttc atg atg       528
Gly Leu Asn Cys Trp Glu His Val Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg       912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att       960
Val Gln Phe Asp Pro Arg Asn His Thr Pro Val His Arg Ile Gly Ile
305                 310                 315                 320
```

```
gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
            355                 360                 365 aag tag                                                            1110
Lys

<210> SEQ ID NO 51
<211> LENGTH: 369
<212> TYPE: PRT
<213> ORGANISM: Acidovorax facilis 72W

<400> SEQUENCE: 51

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
```

```
                290                 295                 300
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 52
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 52 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg     624
Pro Leu Gln Pro Asp Val Phe Gln Leu Ser Ile Glu Ala Asn Ala Thr
        195                 200                 205
```

```
gtc gcc cgc tcg tac gca atc gaa ggc caa acc ttt gtg ctt tgc tcg      672
Val Ala Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                             1110
Lys

<210> SEQ ID NO 53
<211> LENGTH: 369
<212> TYPE: PRT
<213> ORGANISM: Acidovorax facilis 72W

<400> SEQUENCE: 53

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
```

-continued

```
              145                 150                 155                 160
Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Ala Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

```
<210> SEQ ID NO 54
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 54 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
```

| | | | | | | | | | | | | | | | |
|---|---|---|---|---|---|---|---|---|---|---|---|---|---|---|---|
| Ile | Ala | Leu | Val | Met | Gly | Tyr | Ser | Glu | Arg | Glu | Ala | Gly | Ser | Arg | Tyr |
| | | | 100 | | | | | 105 | | | | | 110 | | |

```
ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg       528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc tgc cgc tcg tac gca atc gaa ggc caa acc ttt gtg ctt tgc tcg       672
Val Cys Arg Ser Tyr Ala Ile Glu Gly Gln Thr Phe Val Leu Cys Ser
210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg       912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att       960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
        355                 360                 365 aag tag                                                              1110
Lys

<210> SEQ ID NO 55
<211> LENGTH: 369
<212> TYPE: PRT
<213> ORGANISM: Acidovorax facilis 72W

<400> SEQUENCE: 55

Met Val Ser Tyr Asn Ser Lys Phe Leu Ala Ala Thr Val Gln Ala Glu
```

```
            1               5                   10                  15
Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
                35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Leu Ser Ile Glu Ala Asn Ala Thr
            195                 200                 205

Val Cys Arg Ser Tyr Ala Ile Glu Gly Gln Thr Phe Val Leu Cys Ser
        210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365

Lys

<210> SEQ ID NO 56
<211> LENGTH: 1110
<212> TYPE: DNA
<213> ORGANISM: Escherichia coli SS1001
<220> FEATURE:
<221> NAME/KEY: CDS
<222> LOCATION: (1)..(1110)
```

<400> SEQUENCE: 56

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg     624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att     960
Val Gln Phe Asp Pro Arg Asn His Thr Pro Val His Arg Ile Gly Ile
```

```
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc tca gca      1104
Thr Lys Leu Phe Glu Gln Ser Leu Leu Ala Glu Glu Pro Val Ser Ala
        355                 360                 365 aag tag                                                               1110
Lys

<210> SEQ ID NO 57
<211> LENGTH: 369
<212> TYPE: PRT
<213> ORGANISM: Escherichia coli SS1001

<400> SEQUENCE: 57

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285
```

-continued

```
Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Ser Ala
        355                 360                 365

Lys
```